US011035795B2

(12) United States Patent
Cordovez et al.

(10) Patent No.: US 11,035,795 B2
(45) Date of Patent: Jun. 15, 2021

(54) METHODS FOR IDENTIFICATION OF PARTICLES IN A FLUID SAMPLE

(71) Applicant: OPTOFLUIDICS, INC., Philadelphia, PA (US)

(72) Inventors: Bernardo Cordovez, San Francisco, CA (US); Brian DiPaolo, Marlton, NJ (US); Gjergji Konica, King of Prussia, PA (US); Alexey Aprelev, Philadelphia, PA (US); Colby Ashcroft, Philadelphia, PA (US); Robert Hart, Philadelphia, PA (US)

(73) Assignee: Optofluidics, Inc., Philadelphia, PA (US)

( * ) Notice: Subject to any disclaimer, the term of this patent is extended or adjusted under 35 U.S.C. 154(b) by 0 days.

(21) Appl. No.: 16/726,357

(22) Filed: Dec. 24, 2019

(65) Prior Publication Data

US 2020/0217795 A1 Jul. 9, 2020

Related U.S. Application Data

(63) Continuation-in-part of application No. 15/438,092, filed on Feb. 21, 2017.

(60) Provisional application No. 62/360,832, filed on Jul. 11, 2016, provisional application No. 62/296,701, filed on Feb. 18, 2016.

(51) Int. Cl.
*G01N 21/64* (2006.01)
*G01N 1/30* (2006.01)
*G01N 33/68* (2006.01)

(52) U.S. Cl.
CPC .......... *G01N 21/6486* (2013.01); *G01N 1/30* (2013.01); *G01N 21/6458* (2013.01); *G01N 33/6803* (2013.01)

(58) Field of Classification Search
CPC combination set(s) only.
See application file for complete search history.

(56) References Cited

U.S. PATENT DOCUMENTS

| 2006/0027455 | A1* | 2/2006 | Patton | C07K 1/26 204/450 |
|---|---|---|---|---|
| 2006/0257991 | A1* | 11/2006 | McDevitt | C12M 41/36 435/287.2 |
| 2011/0106044 | A1* | 5/2011 | Trotter | A61K 47/26 604/403 |
| 2013/0137112 | A1* | 5/2013 | Patton | C09B 23/04 435/7.1 |

(Continued)

*Primary Examiner* — Jeffery A Williams
(74) *Attorney, Agent, or Firm* — Riverside Law LLP

(57) ABSTRACT

A method of distinguishing between proteinaceous and non-proteinaceous particulates in a fluid sample includes the steps of acquiring a brightfield background image of a membrane filter, introducing a fluid sample onto the membrane filter, acquiring a brightfield image of filtered particles resting on the membrane filter, generating a particle mask based on the brightfield background image and the brightfield image of filtered particles, introducing a fluorescent dye onto the membrane filter, detecting fluorescence on the particle mask, and distinguishing between proteinaceous and non-proteinaceous particulates based on the detected fluorescence. A method for detecting other types of particles, such as polysorbate particles, silicone oil or protein monomers is also disclosed.

26 Claims, 51 Drawing Sheets
(39 of 51 Drawing Sheet(s) Filed in Color)

(56) References Cited

U.S. PATENT DOCUMENTS

2014/0030788 A1\* 1/2014 Chen ................. B01L 3/502746
 435/177
2016/0153037 A1\* 6/2016 Hill ..................... C12Q 1/6881
 506/9

\* cited by examiner downstream downstream

IGG VS. BEADS
IN SITU WORKFLOW 1 USING 20 μL OF BIS-ANS DYE ON SUDAN BLACK PLATE, OLYMPUS SCOPE

IGG VS. CELLULOSE
IN SITU WORKFLOW 1 USING 20 μL OF BIS-ANS DYE ON SUDAN BLACK PLATE, OLYMPUS SCOPE – great separation in all these data sets

| Cumulative Bin Separation (μm) | Ratio 10th IgG to 90th ETFE | Ratio Median IgG to Median ETFE |
|---|---|---|
| 2 | -0.1 | 10.8 |
| 3 | -0.7 | 16.4 |
| 4 | 3.6 | 32.5 |
| 5 | 7.1 | 36.8 |
| 6 | 11.0 | 37.5 |
| 7 | 11.6 | 56.6 |
| 8 | 5.2 | 58.3 |
| 9 | 6.3 | 28.8 |
| 10 | 3.3 | 28.3 |

FIG. 44

METHODS FOR IDENTIFICATION OF PARTICLES IN A FLUID SAMPLE

CROSS-REFERENCE TO RELATED APPLICATIONS

This application is a continuation-in-part of U.S. nonprovisional application Ser. No. 15/438,092 filed on Feb. 21, 2017, which claims priority to U.S. Provisional Patent Application No. 62/360,832, filed Jul. 11, 2016, and U.S. Provisional Patent Application No. 62/296,701, filed Feb. 18, 2016, all of which are incorporated herein by reference in their entireties.

BACKGROUND OF THE INVENTION

Protein therapeutics have grown dramatically over the past 25 years and now comprise 15-30% of the pharmaceutical market. The primary quality concern for this class of therapeutics is that they can elicit an immune response from patients who develop anti-drug antibodies. High levels of anti-drug antibodies can eliminate therapeutic effects by clearing the drug from the body. This immune response affects 1-10% of patients, who must stop taking the medication and will return to their initial diseased state. The presence of particulate matter in these therapeutics (e.g. shed glass from a syringe or a protein aggregate) enhances this immune response and the Federal Drug Administration (FDA) therefore regulates the amount of particles that can be present.

There are existing tools that can provide particle counts and size in the FDA regulated size range, however there is no instrumentation that can routinely and rapidly identify what the particles are actually made of (see e.g. Bee J S, Goletz T J, Ragheb J A. The future of protein particle characterization and understanding its potential to diminish the immunogenicity of biopharmaceuticals: a shared perspective. J Pharm Sci. 2012 October; 101(10):3580-5; Ripple D C, Dimitrova M N. Protein particles: What we know and what we do not know. Journal of Pharmaceutical Sciences. 2012 October; 101(10):3568-79; and Zölls S, Tantipolphan R, Wiggenhorn M, Winter G, Jiskoot W, Friess W, et al. Particles in therapeutic protein formulations, Part 1: Overview of analytical methods. J Pharm Sci. 2012 Mar. 1; 101(3):914-35). There are numerous analytical instruments used to characterize particulates in protein therapeutics. They can be classified as particle counting techniques and particle identification techniques. The main particle counting techniques for the regulated space of 10 microns and above include light obscuration (the primary workhorse), membrane microscopy, coulter counters and microflow imaging (MFI). MFI is a newer technology in this space and has proliferated rapidly. It can provide particle counts but can be considered a bit of a hybrid because image morphology and brightness can act as a form of crude particle identification. Specifically, the system can identify oil droplets and air bubbles and distinguish them from the more solid particles due to their spherical nature. Further identification is not as trusted but some guesses can be made by looking at opacity and shape as to whether the particle is a protein aggregate or a piece of metal. Certainly this identification is qualitative and not definitive. Smaller sized particles in the unregulated space can be analyzed using a variety of instruments which are not yet quantitative enough in measuring protein therapeutic samples for the FDA to regulate this space or make a technique recommendation. These include Nanoparticle Tracking Algorithm (NTA) instruments, Resonant Mass Measurement (RMM) instruments (i.e. the Archimedes system) that can also detect oil droplets, Dynamic Light Scattering (DLS) which is not quantitative in terms of particle count and the Izon system.

For more definitive identification scientists typically rely on (1) spectroscopy, primarily FTIR and Raman inspection of particles trapped on a filter surface, (2) elemental analysis on an electron microscope and occasionally (3) fluorescence microscopy after staining particles. Each of these techniques is a powerful and useful way to carry out forensic analysis of particles. In general, they are not routine measurement instruments and are only used occasionally due to low throughput and the complexity of sample prep. Electron microscopy is expensive, requires complicated sample prep, highly trained operators and high vacuum conditions. Fluorescence microscopy requires staining of the particles which is undesirable. In the protein therapeutic space, any changes to the sample, including dilution temperature change, additional reagents added can disrupt the delicate balance of the carefully formulated sample. There is always a fear that the changes to the sample will affect the measurement, especially in the case of a dye that chemically associates with the particles of interest.

Thus, instruments do exist that can identify particles, but they are difficult to operate and take a long time to provide results, preventing routine usage. Some materials are more dangerous than others, and knowing what the particles are made of would allow for quickly tracking the contamination back to its source and eliminating it (see e.g. Rosenberg A S. Effects of protein aggregates: An immunologic perspective. AAPS J. 2006 Aug. 4; 8(3):E501-7; and Carpenter J F, Randolph T W, Jiskoot W, Crommelin D J A, Middaugh C R, Winter G, et al. Overlooking subvisible particles in therapeutic protein products: gaps that may compromise product quality. J Pharm Sci. 2009 April; 98(4):1201-5.) The lack of a routine identification technique means that scientists typically don't know what's in their samples and cannot therefore detect harmful contamination early enough. Instead, scientists only begrudgingly use particle identification equipment during troubleshooting efforts due to their tedious operation and low throughput. This is a source of great frustration which slows product development and reduces overall quality and safety.

Current particle analysis systems are also very inefficient. At the formulation selection stage and before manufacturing, researchers have very little sample available. Current tools requires hundreds of microliters and are very low speed. As a result, researchers often avoid sub visible particle analysis altogether, or conduct such analysis sparingly in the earlier stages. It is well known that sub visible particle analysis is one of the most sensitive measurements for formulation stability. The ability for researchers to have better and more efficient analysis tools available at early research stages would be a great improvement to the art.

Current particle analysis systems are also inefficient at particle identification. For example, while imaging and gathering particle distributions (e.g. concentration vs. size) is valuable, the ability to learn about what a particle is, such as quickly distinguishing between proteinaceous and non-proteinaceous samples adds significant value. The ability for protein identification can allow for selection of a formation that has the least number of protein aggregates and is most stable over time. Identification of protein aggregates also allows for early and efficient formulation screening, informing users early in the formulation process of whether they need to adjust the formulation itself, vs. looking at excipients or environmental factors.

Several conventional spectroscopic microscopy techniques enable the specific detection of chemical groups and compounds for particulate analysis, including Raman spectroscopy and FTIR.

Raman spectroscopy has been used in several products due to its ability to detect chemical bonds with high specificity. However, it works based on a very weak nonlinear signal and thus requires a focused laser beam excitation to localize a very strong excitation. The focused laser approach means that Raman requires rastering this small laser spot to cover a larger area, making it dramatically low throughput by having to raster slowly through a sample, and the low Raman signal means that typically acquisition time per spot can take several minutes. Also, while Raman is information rich, it requires the use of complex spectral libraries to then match it to the compound of interest. This makes it very slow and complicated to use. For example, it can take several hours to sample a few square millimeters in Raman when a single well can have >30 mm^2 of area. It is several orders of magnitude away from routine use.

FTIR emerges as an interesting solution as it is higher throughput than Raman. But complications due to signal masking (for example excipients can absorb the same wavelength as the drug product itself), it can complicate its accuracy on distinguishing between product and not product (e.g. Protein and not protein). Also, it has an inability to work with materials with any water content, making it complicated for certain applications (e.g. filtered proteins) that can retain some of their hydration.

Flow Imagers, also known as dynamic particle imagers, image particles flowing in a fluidic stream and conduct subsequent image analysis. They rely exclusively on morphology to qualify particles. This is not good enough for accurate particle identification or even categorization of general groups (like protein, non-protein). For example, NIST now makes protein aggregate mock standards made from plastic, called ETFE (Ethylene tetrafluoroethylene). These small shaved pieces of plastic look just like protein aggregates and are even designed to match their refractive index, therefore morphology alone cannot distinguish between proteins and non-proteins. A flow imager would say that ETFE is a protein aggregate when it is not. Further, if a protein aggregate is measured in water, there is very little contrast (the protein aggregate in liquid has almost the same optical properties as the liquid itself), whereas if it can somehow be measured in dry air, the inherent contrast of the measurement goes up, making it possible to resolve protein aggregates >1 um.

Thus, there is a need in the art for an improved methods of high throughput identification and distinguishing between particles, such as between proteinaceous and non-proteinaceous particulates in a fluid sample.

SUMMARY OF THE INVENTION

In one embodiment, a method of distinguishing between proteinaceous and non-proteinaceous particulates in a fluid sample includes the steps of acquiring a brightfield background image of a membrane filter; introducing a fluid sample onto the membrane filter; acquiring a brightfield image of filtered particles resting on the membrane filter; generating a particle mask based on the brightfield background image and the brightfield image of filtered particles; introducing a fluorescent dye onto the membrane filter; detecting fluorescence on the particle mask; and distinguishing between proteinaceous and non-proteinaceous particulates based on the detected fluorescence. In one embodiment, the method includes the step of generating a total particle distribution, a protein particle distribution, and a non-protein particle distribution based on the distinguishing. In one embodiment, the method includes the step of generating an image of protein and non-protein particles, wherein the protein and non-protein particles are different colors. In one embodiment, the method includes the step of ignoring data outside the particle mask for the steps of detecting and distinguishing. In one embodiment, the method includes the step of acquiring a background fluorescence and removing baseline fluorescent intensity. In one embodiment, the step of introducing a fluorescent die takes place immediately after the step of introducing a fluid sample onto the membrane filter. In one embodiment, the fluorescent dye is introduced to the fluid sample prior to the step of introducing the fluid sample onto the membrane filter. In one embodiment, the membrane filter is a track etched membrane. In one embodiment, the membrane filter is dyed with a fluorescence photo absorber. In one embodiment, the photo absorber comprises sudan black dye. In one embodiment, the membrane filter comprises a polycarbonate or polyester. In one embodiment, the membrane filter is coated with PVP. In one embodiment, the step of introducing a fluorescent dye comprises introducing between 5 and 50 uL of dye. In one embodiment, the fluid sample is bounded by a hydrophobic ring disposed on a well plate. In one embodiment, the method includes the step of individually and separately imaging a plurality of fluid sampled bounded by a plurality of hydrophobic rings disposed on the well plate.

In one embodiment, a method of distinguishing between particulates in a fluid sample includes the steps of acquiring a brightfield background image of a membrane filter; introducing a fluid sample onto the membrane filter; acquiring a brightfield image of filtered particles resting on the membrane filter; generating a particle mask based on the brightfield background image and the brightfield image of filtered particles; introducing a fluorescent dye onto the membrane filter; detecting fluorescence on the particle mask; and distinguishing between particulates based on the detected fluorescence. In one embodiment, the fluorescent dye is selected for detecting protein particles. In one embodiment, the fluorescent dye is a protein aggregate dye. In one embodiment, the fluorescent dye is a monomer dye. In one embodiment, the fluorescent dye is selected for detecting polysorbate particles. In one embodiment, the fluorescent dye is selected for detecting silicone oil. In one embodiment, the fluorescent dye is selected for detecting protein monomers. In one embodiment, the method includes the step of ignoring data outside the particle mask for the steps of detecting and distinguishing. In one embodiment, the method includes the step of acquiring a background fluorescence and removing baseline fluorescent intensity. In one embodiment, the membrane filter is dyed with a fluorescence photo absorber. In one embodiment, the photo absorber comprises sudan black dye.

In one embodiment, a system for characterizing at least one particle from a fluid sample includes a filter disposed upstream of an outlet; a luminaire configured to illuminate the at least one particle at an oblique angle; and an imaging device configured to capture and process images of the illuminated at least one particle as it rests on the filter for characterizing the at least one particle. In one embodiment, the system includes a luminaire configured to illuminate the at least one particle at an angle coplanar with a flat plane of the filter. In one embodiment, the luminaire comprises a plurality of illuminating devices. In one embodiment, the plurality of illuminating devices are disposed radially around and directed inwardly towards the filter. In one embodiment, the illuminating devices are LEDs. In one embodiment, the system includes a luminaire configured to illuminate the at least one particle by bright field illumination. In one embodiment, the imaging system is configured to generate a composite image comprising oblique angle illumination and bright field illumination. In one embodiment, the imaging system is configured to characterize a plurality of particles based on a combination of oblique angle illumination and bright field illumination. In one embodiment, a well plate having a plurality of wells that each terminate on a filter. In one embodiment, the filter is a membrane. In one embodiment, the membrane is black. In one embodiment, the surface has a low surface roughness. In one embodiment, the well plate comprises a transparent material. In one embodiment, the well plate comprises a transparent material with an opaque layer on the top surface. In one embodiment, the well plate comprises a reflective film. In one embodiment, the well plate comprises an opaque bright white material. In one embodiment, the plurality of wells have a decreasing radius moving towards the filter. In one embodiment, the system includes a vacuum manifold connected to a negative pressure source and configured for fluid communication with the plurality of wells. In one embodiment, the well plate comprises an optical feature comprising at least one of a mirror, lens and prism. In one embodiment, the imaging device is configured to characterize and identify a material type of the at least one particle using a machine learning algorithm. In one embodiment, the machine learning algorithm uses observed features including at least one of size, shape, texture, dark-field intensity and intrinsic fluorescence of particles to build models. In one embodiment, the machine learning algorithm is a boosting algorithm. In one embodiment, the machine learning algorithm uses neural networks. In one embodiment, the machine learning algorithm uses convolutional neural networks. In one embodiment, the imaging device is configured to characterize and identify a material type of the at least one particle as it rests on the filter using fluorescent imaging. In one embodiment, fluorescent imaging comprises intrinsic multi channel based fluorescence. In one embodiment, fluorescent imaging comprises labeled multichannel based fluorescence. In one embodiment, the imaging device is configured to image the filter both before and after the at least one particle is captured on the filter. In one embodiment, the before and after images are processed together using algorithms that processes them to find differences. In one embodiment, the imaging device is configured to take a plurality of images at a plurality of heights above the filter. In one embodiment, the plurality of images consists of a high dynamic range set of exposures. In one embodiment, the plurality of images are merged together into a single image. In one embodiment, the plurality of images comprises replicates. In one embodiment, the plurality of images at different heights are merged together into a single image. In one embodiment, the before and after images are mathematically registered. In one embodiment, a median filter is used to process the image. In one embodiment, two or more images are mathematically registered. In one embodiment, the imaging device is configured to image the at least one particle a plurality of times. In one embodiment, the imaging device is configured to process the images to provide at least one of a number of particles, a size of particles and a light scattering of particles. In one embodiment, the system includes a negative pressure source in fluid communication with openings in the filter. In one embodiment, the system includes a wicking material downstream of the filter and upstream of the outlet. In one embodiment, the filter is a component of a chip. In one embodiment, the chip is substantially planar.

In one embodiment, a method for characterizing at least one particle from a fluid sample comprising: introducing a fluid sample onto a filter; illuminating the at least one particle at an oblique angle; and imaging the illuminated at least one particle as it rests on the filter for characterizing the at least one particle. In one embodiment, the method includes the steps of illuminating the at least one particle using bright field illumination. In one embodiment, the method includes the steps of generating a composite image based on the oblique angle and bright field illumination. In one embodiment, the method includes the steps of illuminating the at least one particle by radially surrounding the at least one particle with a plurality of illuminating devices and illuminating the at least one particle from an oblique angle. In one embodiment, the method includes the steps of illuminating the at least one particle in one of a plurality of wells disposed on a well plate. In one embodiment, the method includes the steps of charactering the at least one particle based on imaging prior to an after a fluid sample is introduced onto the filter. In one embodiment, the method includes the steps of individually and separately imaging each of the plurality of wells. In one embodiment, the step if imaging comprises imaging at a plurality of heights above the filter. In one embodiment, the plurality of images comprises a high dynamic range set of exposures. In one embodiment, the method includes the steps of merging the plurality of images together into a single image. In one embodiment, the plurality of images comprises replicates. In one embodiment, the method includes the steps of mathematically registering two or more images. In one embodiment, the method includes the steps of mathematically registering before and after images. In one embodiment, the method includes the steps of introducing the fluid sample into a well on a well plate. In one embodiment, the method includes the steps of illuminating the at least one particle through an optical feature of the well plate comprising at least one of a mirror, lens and prism. In one embodiment, the method includes the steps of characterizing and identifying a material type of the at least one particle using a machine learning algorithm. In one embodiment, the machine learning algorithm uses observed features including at least one of size, shape, texture, dark-field intensity and intrinsic fluorescence of particles to build models.

In one embodiment, a system for characterizing at least one particle from a fluid sample includes a filter disposed upstream of an outlet; a luminaire configured to illuminate the at least one particle using bright field illumination; and an imaging device configured to capture and process images of the illuminated at least one particle as it rests on the filter for characterizing the at least one particle. In one embodiment, the system includes a luminaire configured to illuminate the at least one particle at an oblique angle. In one embodiment, the system includes a luminaire configured to illuminate the at least one particle at an angle coplanar with a flat plane of the filter. In one embodiment, the luminaire comprises a plurality of illuminating devices. In one embodiment, the plurality of illuminating devices are disposed radially around and directed inwardly towards the filter. In one embodiment, the filter is disposed on a chip. In one embodiment, the chip is substantially planar. In one embodiment, the filter comprises a first micropore grid. In one embodiment, the filter comprises a polymer or metallic membrane.

In one embodiment, a method for characterizing at least one particle from a fluid sample includes the steps of introducing a fluid sample onto a filter; illuminating the at least one particle using bright field illumination; and imaging the illuminated at least one particle as it rests on the filter for characterizing the at least one particle. In one embodiment, the method includes the steps of illuminating the at least one particle at an oblique angle or an angle coplanar with a flat plane of the filter. In one embodiment, the method includes the steps of illuminating the at least one particle by radially surrounding the at least one particle with a plurality of illuminating devices and illuminating the at least one particle from an oblique or coplanar angle. In one embodiment, the method includes the steps of illuminating the at least one particle in one of a plurality of wells disposed on a well plate, wherein each of the wells terminates in a filter.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing purposes and features, as well as other purposes and features, will become apparent with reference to the description and accompanying figures below, which are included to provide an understanding of the invention and constitute a part of the specification, in which like numerals represent like elements, and in which:

FIG. 44 shows a data separation table according to one embodiment.

DETAILED DESCRIPTION OF THE INVENTION

Figure 1A:
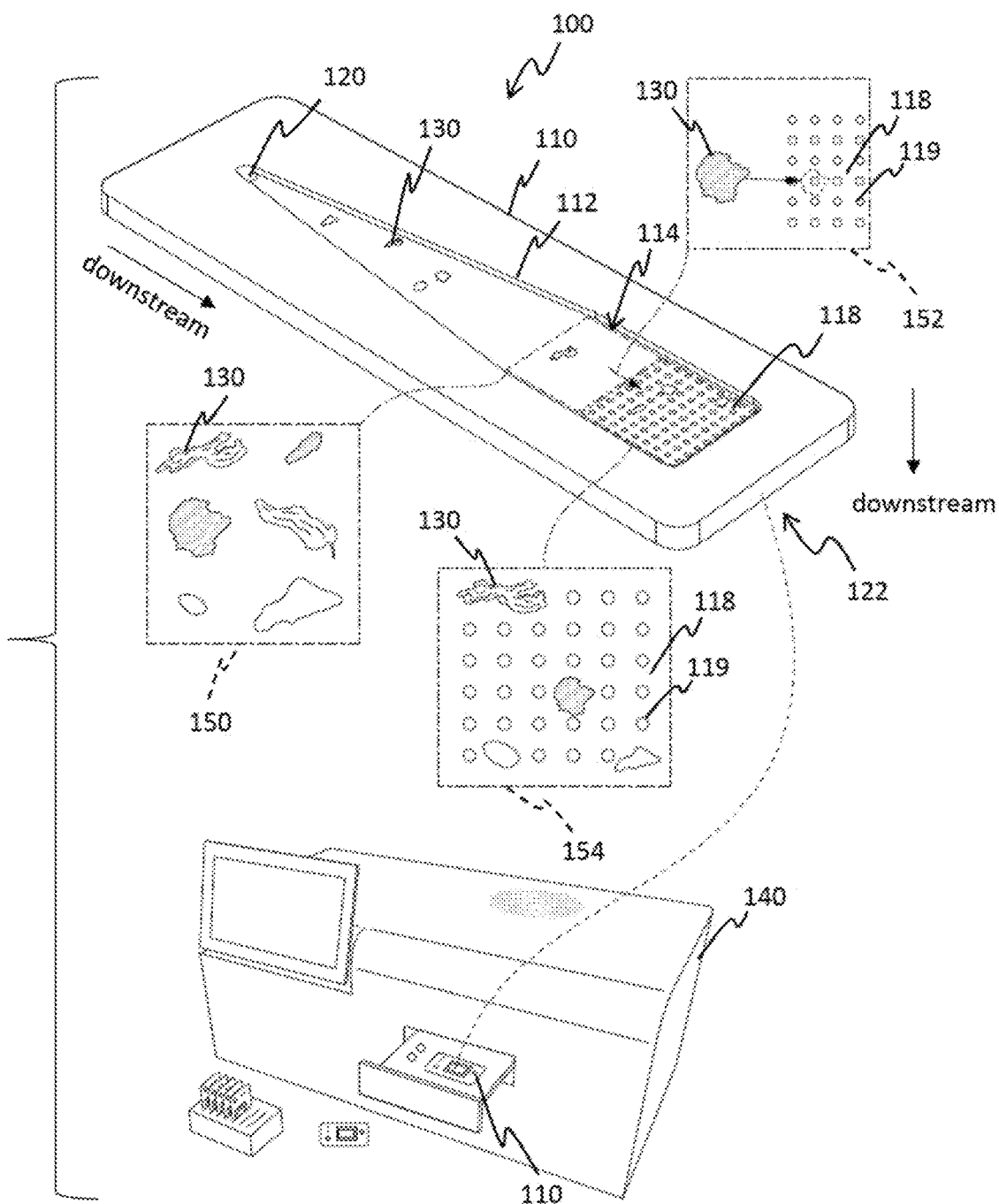
FIG. 1A is a diagram of a system for characterizing particulates in a fluid sample according to one embodiment.

It is to be understood that the figures and descriptions of the present invention have been simplified to illustrate elements that are relevant for a more clear comprehension of the present invention, while eliminating, for the purpose of clarity, many other elements found in systems and methods of characterizing particulates in a fluid sample. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a system and method for characterizing particulates in a fluid sample.

With reference now to FIG. 1A, a system 100 for characterizing particulates 130 in a fluid sample is shown. The system 100 includes a chip 110 having a fluid channel 112 that is configured to allow a fluid sample to flow downstream through an imaging region 114 and a filter 118, before exiting through an outlet 122 (underneath the filter in the view of FIG. 1A). In one embodiment, the outlet is any space or void in the system downstream of the filter that is in fluid communication with openings in the filter. The downstream direction is relative to the filter. Thus, downstream is the direction that a fluid sample would normally move as it flows towards and/or through the filter (e.g. laterally east or west and/or down in certain embodiments). In certain embodiments, the flow is generated by a negative pressure source applying a vacuum pressure to the fluid channel or the outlet. In certain embodiments, the outlet 122 is underneath or otherwise downstream of the filter 118. The filter 118 has multiple pores 119 through which fluid can flow, while trapping particles 130 present within the fluid sample. Advantageously, embodiments of the system provide high throughput particle identification that is at least an order of magnitude faster than conventional systems, while particle counting information is consistent with state-of-the art instrumentation. Particles 130 are imaged by an imaging device 140 as they travel down the fluid channel 112 and are caught at the outlet 122 by a filter 118, which in certain embodiments is a high density micropore grid which acts like a sieve. The sieve with captured particles resting on top can be imaged, for example by FTIR to provide particle identity. Whereas this type of analysis using conventional technology can take several hours to accomplish, embodiments described herein are able to carry out both counting and typing within 30 minutes or less. The additional typing capability of a routine particle counting instrument accelerates clinical development and enables higher quality, safer therapeutics.

In one embodiment, fluid samples are injected into a chip 110 having a fluid channel 112 that includes an imaging region 114 and a filter 118. Particles 130 are imaged as they travel down the fluid channel 112, 150. In one embodiment, the particle analysis is microflow imaging (MFI), which is currently a preferred method of routine characterization in the compendial (regulated) particle range. In conventional MFI systems, the fluid sample is imaged then pumped to waste. In embodiments described herein, the outlet 122 of the channel 112 is blocked by a filter 118, which in certain embodiments is a grid of lithographically defined pores 119 which act like a sieve. Particles 130 that are larger than the pores 119 are trapped by the sieve. The grid is very dense and can fit within the field of view of the camera. Particles 130 are imaged multiple times and tracked to their landing site in the filter 118, 152. After the sample has been fully pumped through, imaging (e.g. FTIR imaging) is used to characterize and identify the trapped particles 130, 154 and assign a material type. The nicely defined grid on the filter 118 is ideal for rapid scanning and spectra for each particle can be linked to the particle's image (from step 150). In certain embodiments, dynamic fluid delivery and control systems are implemented. As the filter is filled up, the flow resistance will increase, and the presence of flow sensors and pressure feedback can dynamically change or maintain the flow rate. Otherwise, poor control could either rupture the membrane or push deformable particles through the membrane.

In one embodiment, the channel 112 is imaged using magnification optics and with a bright blue LED flash that is timed with a camera exposure. This method of delivering particles into a flow cell and imaging them is how current MFI instruments work (e.g. ProteinSimple, Fluid Imaging Technologies). For MFI analysis, careful automation can be used to time the flash illumination and exposure together with the fluid flow so that particles are not missed between exposures. In certain embodiments, numerous pictures of each particle are taken in order to track them and correlate the images to FTIR analysis.

Figure 1B:
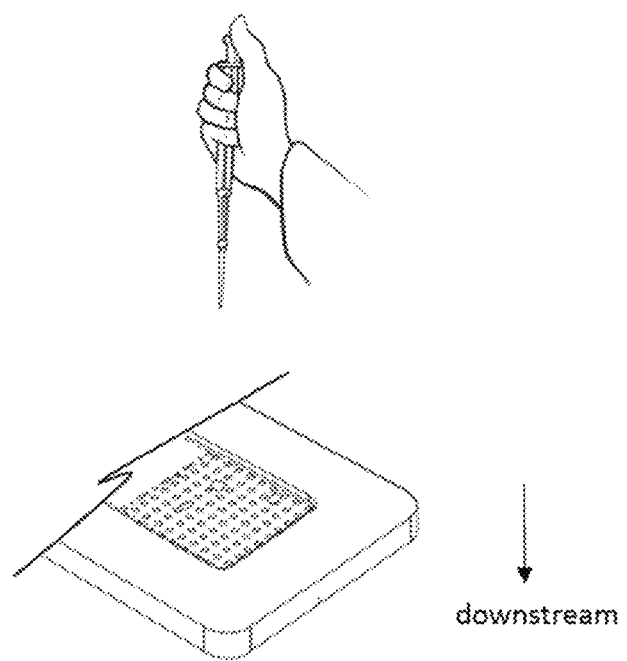
FIG. 1B is a diagram of a system where the fluid sample is pipetted directly onto the filter.

In certain embodiments, the chip has a shorter fluid channel or no fluid channel at all, and fluid samples are pipetted directly onto the filter (see for example FIG. 1B). In this type of embodiment, imaging and particle characterization can be based solely on imaging particles on the filter. In certain embodiments, filters may be stacked in series so that the holes get progressively smaller. For example, one embodiment can include 3 filters (a 25 um filter, 10 um filter and a 2 um filter). In certain embodiments, filter material can be modified to suit the form of spectroscopy used. In the case of FTIR, a transparent membrane can be used (for example silicon nitride or silicon dioxide). In the case of Raman spectroscopy, a metallic coating of gold or silver can be deposited onto the surface. In certain embodiments, the filter surface can be modified with anti-fouling agents (e.g. PEG, functional silanes, surfactants) to avoid fouling or reduce flow resistance or capillary pressure of pores (e.g. with hydrophilic PEG coating). In certain embodiments, pore shape in all three dimensions can be precisely controlled. For example, conical pores can be utilized to improve capture efficiency and trapped location accuracy of filtered objects. In certain embodiments, consistent pore size and density is utilized to lead to consistent transmission of light. Reduction in light transmission can also be used to quantify trapped particle concentration and/or determine composition considering wavelength of excitation.

In one embodiment, particles larger than the pore size will be trapped. In one embodiment, since both the main channel and the grid will be within the field of view of the camera, particles can be tracked directly to their landing site on the pore grid. The pore grid can be made by optical lithography which can precisely pattern tightly packed holes with a high amount of total open area. In one embodiment, each particle, after it is tracked to its landing site will have a high quality image associated with it (from step 150) (just as in the MFI systems) and an x and y grid position specifying its location. This is important for the next step where the identification is performed. One advantage of tying images to spectra is for additional corroboration, e.g. particles that look like protein aggregates and also have a protein aggregate spectrum provide added confidence. In certain embodiments, multiple images of the same particle are used to provide a higher level of morphological and/or optical scattering intensity analysis.

In certain embodiments, in order to make particle tracking more accurate, a more sophotiscated particle location prediction is utilized. Imaging particles in the flow stream with the filter in the field of view makes it possible to connect the landed particle to the flowing particle and tie together spectroscopy and morphology. Prediction methods are based on hydrodynamics and improve the accuracy of the spectroscopy-morphology linking. In certain embodiments, the following pieces of information can be utilized to make a good prediction: (1) Particles generally stay within their streamline. If flow is from left to right, particles flowing at one "latitude" will likely land at around the same latitude. (2) Landing particles will be seen on the filter itself. (3) A video of particles can be used to identify particle velocity. There will be low Reynolds number Poiseuille flow conditions. Particle velocity allows the prediction of height of the particle within the channel and therefore allows prediction of a possible landing site. For example, particles with the fastest velocity will be in the middle (height-wise) of the channel. If flow occurs from left to right, particles will likely land in the center "longitudes" (i.e. East-West) of the filter.

In certain embodiments, particle imaging occurs after the particles have landed on the filter (rather than in the flow cell as is explained above in step 150 and 152). Multiple images can be taken throughout the filtration process so that particles which land close to each other can be distinguished by observing their landing times. The grid can be transparent allowing for many different types of imaging. Since the particles are stationary after they have been captured, long exposure times and multiple imaging methods can be used sequentially of the same particles and will allow images to be overlaid and so that each particle can be linked between images.

Rapid particle identification (e.g. FTIR imaging, step 154) takes place after all of the sample is run through the channel 112 and particles 130 are collected on the filter 118. FTIR imaging is used to carry out high throughput spectroscopy on the tightly packed and neatly arranged particles. FTIR spectra can be used to identify the particles but also carry out protein structural analysis on protein aggregates to learn the extent of the damage[38]. FTIR is a form of vibrational spectroscopy widely used in protein therapeutics. There are at least two advantages for selecting FTIR imaging over Raman spectroscopy, which is another possible choice in alternate embodiments. First, time savings—since these particles are packed neatly into a tight grid, FTIR imaging can be used to analyze numerous particles at once unlike Raman which has slower acquisition times and must scan a laser spot. A Raman scan that might take several hours can be compressed down to 5 minutes with an FTIR imaging system. This is critical to make the system a routine analysis system. Second, it is preferred by segments of the market since FTIR is faster. Although neither Raman nor FTIR is used for typing metals, these can often be categorized (if not explicitly typed) by their highly opaque nature. Certain embodiments include removal of the filter grid (or transfer without removal) to allow the user to transfer it to a system more suitable for metals—e.g. laser induced breakdown spectroscopy (LIBS) or SEM EDS analysis. In certain embodiments, a custom library of materials can be built by using a database of spectra or by manually measuring materials that are possible particle producers (such as pump parts, syringe stoppers, glass vials, excipient, silicone oil, the pharmaceutical, etc.) and storing their spectra. Preselecting a library of materials will dramatically increase the accuracy of spectroscopy results and vastly improve user experience and convenience.

Advantageously, a commercial chip according to embodiments described herein are manufacturable, scalable (e.g. $5 cost or less at volume) and can capture the size range of interest (>0.5 μm). In certain embodiments, throughput is 30 minutes per sample with >90% of particles tracked and identified. In certain embodiments, software is used to automate system operation and data processing. In certain embodiments, there is >90%, >95%, >99% or 100% agreement with conventional particle counting instruments.

Figure 1C:
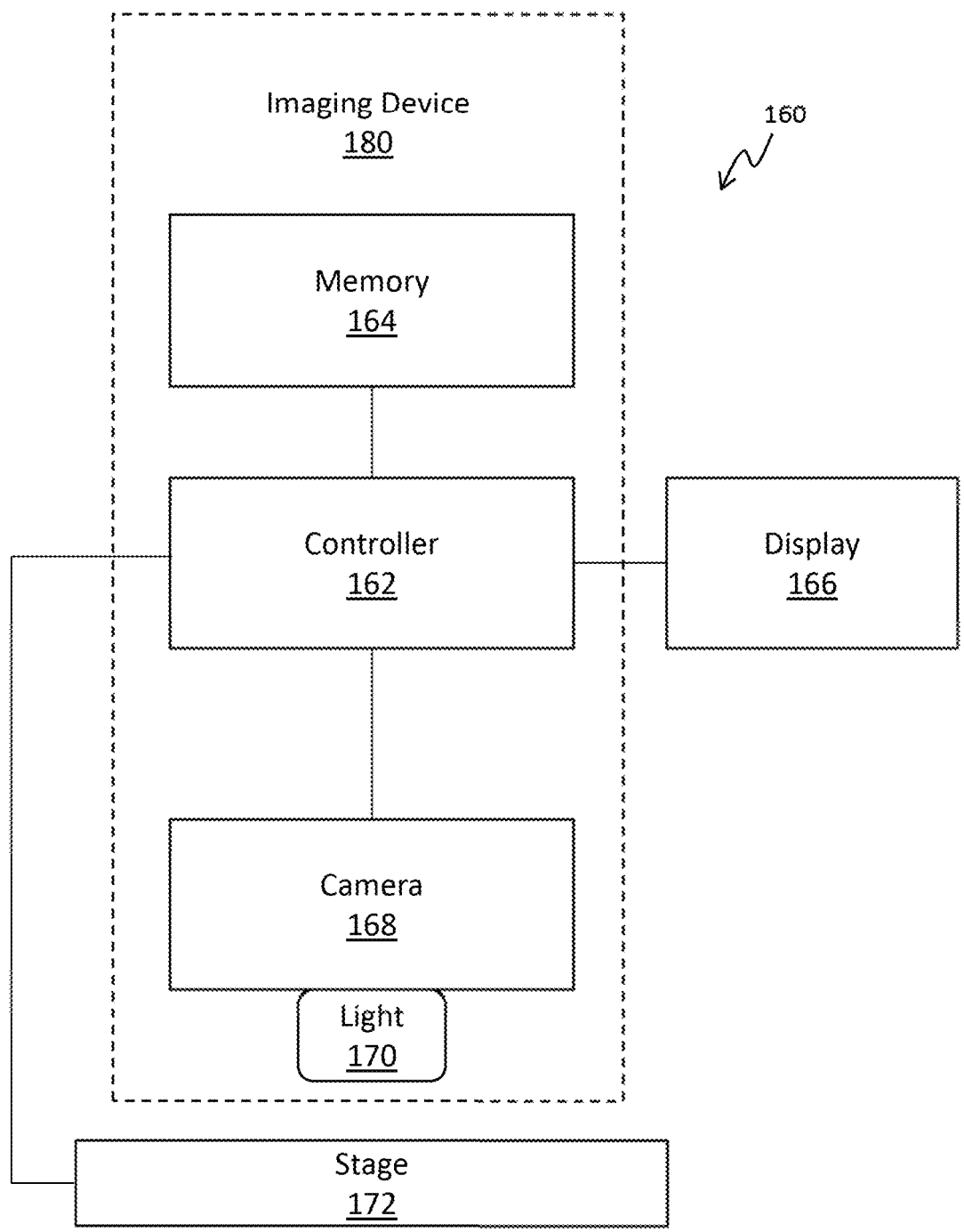
FIG. 1C is a block diagram of a system for characterizing particulates in a fluid sample according to one embodiment.

With reference now to FIG. 1C, a block diagram of a system 160 for characterizing particulates in a fluid sample is shown. The system includes an imaging device 180 which can include one or more cameras 168, a light 170 for illuminating fluid samples and particulates (such as the ring light described herein), a controller 162 for controlling the camera 168 and light 170, and a memory module that communicates with the controller 162. The controller 162 can process images as described in the various embodiment. As understood by those having ordinary skill in the art, the controller 162, memory 164, camera 168 and light 170 can communicate via a number of configurations, and communication can be wired or wireless between system components. Generally, the imaging device 180 in certain embodiments includes the camera 168 and a controller 162 in any configuration for communication with one another, such that the imaging device 180 can capture and process images, and output results of particulate characterization for the user, such as to a display 166. The controller 162 can be integrated into the camera 168, located elsewhere in the system 160 or located remotely and otherwise communicating with the camera 168, the light 170 and other system 160 components. The controller can connect to a display 166 for communicating results and images to the user. The display 166 can be touch screen for providing user input into the system 160. The controller 162 can also communicate with a stage 172 for which the fluid sample or chip is placed on. In certain embodiments, the stage moves to center the sample under the light and camera. The stage can also have illumination elements controlled by the controller.

Figure 2A:
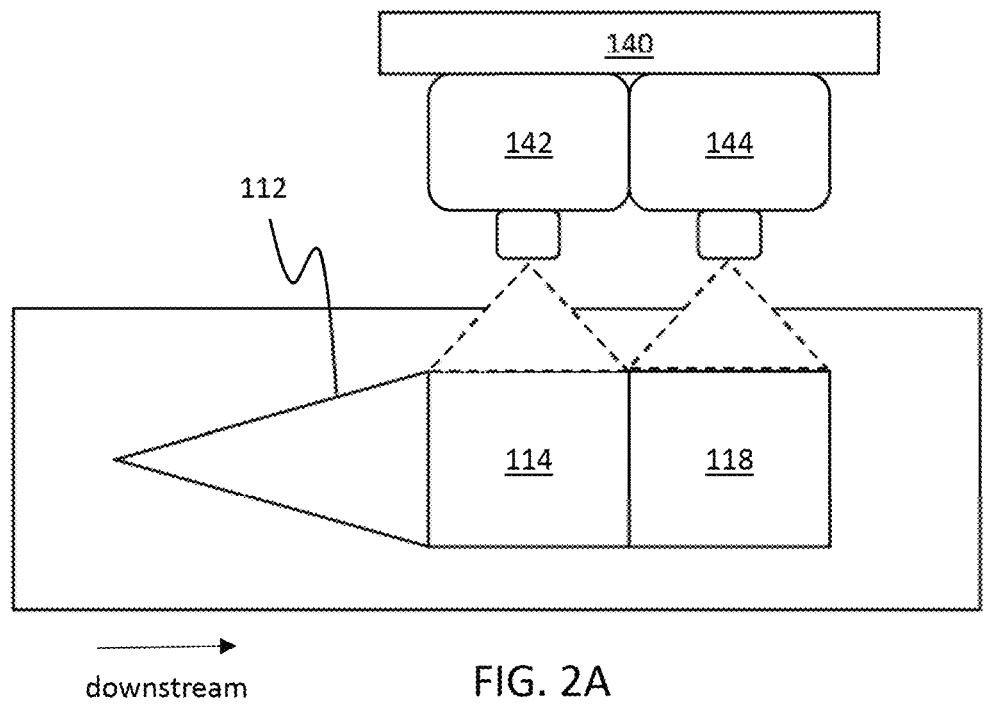
FIG. 2A is a diagram of a system for characterizing particulates in a fluid sample according to one embodiment where the imaging device has two cameras and an imaging region separate from the filter.
Figure 2B:
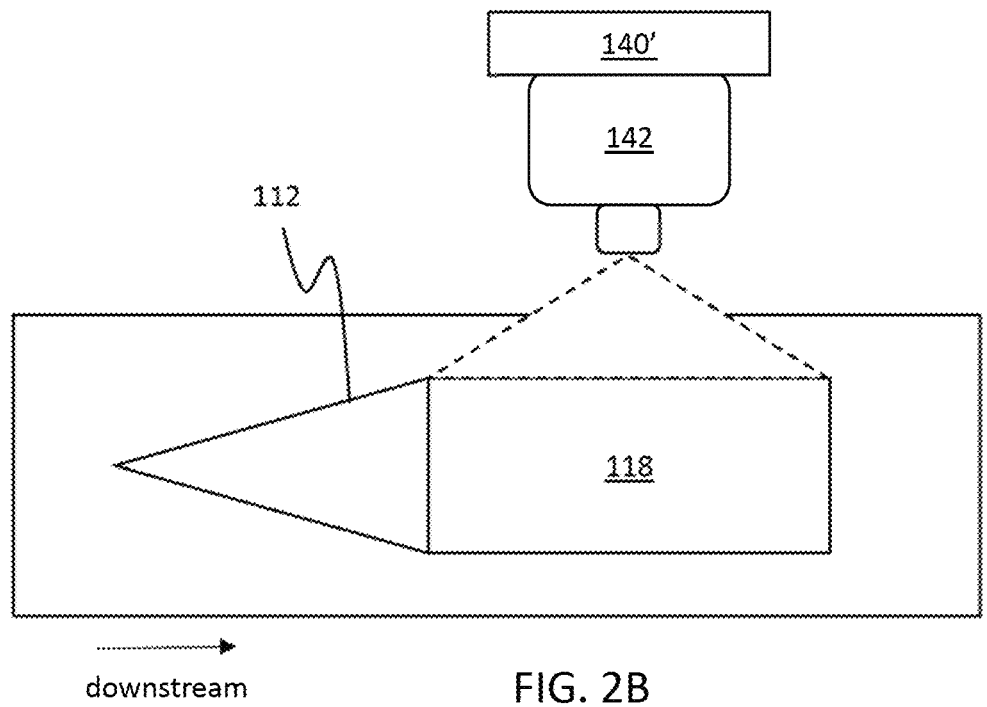
FIG. 2B is a diagram of a system for characterizing particulates in a fluid sample according to one embodiment where the imaging device has one camera and a single imaging/filter region.

With reference to FIG. 2A, the imaging device 140 can include a first and second camera 142, 144 for imaging the imaging region 114 and the filter 118 respectively. In one embodiment, a single camera is used to image both regions. In certain embodiments, more than one camera is used to image each respective region. In one embodiment, a single camera is used to image the filter and fluid samples are provided directly onto the filter. As shown specifically in FIG. 2B, the imaging device 140' can use a single camera 142 for embodiments where the imaging region and the filter are the same region 118, such as when the system is only concerned with imaging particles trapped on the filter. This can be the case for example when fluid samples are pipetted directly onto a filter (e.g. see FIG. 1B). It will be understood by those having ordinary still in the art that the imaging device can process images for characterizing particulates via an integrated controller or one or more separate controllers communicating with the imaging device and the system. Memory modules for storing software and images, input/output components and other components normally found in similar types of systems are also present and can be configured in any way as would be apparent to those having ordinary skill in the art. In certain embodiments, quantitative high fidelity particle imaging can be accomplished directly on the filter rather than during flow. In certain embodiments, observation with a microscope allows for particle imaging for size and morphology characterization prior to immobilization on filter, which would allow higher confidence size measurements and potentially 3D reconstructions of particle morphology.

Figure 3A:
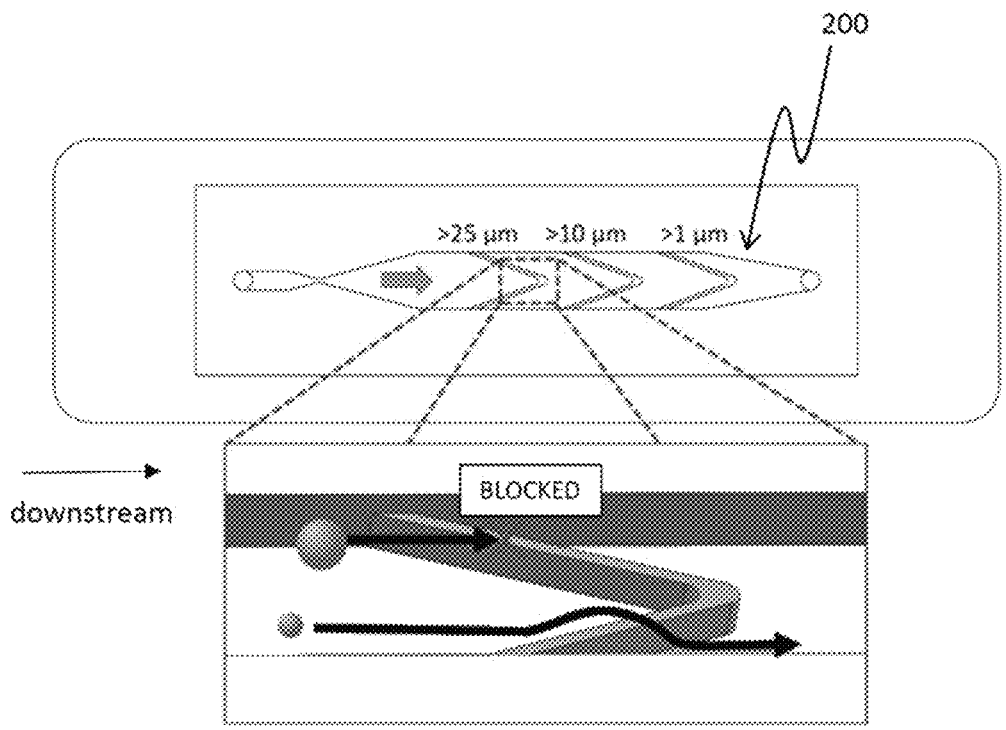
FIGS. 3A and 3B are diagrams of a channel having weir filters according to one embodiment.
Figure 3B:
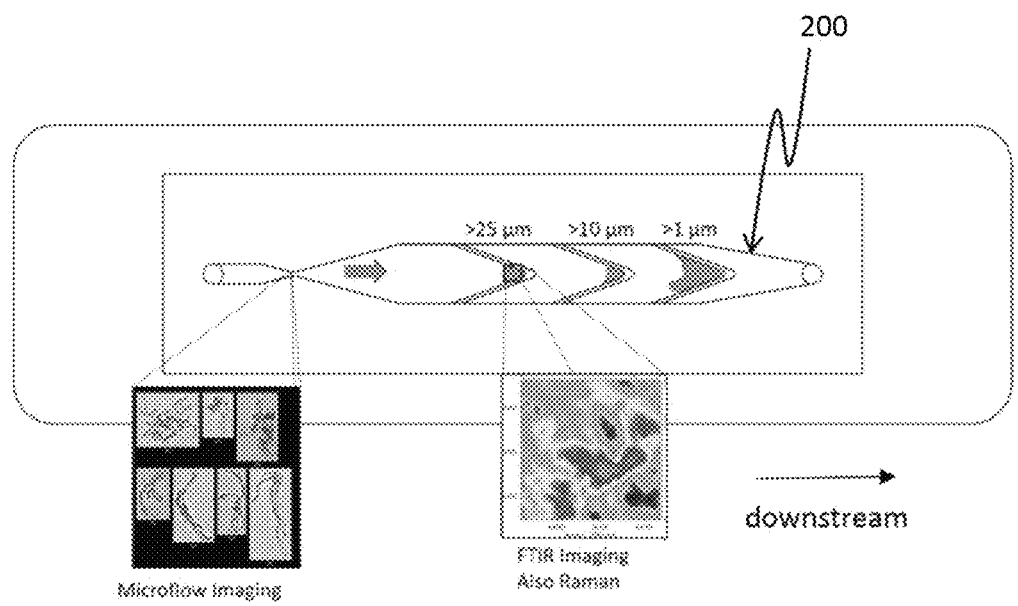

In certain embodiments, alternate filter types are used. With reference now to FIGS. 3A and 3B, in one embodiment, a weir filter 200 can also be used to capture particles instead of the microporous grid. These filters 200 are in-line with the channel and can be used to pack particles into a much denser pack, allowing for higher throughput spectroscopy (see FIG. 3B). In one embodiment, there are multiple weir filters in series that get progressively smaller the further downstream. The shape of the weir filter can vary. In one example, to increase surface area of the gap, rather than extending the weir straight across the channel in a line, the weir is formed into a different shape, for example a 'V', 'U' or serpentine. In one embodiment, a crude estimate of particle counts or mass can be made by measuring the area of the packed mass of particles and combining this with the weir type and channel depth.

In certain embodiments, particle size-based sorting can be used upstream so that particles of a certain size land on certain parts of the filter or can pass through the appropriate weirs more easily. For example, a particle sorter can arrange it so the larger particles are positioned towards the left with respect to the direction of flow and smaller particles move towards the right. In this way, when particles land on the grid filter they can be easily quantified. In the case of the weir filter, large particles and small particles, when so sorted, will not be in the same fluid stream line. This prevents a circumstance where the larger particles get captured in a weir and obstruct the smaller particles which ideally would escape the large particle wier and get captured further downstream. In certain embodiments, micromesh allows repeatable flow-rate vs pressure dependence through low variability in flow resistance across devices, improving run to run consistency.

In certain embodiments, the system is made from inorganic materials to allow for harsh chemical treatment/ cleaning (e.g. with Piranha/sulfuric acid/hydrogen peroxide, bleach) for subsequent re-use. In certain embodiments, wafer grade materials can be chosen such that extreme flatness of device permits large area scanning without the need to refocus optics for imaging, or excitation/collection of spectroscopic signals. In certain embodiments, micropatterned fiduciary marks can be patterned onto surface for automated imaging steps. For example, a fiducial mark can indicate where image or spectroscopy scanning begins. Another example is that multiple marks in different locations across device can be imaged for the purpose of quantifying device tilt and bow. In certain embodiments, micropatterning of devices allows for addition of alignment features (e.g. holes for guide pins) etched right into the device material for precise alignment in assemblies (e.g. flow assembly, imaging assembly) or stacking devices in series.

Thus, compared to conventional devices, embodiments described herein have several advantages. With respect to particle identification, by imaging the particles as they land on the filter, each particle's spectra can be directly tied to its image, giving it a precise identity. This feature is highly desirable to scientists. There are also may filtration benefits. Lithographically defined pores have excellent qualities. They have a large amount of open area which greatly increases volumetric flow rate while reducing the pressure required compared to traditional filters. The result is a much gentler filtration and reduced chance of flexible particles being pushed through the filter. In certain embodiments they are made of materials that are ideal for spectroscopy and the nature of the tightly packed grid dramatically shortens the spectroscopic analysis time. Embodiments described herein overcome shortcomings of standard filtration. Traditional filtration microscopy is perceived as less quantitative than microflow imaging because particles can be pushed through the filter or difficult to image once on the solid substrate. However, by combining the two techniques, the quantitative counting of MFI can be leveraged while taking advantage of the typing capabilities of filter spectroscopy. Regarding flow control, as particles accumulate on standard filters, the pressure can build up and force deformable particles through the filter. The chip according to embodiments described herein allows dynamic control of fluid pressure on the membrane (e.g. by reducing flow rate) to keep the stress on each captured particle below a dangerous threshold. Flow control can also detect filter blockage. High throughput spectroscopy is another important advantage. Traditional IR and Raman microscopy requires scanning a point source and single element detector to generate a compositional map. Arrayed detectors used in IR imaging offer significantly higher throughput through parallel acquisitions of spectra. In addition, sample banking is improved according to the various embodiments: The use of disposable chips allows each sample to be banked should the need arise for future, deeper investigation or backup to FDA QC record keeping. Chips can also be "opened" and analyzed with electron microscopy or LIBS.

Figure 4:
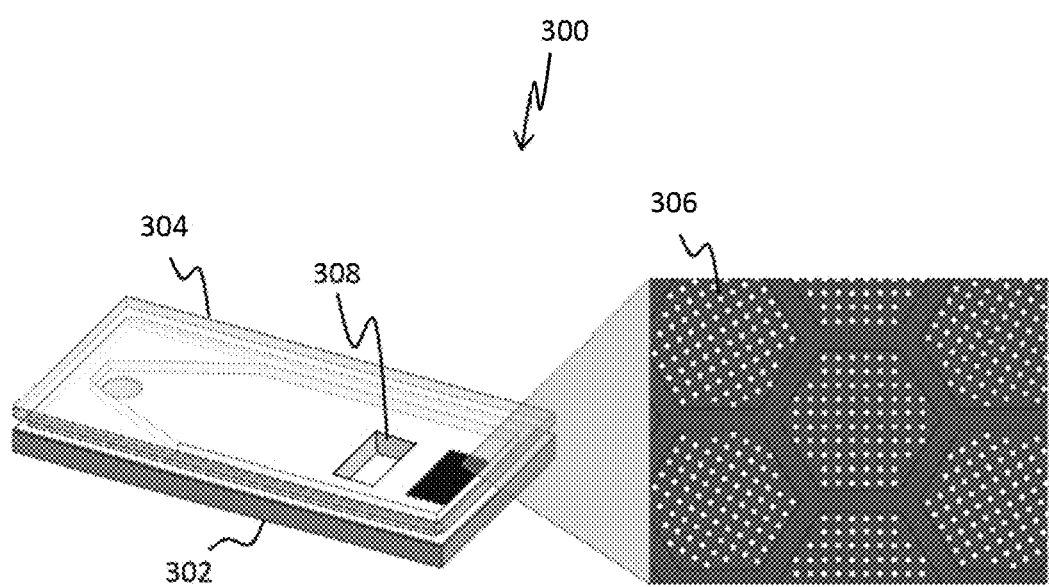
FIG. 4 is a perspective and partially magnified view of a filter chip according to one embodiment.
Figure 5:
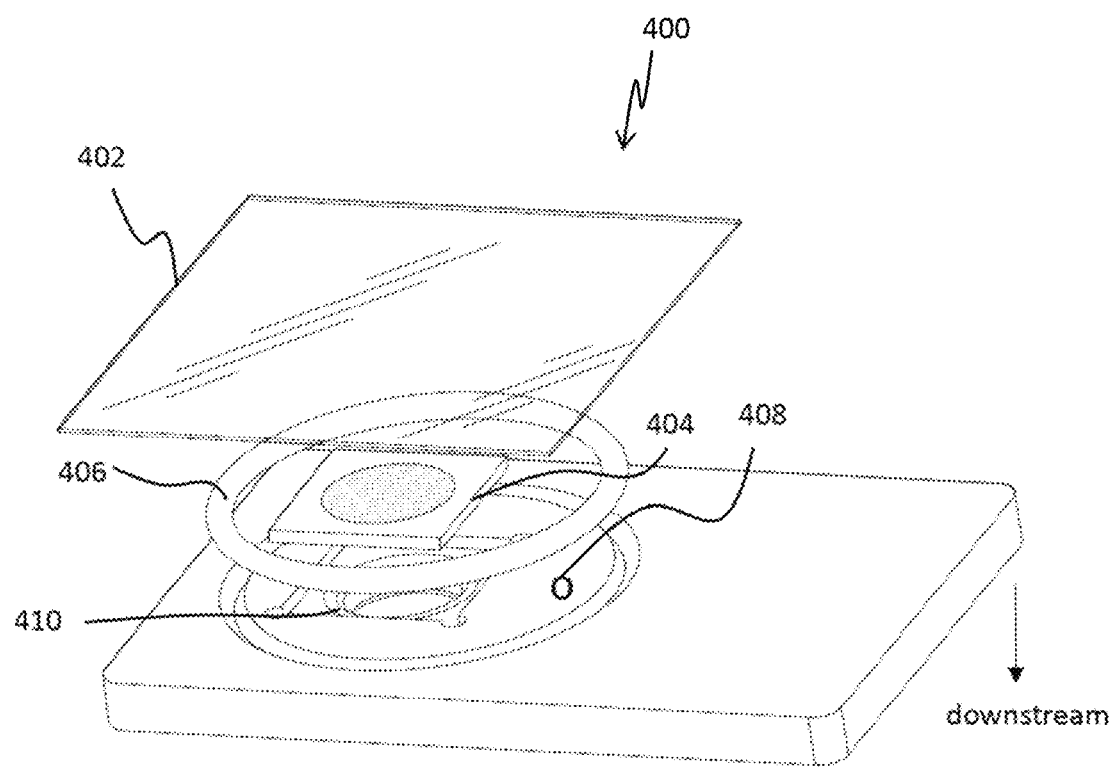
FIG. 5 is a perspective view of a compact housing that can allow for imaging directly on the filter according to one embodiment.

With reference now to FIG. 4, in one embodiment, to fabricate a filter chip 300, standard microfabrication techniques conventionally used for cell separation devices are utilized (see e.g. Earhart C M, Wilson R J, White R L, Pourmand, N, Wang S X. Microfabricated magnetic sifter for high-throughput and high-gradient magnetic separation J. Mag. Mag. Mat. 2009 May 1; 321(10):1436-39; and Earhart C M, Hughes C E, Gaster R S, Ooi C C, Wilson R J, Zhou L Y, et al. Isolation and mutational analysis of circulating tumor cells from lung cancer patients with magnetic sifters and biochips. Lab Chip. 2014 Jan. 7; 14(1):78-88.). In one embodiment, a double polished silicon wafer 302 is coated with a 3 micron thick layer of silicon dioxide 304, in which micro-pores 306 will be patterned by optical lithography. These pores 306 will be opened for fluid flow by etching a honey-comb structure through the backside, terminating at the oxide layer, by deep Reactive Ion Etching. Larger holes for fluidic and illumination access can also be etched in this step. In one embodiment, the filters are 1×2 cm rectangular dies with a patterned filter area of 2×4 mm, containing 240 hexagonal arrays with 300-1500 pores per array, yielding 72,000-360,000 pores per device depending on pore size (2-5 um) and spacing. In one embodiment, the filter capacity is determined sufficiently high such that if a sample contains the particle concentration limit stated in the Pharmacopeial Convention (6000 particles/sample), the fluid resistance will change by less than 10%, assuming 100% of particles are trapped and one particle occupies each pore. Adjacent to the patterned pore area, separated by 1.5 mm, is a 2×4 mm oxide window 308, through which illumination will be provided for microflow imaging. Both regions have sized to fit in the field of view provided by using a 4× objective and a camera with sensor size of 22.5×16.9 mm. One issue addressed by this design is to ensure that the illumination membrane will be mechanically stable. As a risk mitigation step, according to one embodiment, a design with a honeycomb support structure is implemented. Although it may prove more difficult to image particles while directly over the support structure, the high sampling frequency should enable imaging of a particle while over the oxide membrane as it traverses the imaging region. As shown in FIG. 5, a compact housing can allow for imaging directly on the filter. In one embodiment, an inlet can 408 and outlet 410 are in fluid communication and the outlet 410 is covered by a filter 404. The filter 404 is surrounded by an o-ring 406 and covered by a cover slip 402. Accordingly, the filter 404 can be imaged directly for particle morphology as it is built into a simple housing.

Figure 6A:
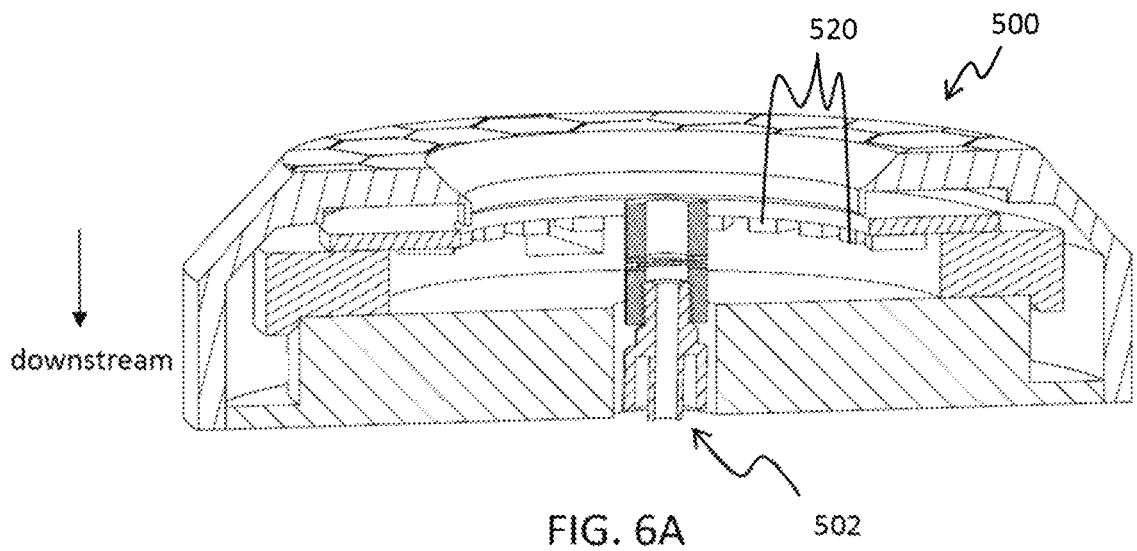
FIG. 6A is a filter stack within a light ring.
Figure 6B:
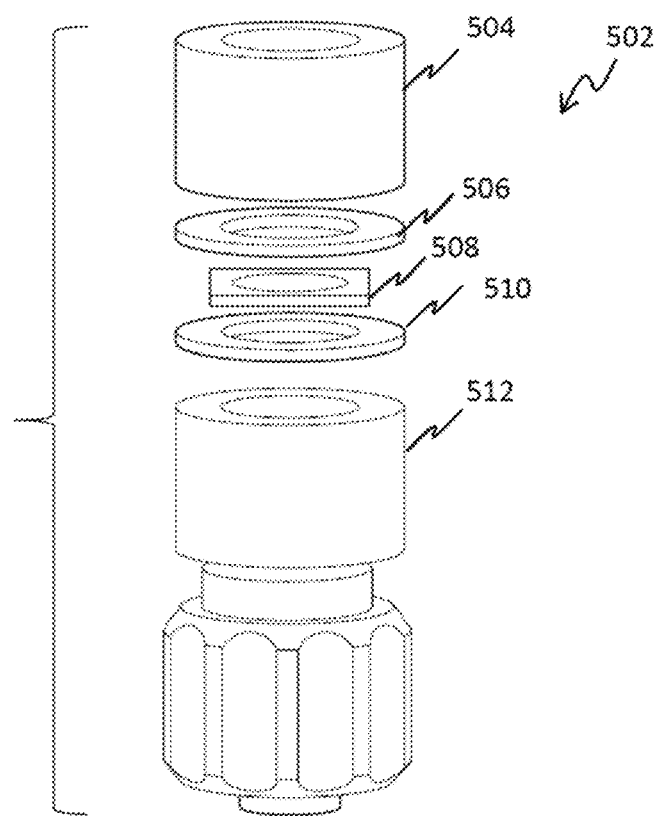
FIG. 6B is an exploded view of the filter stack according to one embodiment.

With reference now to FIGS. 6A and 6B, a method for illumination is shown according to one embodiment. A filter stack 502 includes an opaque top ring 504, and transparent or translucent double sided tape 506, a microfilter chip 508, double sided tape 510 and a bottom ring 512. The assembled filter stack 502 is configured to fit within the ring light assembly 500, which includes multiple lights (e.g. LEDs) pointed inwards towards the chip 508. The quality of particle imaging on the microfilter chip 508 is dramatically affected by the method of illumination. An illumination method where light is directed towards the particle in-plane with the chip surface provides excellent illumination of the particles while preventing excessive illumination of the pores. Illumination of the pores can cause difficulty when processing the images since they can be confused with particles. To achieve this effective illumination, a ring light 500 of LEDs 520 was developed where the LEDs 520 point inward radially. The ring light 500 is positioned such that the LEDs 520 are in-plane with the top of the microfilter chip 508. This method is similar to a dark field illumination where illumination comes from the side and object edges are appear bright. However true dark field illumination is not in-plane with the image. In the case of the microfilter chip 508, the pore edges are also illuminated in dark field which is not desired.

In most filter applications, the filter is placed in a holder that will block or distort illumination that comes from the side. A filter holder has been developed that uses a transparent or translucent tape layer that allows light to travel through this layer to illuminate the sample in an effective way. The construction of the consumable is as follows. A ring-shaped double sided tape adhesive 506 is placed on top of the microfilter chip 508. The tape adhesive 506 has a gap in the center to allow the liquid to pass through the filter part of the chip 508. A ring-shaped top part 504, currently made of opaque acrylic is placed on top of the double sided tape 506 so that the tape 506 is sandwiched between the chip 508 and the top acrylic ring 504. This forms a reservoir on top of the microfilter chip 508 which is fluid tight. Liquid sample can be dispensed into the reservoir and vacuumed through. After vacuuming, the top surface of the microfilter chip 508 can be illuminated through the tape layer. An opaque top ring was found to be superior to a clear or translucent ring. This is because confining light into the tape layer ensures more planar light reaches the sample.

In one embodiment, high accuracy classification of particles imaged on a filter can be achieved by applying machine learning algorithms to data collected on the particles. Data can include images, spectroscopic or fluorescence signals or spectra, or features extracted from images, spectroscopic or fluorescent signals or spectra through image processing, signal processing, or an unsupervised learning platform. The data can be analyzed by a single or combination of machine learning algorithms, for example, random forest, boosting, or artificial neural networks, to generate a predictive model. A training set of data collected on particles of known identity is used to build the predictive model, which can then be applied to unknown particles for typing or classification. Classification information can include particle type (e.g. protein, glass, hybrid materials) or sub-types (type of glass, metal, or protein). Classification can also include aggregation state or likely cause of aggregation for protein particles. In one embodiment, the machine learning algorithm is a boosting algorithm. In one embodiment the machine learning algorithm uses neural networks. In one embodiment the machine learning algorithm uses convolutional neural networks. Machine learning algorithms can also be applied to data to produce a continuous output instead of or in addition to classification; for example, degree of protein aggregation, denaturation, or crystallization for protein aggregates.

In one embodiment, high vacuum pressure (i.e. low chamber pressure below the chip) has the advantage of driving fluid quickly through the filter or membrane, reducing overall processing time. However, high vacuum pressure also runs the danger of driving delicate particles through the membrane that would be desirable to capture instead. In order to drive fluid through the membrane, a breakthrough pressure must be achieved. The breakthrough pressure is often quite high in order to overcome capillary forces that may develop at the filter pores. Once flow is established, a different vacuum pressure, often lower in strength, can be applied. In order to reduce this breakthrough pressure and avoid the possibility of driving particles through the filter pores, a variety of thin surface treatments may be employed to increase the hydrophilicity of the filter surfaces. Examples of these treatments are the use of bovine serum albumin, hydrophilic silanes that can be vapor deposited, hydrophilic thiols that can self assemble on gold surfaces of the membrane, and poloxamer pluronic F-68.

In one embodiment, precise characterization of particles using texture, fluorescent intensity, and morphology requires accurate measurement of the intensity of each particle. Traditional imaging of particles is done by taking a single image and minimizing the number of saturated pixels, this is known as a standard-dynamic-range imaging (SDR). When working with particle populations that have order of magnitude size differences the information collected using SDR imaging requires that the intensity data from small particles is very low and may even be indistinguishable from the background of the image. High-Dynamic-Range imaging (HDR) uses computer algorithms to merge many SDR images taken at exposure times ranging many orders of magnitude into a single high bit depth (16+) Image that contains the full dynamic range of the image. Utilization of HDR imaging results in Images with a significantly larger range of luminance levels than can be achieved using traditional methods and allows for better characterization of particles.

In one embodiment, each particle analyzed will contain a unique intensity map of the particle that can describe the surface of the particle. The surface properties of a particle are unique to the particle type and in some cases sub-type of the particle. These surface properties can be used in conjunction with other properties to classify particles. Information about the surface of the particle can be extracted using mathematical algorithms such as the gray-level co-occurrence matrix, local binary partition, and edge density and direction.

In one embodiment, droplets of liquid that adhere to the back of the filter (the non-imaging side) can disrupt the imaging by filling pores, entering back into the top of the chip and obscuring particles and particle edges. Several methods have been employed to remove this liquid from the chip. In one embodiment, the method is to vacuum the chip for a sufficient time using a vacuum source capable of high flow rate (at least 2 cubic feet per minute). In one embodiment, the method is to aim a flow of gas (preferably dry, like nitrogen gas) towards the top of the chip. In one embodiment, the method is to force pressurized gas through the surface rather than just aiming a flow of gas towards the surface as in the second method. This requires a seal between the gas source and the chip. In one embodiment, the method is to use a fan above or below the chip to drive air through the membrane. Using a fan below the surface is preferable since particles will be driven against the membrane and there is less chance of particles being blown off as in the case of the fan above the chip. In one embodiment, the method is to use a wicking material (such as a cellulose pad or glass fiber pad) and applying it to the bottom of the chip so that the liquid enters the wicking material.

Figure 7A:
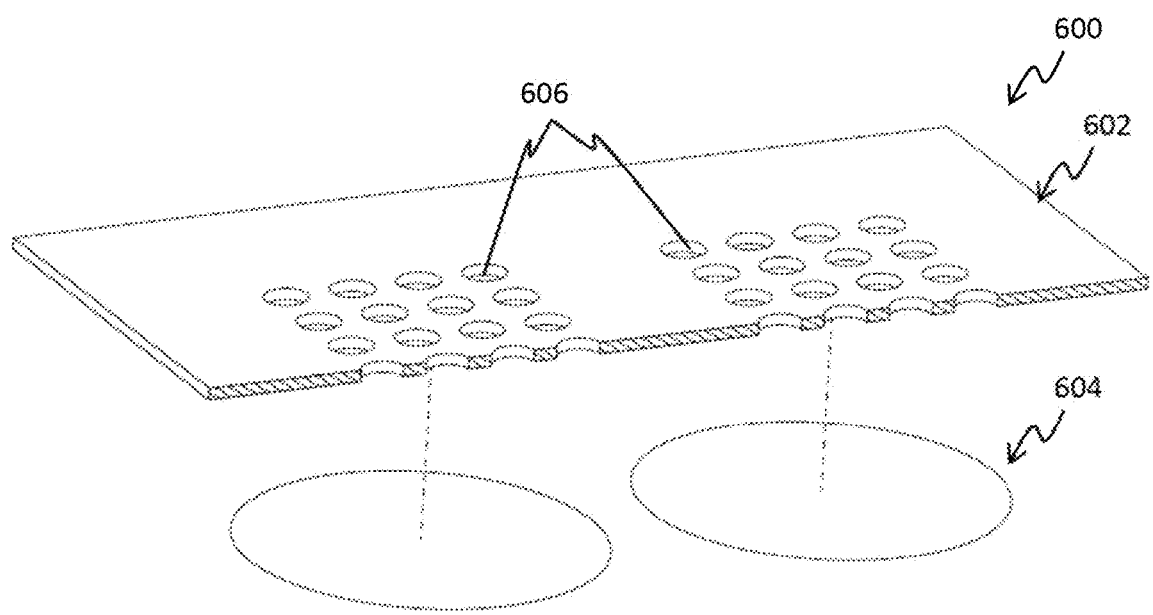
FIG. 7A is a perspective view diagram of a well plate and membrane.
Figure 7B:
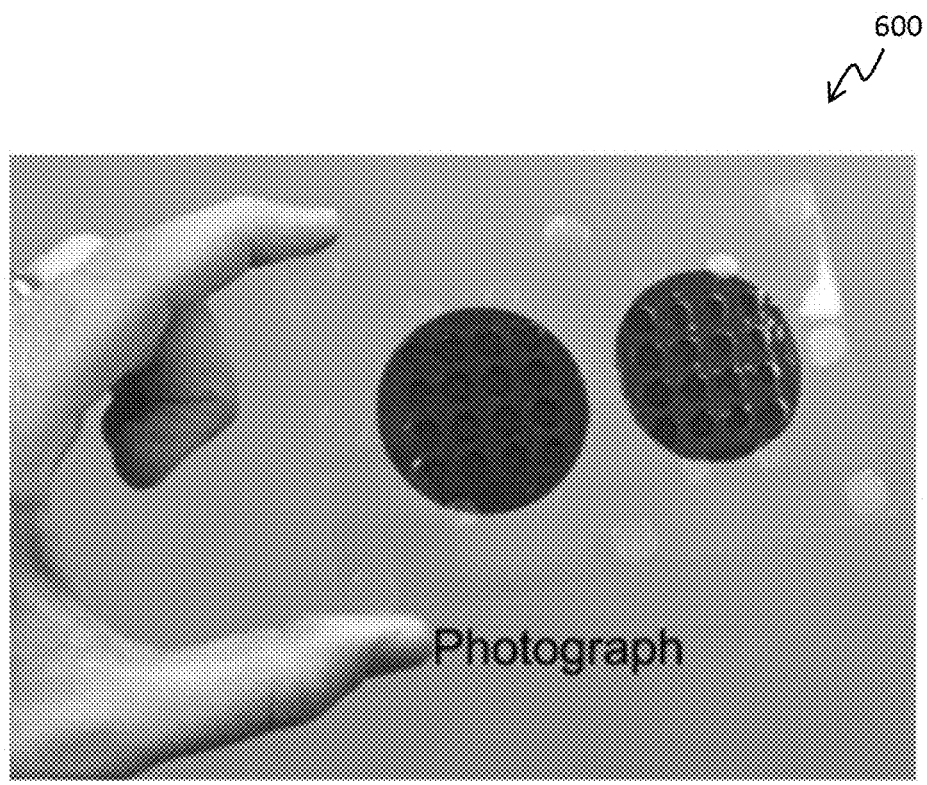
FIG. 7B is a photograph of an assembled well plate and membrane according to one embodiment.
Figure 7C:
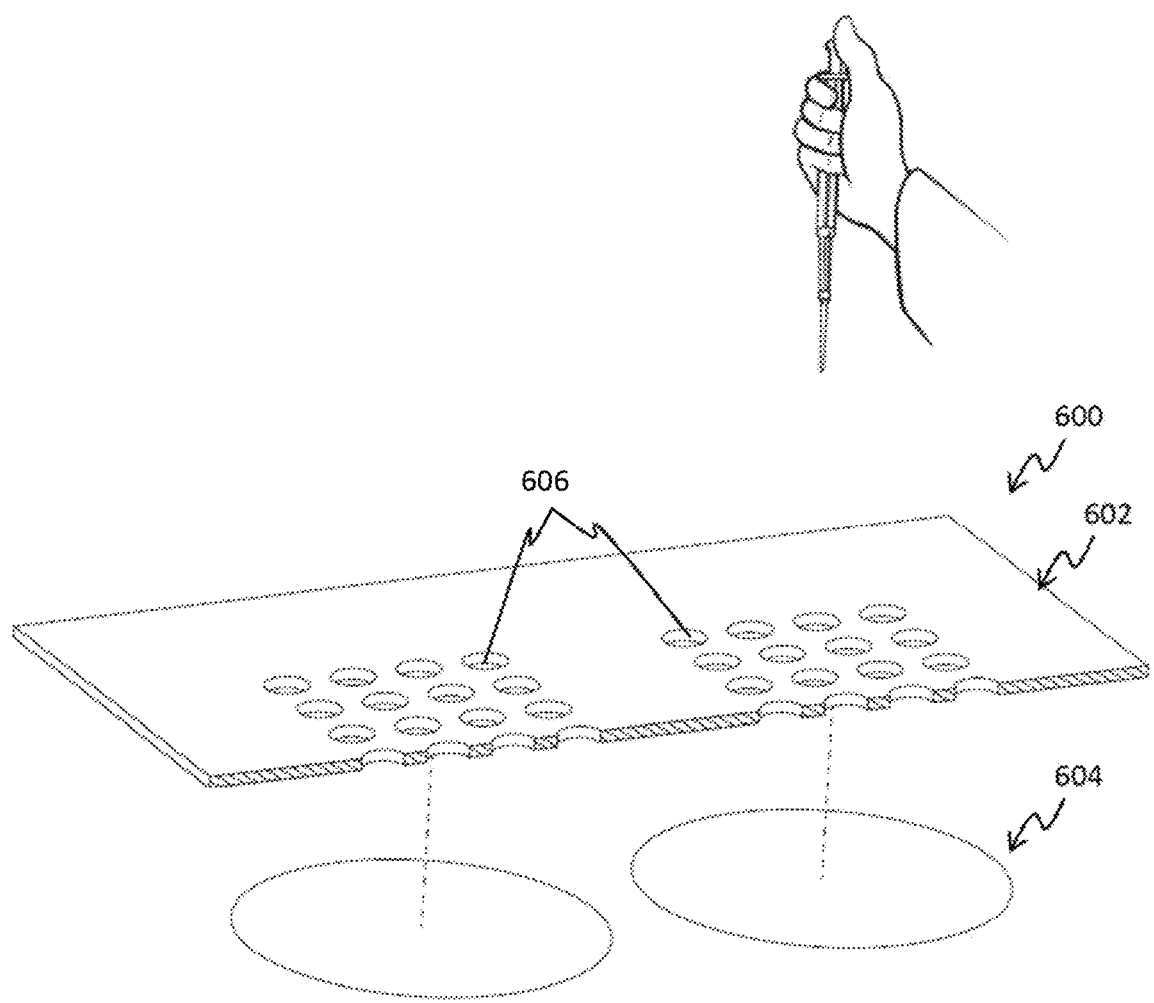
FIG. 7C is a perspective view diagram of a well plate and membrane with an illustration of a fluid sample being inserted into each well with a pipette.

With reference now to FIGS. 7A and 7B, in one embodiment, a disposable well plate 600 includes multiple fluid channels or wells 606 for fluid samples. The well plate can include multiple wells, including 32-96 wells, up to 384 wells, up to 1536 wells or more. In one embodiment, the disposable well plate 600 consists of two layers 602, 604. A top layer 602 which is a polycarbonate (transparent) plate with holes 606, and a bottom porous membrane material layer 604 which is thermally bonded to the polycarbonate 602. The pore size of the porous membrane (also polycarbonate) is currently 400 nm and is commercially available. In the one embodiment and as shown in FIGS. 7A and 7B, two discs, each 47 mm in diameter are used. Two discs are assembled on the plate 600 to form 32 sample wells 606. Membranes are bonded to the plate using a thermal bonding technique. In one embodiment, the wells form a circular pattern to fit within the ring light described herein. The fluid sample can be introduced into each well by pipette, as illustrated in FIG. 7C

Figure 8:
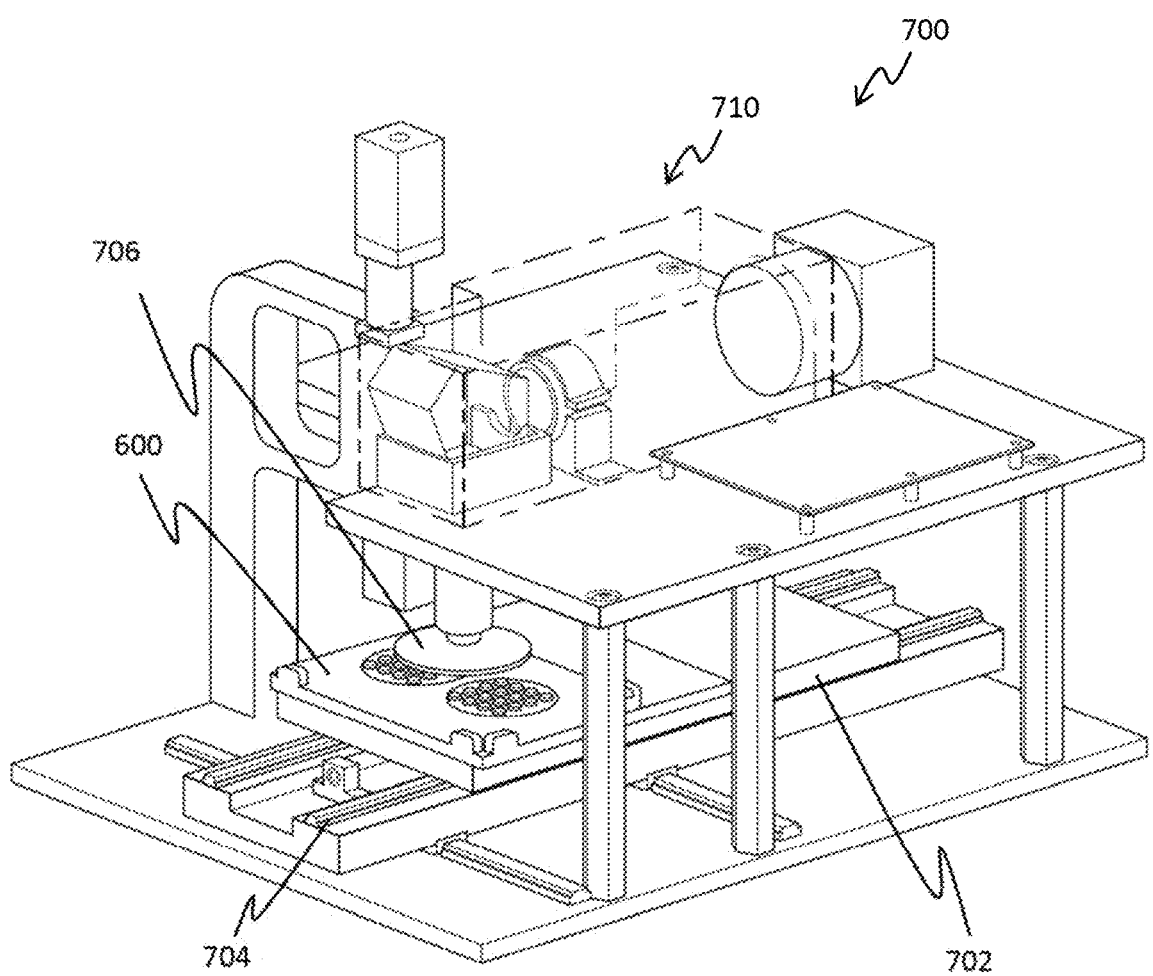
FIG. 8 is a perspective view of a well plate imaging system according to one embodiment.

A robotic apparatus for imaging the well plate is shown with reference now to FIG. 8, according to one embodiment. The well plate 600 sits on a microscope stage 702 that further sits on a track system 704 that can manipulate which well or set of wells is positioned under the ring light 706. Imaging and processing components 710 are configured above the deck for imaging the fluid samples and particulates in the wells. Generally, the instrument is a robotic microscope with a camera and illumination method as described herein. In one embodiment, a 32 well plate 600 is placed on the microscope stage 702 and the microscope automatically positions wells under the objective lens for imaging. Large area (e.g. ⅔ inch) camera sensors can be utilized for imaging, which allows good images with low magnification lenses. This helps fit a large area of the membrane in a single image, a configuration that is designed for speed without undue sacrifice of imaging performance.

In one embodiment, well plates are loaded into the instrument 700 and images are taken of the plate to generate at least one "background" image. In certain embodiments, multiple background images are actually taken. The background image can be generated in certain embodiments based on multiple averages, multiple exposure settings, multiple illumination methods, multiple focus heights, and comparable techniques known in the art. There are likely some particles or deformities on the membrane present before the introduction of the sample that should be accounted for and in general, there are always background features on the membranes that must be accounted for. These can be scratches, texture, particles from manufacturing or from the air, etc. In order to get an accurate particle count from a sample, these background features should be taken into consideration. A "before image" is acquired for this purpose and analyzed before samples are loaded onto the membrane and vacuumed. The "before" and "after" images are processed using a variety of algorithms to get accurate particle data.

Next, the user can load plates with fluid by pipetting samples into the wells. Then, plates are placed on a vacuum manifold and vacuum is applied so that only particles are left behind on the membranes (no fluid). Next, the user can load plate into instrument for imaging and analysis. The instrument then images each well under 1 or more optical conditions (eg. bright field, darkfield, fluorescence, different exposures). In certain embodiments, a composite image is formed using a combination of bright field and oblique angle illumination. Combining bright field with side illumination yields excellent differentiation between particles of different materials. In certain embodiments, through-plate oblique illumination is used. Next, the instrument moves to the well, focuses using a software technique, and acquires images using one or more techniques. For each technique a multi exposure stack of images can be taken. These stacks can then combined into a single high dynamic range image. If the whole membrane doesn't fit on one exposure, multiple areas are imaged separately as described above and combined into a single stitched image. In certain embodiments, a focus fusion and averaging technique is utilized. The HDR image stack can be taken at many different heights and focus fused together. Also, every image can really be an averaged image consisting of 1 or more repeats at the same exposure. In certain embodiments, to do the focus fusion, each image needs to be registered to each other to account for slight movement between images. In the next step, the system then proceeds onto the next well. Images are analyzed using an image processing steps to isolate particles and identify which particles came from the sample and which were background particles from the before image. In certain embodiments, both images undergo heavy image processing and the before image is combined mathematically with the after image in such a way that the background texture and particles are eliminated. The instrument then outputs desired physical and chemical parameters, such as size+counts, morphological properties (e.g. aspect ratio) particle ID, brightness, opacity, a ratio of brightness between two different imaging modes, or other stability parameters. Next, the user can take out the plate and run additional chemistry for a new assay that is brought back to the instrument for conducting differential measurement (stability, solubility, activity assay). After particles are collected, they can be further analyzed by additional techniques (other assay, FTIR, EDX), etc. Advantageously, the plates capture the particles and present them in a nice way to these other instruments.

Figure 9A:
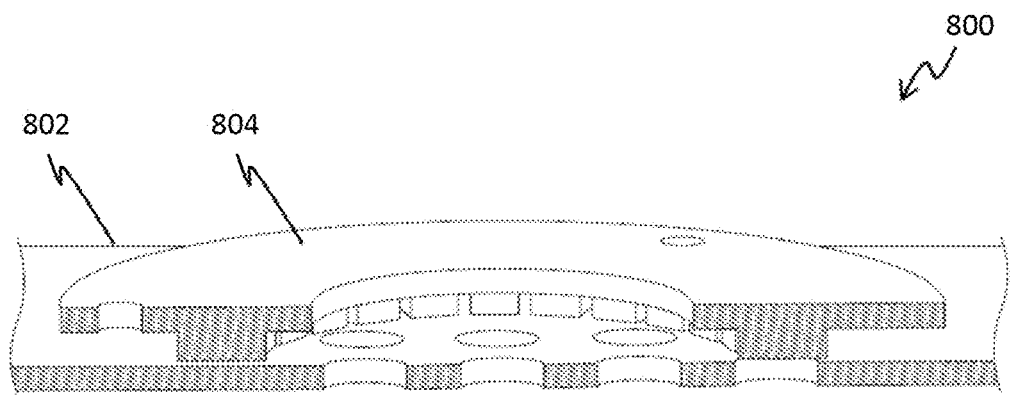
FIG. 9A is a cutaway view of a ring light on a well plate.
Figure 9B:
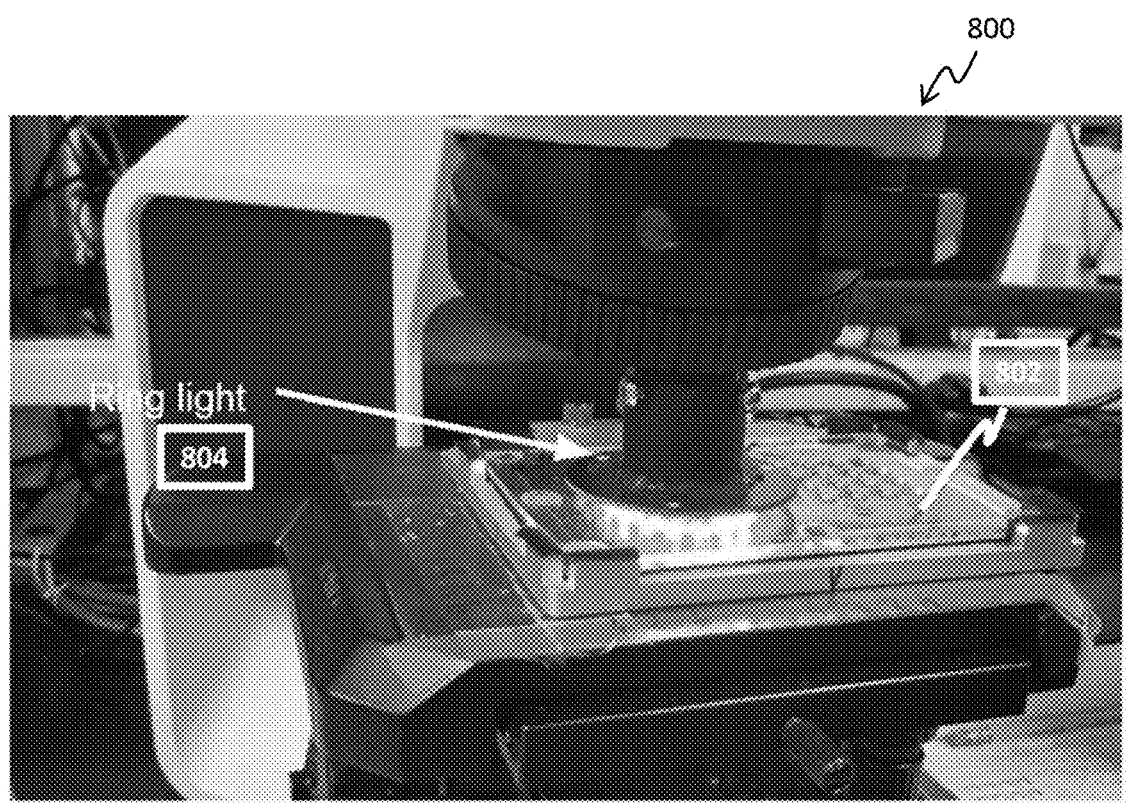
FIG. 9B is a photograph of a ring light on a well plate according to one embodiment.

As was the case with previous embodiments, a key to instrument advantage is the method of illuminating the particles on the membrane, which yields high signal to noise ratios. The objective is to illuminate the samples in such a way that the particles appear as bright as possible compared to the membrane, which forms the background of the images. The components involved in this method include an LED ring light, the consumable plate, and the membrane. The illumination source is an LED ring light, which illuminates particles at a very oblique angle, as shown in FIGS. 9A and 9B. The LED ring 804 uses surface mounted LEDs, which direct the light towards the center of the ring 804. The LEDs are placed as close to the membrane as possible so as to achieve the most oblique light possible. It is believed that this oblique angle causes the light to preferentially scatter off of the particles compared to the membrane surface. This results in increasing the particle signal to noise ratio. In some embodiments, the oblique angle is less than 17 degrees. In some embodiments, the oblique angle is less than 13 degrees. In certain embodiments, the system is configures to that the angle is coplanar with the surface. In one embodiment, the oblique angle is any non 90 degree angle relative to a flat plane of the filter. In one embodiment, the oblique angle is 30 degrees or less. In one embodiment, the oblique angle is 20 degrees or less. In one embodiment, the oblique angle is 17 degrees or less. In one embodiment, the oblique angle is 13 degrees or less.

In one embodiment, the light coming from the LEDs will interact with the plate before reaching the particles. In one embodiment, a transparent plate is utilized with polished walls that allow the light to enter and exit the plate with little scattering. In one embodiment, the plate is coated in a reflective film. Although the light cannot enter the bulk material of the plate in this case, the image quality is still high. This is likely due to the light entering a well and reflecting inside the well while maintaining the oblique angle.

In one embodiment, the bottom of the well has a smaller radius than the top of the well. When the objective lens of the imaging system is focused on the membrane, the top of the well is out of focus and can cause a bright blur that encroaches on the membrane imaging. This blur can obscure particles that are near the well wall. Therefore, by increasing the radius of the top of the well, the most out of focus elements are brought away from the membrane, allowing for a better image of the outside regions of the membrane.

In one embodiment, imaging is performed on bare membranes not attached to plates, which provides superior imaging but does not allow an easy way to deliver controlled aliquots of liquid. In one embodiment, the height of the wells is reduces, or the wells are otherwise defined using a very thin hydrophobic material that causes water droplets to bubble up and maintain their position. This thin material will in certain embodiments be superior for imaging.

The membranes can vary as well. In one embodiment, the membranes are black track etched membranes, e.g. such as those commercially available through EDM Millipore (Product name: Isopore black membranes. Product number HTBP04700). In one embodiment, the surface texture of the membranes is smooth. It is believed that the black material absorbs light that other membranes would scatter, and preferable membranes appears to have low surface roughness which also helps reduce background scatter. In one embodiment, the membrane plate is placed above a dark, non-reflective material such as felt which helps prevent light from reflecting back up through the membrane. Felt, which has a texture and can create bumps on the membrane if placed into direct contact, is separated from the membranes using a spacer/lip. In one embodiment, the track etched membranes can be modified as well, for example by coating them with a thin metallic layer such as gold, chromium or aluminum.

Figure 9C:
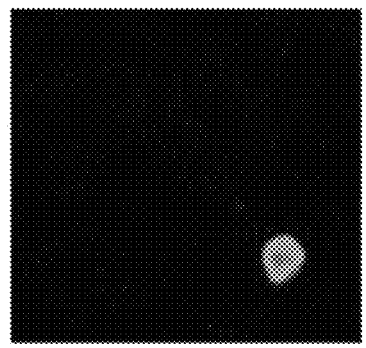
FIG. 9C is a side illumination image and a FIG. 9D is a bright filed illumination image that were both used to create a composite image, as shown in FIG. 9E.
Figure 9D:
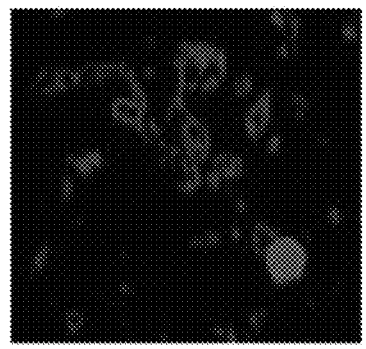
Figure 9E:
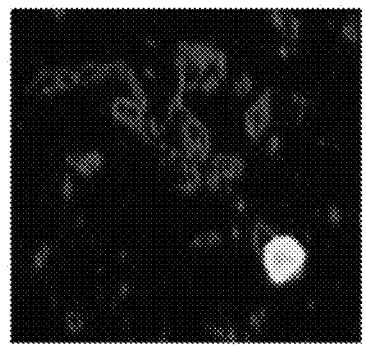

With dark field imaging, the membrane roughness scatters a lot and creates a very high intensity background, resulting in lower SNR. The instant method is superior to dark field illumination, and one possible explanation is that the illumination angle in the instant case is more oblique. In other words, as the angle of illumination becomes closer to parallel and co-planar with the membrane the better the particles will stand out from the membrane. In certain embodiments, with at least some protein aggregates, bright field provides a better illumination method then oblique angle side illumination. Thus, both methods can be used to create a composite image. A ratio of the two imaging techniques can according to the various embodiment be a powerful tool to count and differentiate types of particles. As shown in FIGS. 9C-9E, one or more side illumination images 9C can be combined with one or more bright field illumination images 9D to create a composite image 9E. The particles shown are on a membrane and are a mixture of polymeric particles and protein aggregates that have been generated by successive expansions and dilations of the liquid-air interface using a tube rotator. The first image shown in FIG. 9C is taken using the oblique light technique. In this image, the polymeric particle in the bottom right stands out sharply. No other particles are easily distinguished. In the second image shown in FIG. 9D, bright field illumination using a 455 nm center wavelength (blue) LED is applied to the particles. Bright field illumination in this example consists of light that is shined from above the sample through the objective lens. In FIG. 9D both the protein aggregates and the polymeric particle are visible. Though most particles are more easily distinguished from the background using side illumination, it is believed that these particular protein aggregates are more difficult to see due to their flexible and deformable nature which causes them to lie flat. FIG. 9E is a composite formed by blending the two modes of imaging shown in FIGS. 9C and 9D. The composite image shows how particles of different materials can appear very different under different illumination conditions and that this can be an effective way to characterize particles. The red particles are protein aggregates and the yellow one is a polymer. Thus, in one embodiment, particles are characterized by bright filed illumination only. In one embodiment, particles are characterized by side angle illumination only. In one embodiment, particles are identified by a combination of bright field and side angle illumination.

Figure 10A:
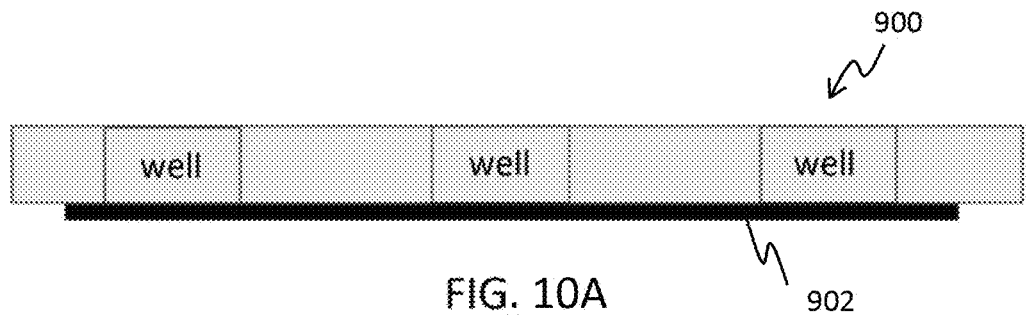
FIG. 10A is a diagram of a well plate constructed as a clear polycarbonate plate according to one embodiment.
Figure 10B:
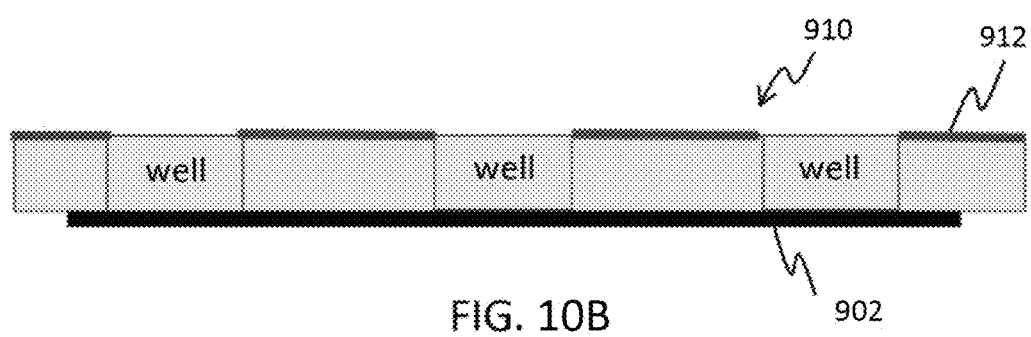
FIG. 10B is a diagram of a well plate covered by an opaque material according to one embodiment.
Figure 10C:
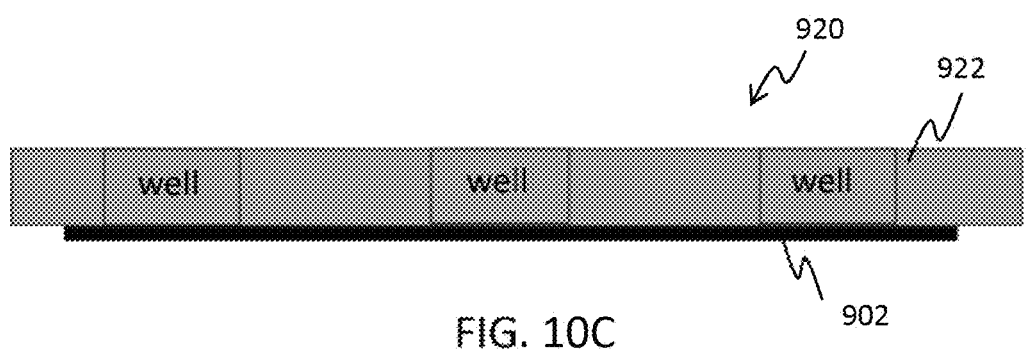
FIG. 10C is a diagram of a well plate that has been painted with a reflective coating according to one embodiment and FIG. 10D is a diagram of a well plate made from a bright white polycarbonate according to one embodiment.
Figure 10D:
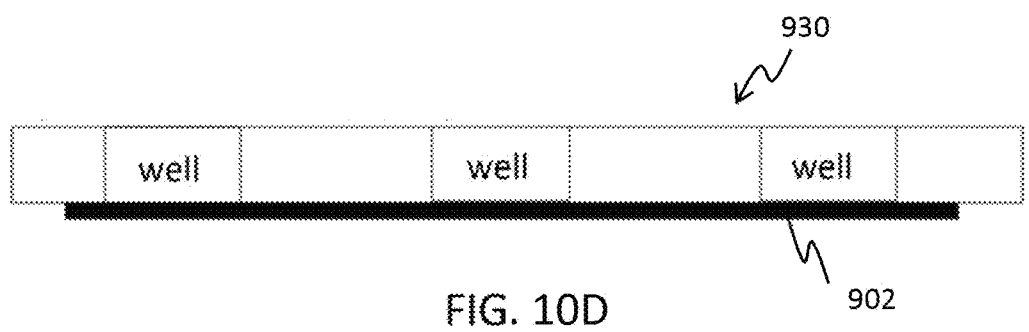

Different plate configurations can be utilized according to embodiments of the invention, and as shown in FIGS. 10A-10D. FIG. 10A shows a plate 900 and membrane 902 where the plate 900 is constructed as a clear polycarbonate plate. FIG. 10B shows a clear polycarbonate plate 910 and a membrane 902. In certain embodiments, the membrane is a polymer or metallica membrane. The top face of the plate 910 is covered by an opaque material 912. FIG. 10C shows a polycarbonate plate 920 and a membrane 902. The plate 920 has been painted with a reflective coating 922. FIG. 10D shows a bright white polycarbonate plate 930 and a membrane 902. The best images came from 1 and 3. The embodiment in FIG. 10A has particular advantages because it is believed the light enters through both the top face of the plate (and through neighbor well walls) and exits through the well walls of the well to be imaged. FIG. 10C has particular advantages because it is believed oblique light enters the well and is reflected off the walls till it reaches the surface, still traveling at an oblique angle.

Figure 11A:
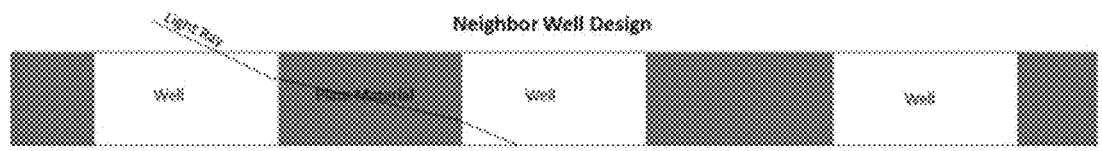
FIG. 11A is a diagram of a well plate having a neighbor wall design according to one embodiment.
Figure 11B:
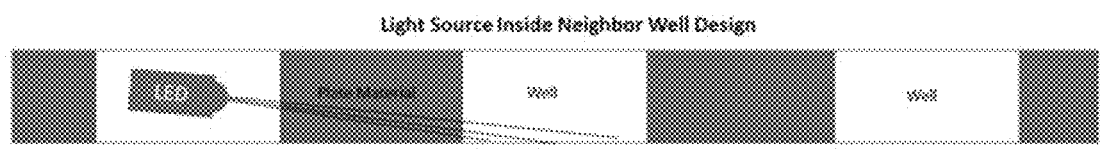
FIG. 11B is a diagram of a well plate having a light source inside the neighbor wall according to one embodiment.
Figure 11C:
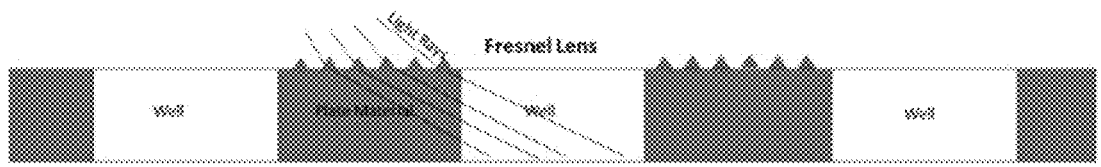
FIG. 11C is a diagram of a well plate having a Fresnel lens design according to one embodiment.
Figure 11D:
FIG. 11D is a diagram of a well plate having a lens design according to one embodiment.

With reference now to FIGS. 11A-11D, again a key advantage to embodiments described herein is that the illuminating light hits the particles at a very shallow angle which provides good contrast against the background material. The illuminating light in certain embodiments goes through plate material before interacting with the sample, thus the plate can be designed with materials and features that help to transmit the light. Right now, much of the light enters a well through its neighboring wells. In certain embodiments, optical features are incorporated into the plate material itself, including mirrors, lenses and prisms to transmit, focus and guide the light for improved contrast between particles (or other objects) and background and at higher light intensities (which allows camera exposures to be shorter, leading to time savings and performance improvement). In certain embodiments, the bulk of the plate material or the plate wall is designed to act as a light guide. In the examples shown, an optical feature can be incorporated into the plate material (see FIG. 11A), such as a material having a particular refractive index, a light source can be located in an adjacent well (see FIG. 11B), a surface of the plate material can have a particular non-linear geometry, such as a Fresnel lens (see FIG. 11C), and the plate material can have a lens design (see FIG. 11D).

Figure 12:
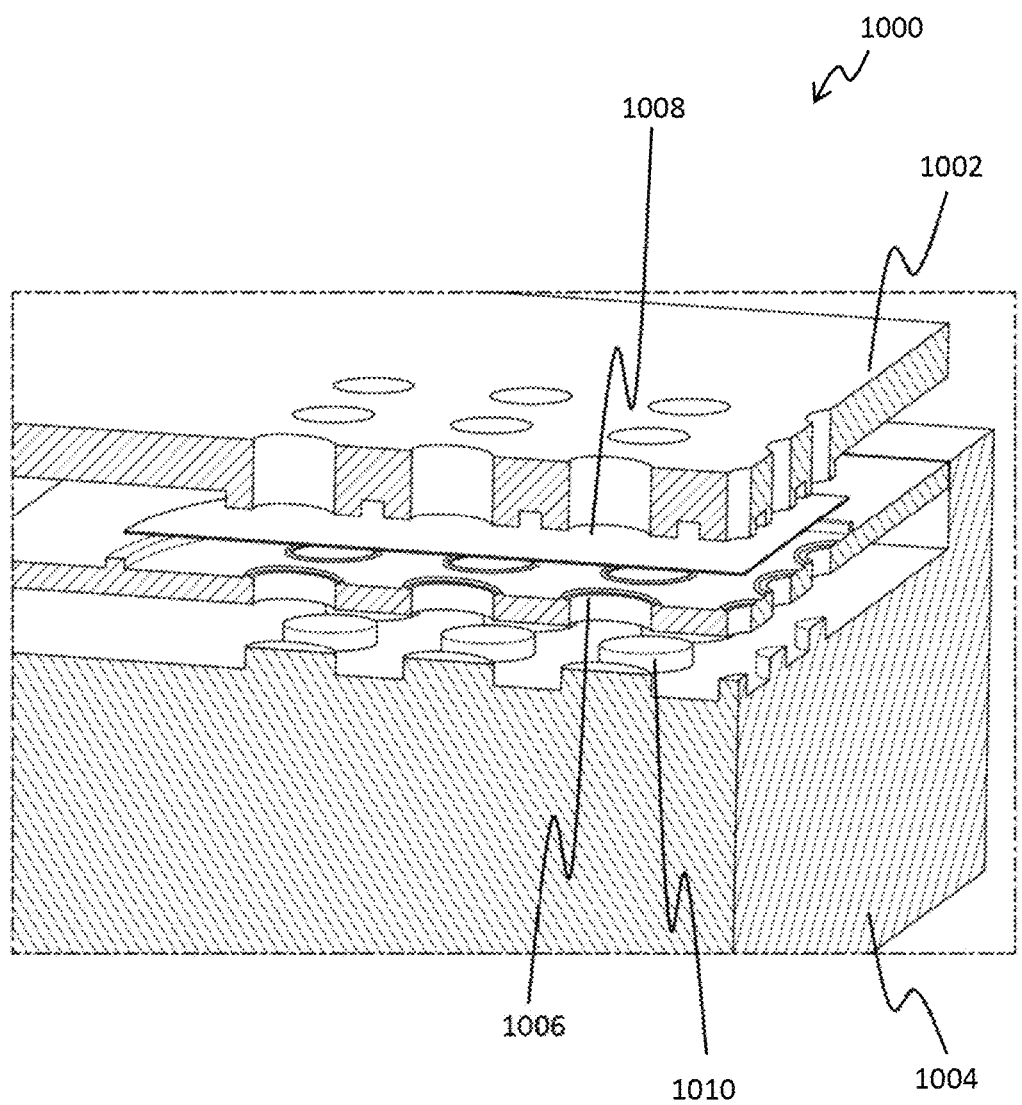
FIG. 12 is a perspective cutaway view of a jig for manufacturing a well plate according to one embodiment.

With reference now to FIG. 12, to create the membrane plate, a thermal bonding technique can be utilized according to one embodiment. The 32-well plate 1006 and the membrane 1008 are placed into a compression jig having a top 1002 bottom 1004 and the jig is placed into a heated press. Heat is only applied to the side of the press where bonding takes place. Then, pressure is applied to carry out the bonding. Both the membrane and the plate itself are made of polycarbonate. Polycarbonate plates were chosen so that they match the material of the membrane so that thermal bonding could take place. In order to prevent plate deformation during the hot bonding technique the compression jig top 1002 makes contact with the plate 1006 only via some protruding rings which localize the heat to the desired bonding region. Furthermore, the membrane 1008 in the center of the wells are kept comparatively cool through the use of pins 1010 on the compression jig bottom 1004. These pins 1010 are in close proximity to the membranes 108 during the heating process and will cause a local temperature decrease. In certain embodiments, the 32-well plate has a protruding "bead" material around each well that acts as the melting region. In certain embodiments, the bead has a triangular profile such that the tip of the triangle is in contact with the membrane and melts first. This method makes bonding more robust, controlled and strong.

Figure 13A:
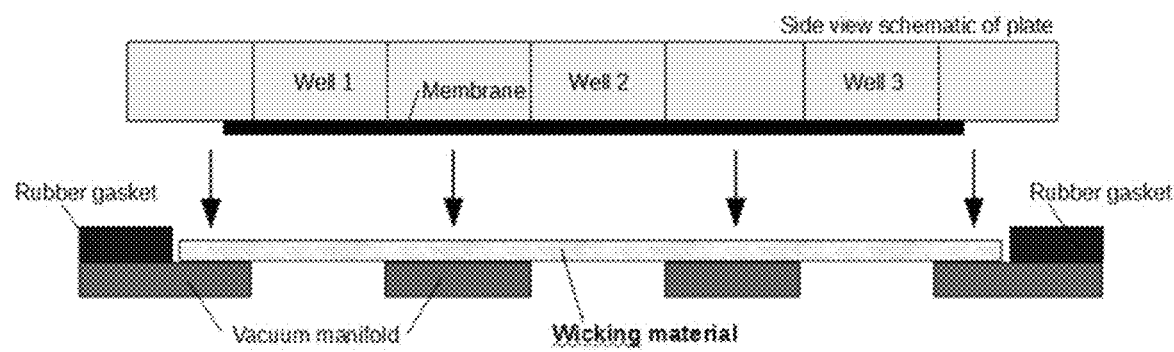
FIG. 13A is a diagram of a step of placing a consumable onto a vacuum manifold having a wicking material according to one embodiment.
Figure 13B:
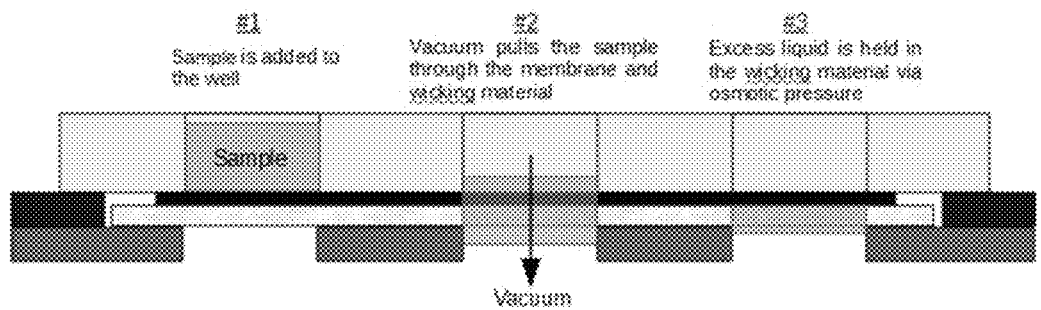
FIG. 13B is a diagram of a step of pulling a sample through the membrane according to one embodiment.

With reference now to FIGS. 13A and 13B, in one embodiment, a wicking material can be utilized in a vacuum manifold. In order to capture a precise image of captured particles, it is important for the membrane to be dry and free of sample droplets that may remain due to surface tension. The vacuum manifold that is used to pull sample through the pores of the membrane can be modified by adding a wicking material (see FIG. 13A) that contacts the bottom surface of the plate and membrane. The wicking material draws bulk liquid droplets away from the plate via osmotic pressure (see FIG. 13B). After the sample has been completely processed through the membrane, the plate is lifted off of the vacuum manifold and away from the wicking material. Any remaining liquid in the microscopic membrane pores rapidly evaporates (<1 s) and the plate is immediately ready for imaging.

Tracer particles can be utilized to improve image processing. Due to variations between different membranes, different wells in the plate, different lighting conditions, due to camera noise and a variety of other sources, comparing images quantitatively is always difficult. Tracer particles of a known shape and size can be added to each well. These tracer particles assist with image balancing, background subtraction and thresholding calculations because. In one embodiment, polystyrene and polycaprolactone of 10 and 15 microns in size is utilized respectively. In one embodiment, a heat or chemical treatment is used to fix the particles onto the surface so that they do not move during sample loading. For example, polycaprolactone can be heated at 65 C for 1 minute. Polystyrene can be treated with nitric acid or heat up to 150 C (so as to prevent membrane deformation). In certain embodiments, innate features on the membranes such as the themselves and the background texture are utilized to improve processing.

In certain embodiments, illumination with the highest signal to noise ratio of particle to background occurs was when there is no material around the membrane (e.g. if the well plate is removed from the membrane and there are no walls for the light to travel through). In one embodiment, either the well plate itself is removed from the membrane for imaging, or alternatively a hydrophobic material is patterned in a shape that leaves wells behind. Thus, in these embodiments, the walls are not physical but chemical.

Advantageously, systems and methods according to embodiments described herein can process a range of low to high volume (e.g. ranges of 10 µL-1 mL or 50 µL-1 mL) at speeds of <1 min per well. This low volume subvisible particle analysis (e.g. at least down to 10 µL or 50 µL) is less than 2-10× of state of the art. The premier sub-visible particle analysis techniques are FLOWCAM and MFI. Because they analyze particle in a fluidic stream, they require lots of dead volume and tubing.

Low volume processing is important. During formulation selection (researchers have already found an API candidate and now it's time to put it in a stable form that can be intaken by the body), researchers do not have a lot of material to play with, unlike in manufacturing (once a formulation has been selected and is being scaled up). Many times, they just have 1 mL per sample for the entire initiative. They would like to be able to do sub-visible particle analysis to test several formulations but currently cannot given tool volume requirements. The approaches described herein can do low and high volume because instead of requiring large fluidic reservoir and lots of tubing (dead volume), researchers just manually pipette samples into the wells, like in a standard plate. The instant embodiments can do large volumes as well, with the limitation not being volume but particle concentration, if too many particles filter is clogged, affecting both imaging and flow.

The embodiments described herein also operate at a higher speed or throughput. In traditional flow imaging (both FLOWCAM and MFI), particles flow in a fluid channel/flow cell and images are taken as each particle flows by. They take multiple images per second to capture individual particles as they flow by. To analyze a 1 ml sample takes 10-15 minutes/sample and the produced files are enormous (tons of images). The instant embodiments are faster due to the flow and imaging conditions. Regarding flow, samples are loaded independently in each well (pipetted in). Then the sample is flown through the mesh/sieve at a high flow rate after applying vacuum. Particles larger than the mesh pore size are stuck while the rest of the fluid flows through. This process can take less than a second. The flow rate here is 100-1000× faster than MFI and FLOW-CAM. This increases throughput from analyzing 1 ml in 10-15 mins to 1 ml in a few seconds. In addition, the analysis of the embodiments shows that the shear rate is low (embodiments do not affect the proteins as they are clogged on the filter). Regarding imaging, the instant embodiments then take a wide field image of the entire mesh which now has particles spread all over. Thus, instead of taking individual pictures hoping that a particle is there (see MFI figure above) instant embodiments flow all the particles quickly and once they are stuck we can take a single image that captures all the particles. Instant embodiments take a few pictures, which contain all of the particles, and can do this under different illumination conditions to extract different physical and chemical parameters from the particles.

Sample recovery is another important aspect of the disclosed embodiments. Unlike traditional flow imaging methods or most particle analysis methods, the consumables of the instant embodiments trap the particles (they don't flush down the sink or to disposal) and therefore can be recovered for additional analysis. This includes additional assays (stability assays, activity assays, solubility assays), or using other inspection technologies including mass spec, FTIR, UV-VIS, SEM, EDX, Raman, etc. Sample banking is important since allows researchers to go back and retrace their processes.

Embodiments described herein are applicable to a number of industries. For example, identifying or characterizing particles in biopharmaceutical samples, including protein aggregates, excipients, silicone oil droplets, air bubbles, glass, metals, fibrous materials, and other intrinsic and extrinsic particles encountered in the formulation and manufacturing processes of the biopharmaceutical formulation process; particles in aquatic research, including fresh water, wastewater and marine research including algae; particles in the oil and gas industry including drilling fluid, frac materials and fuels; and particles in the paints and cements industry.

Figures 14A, 14B:
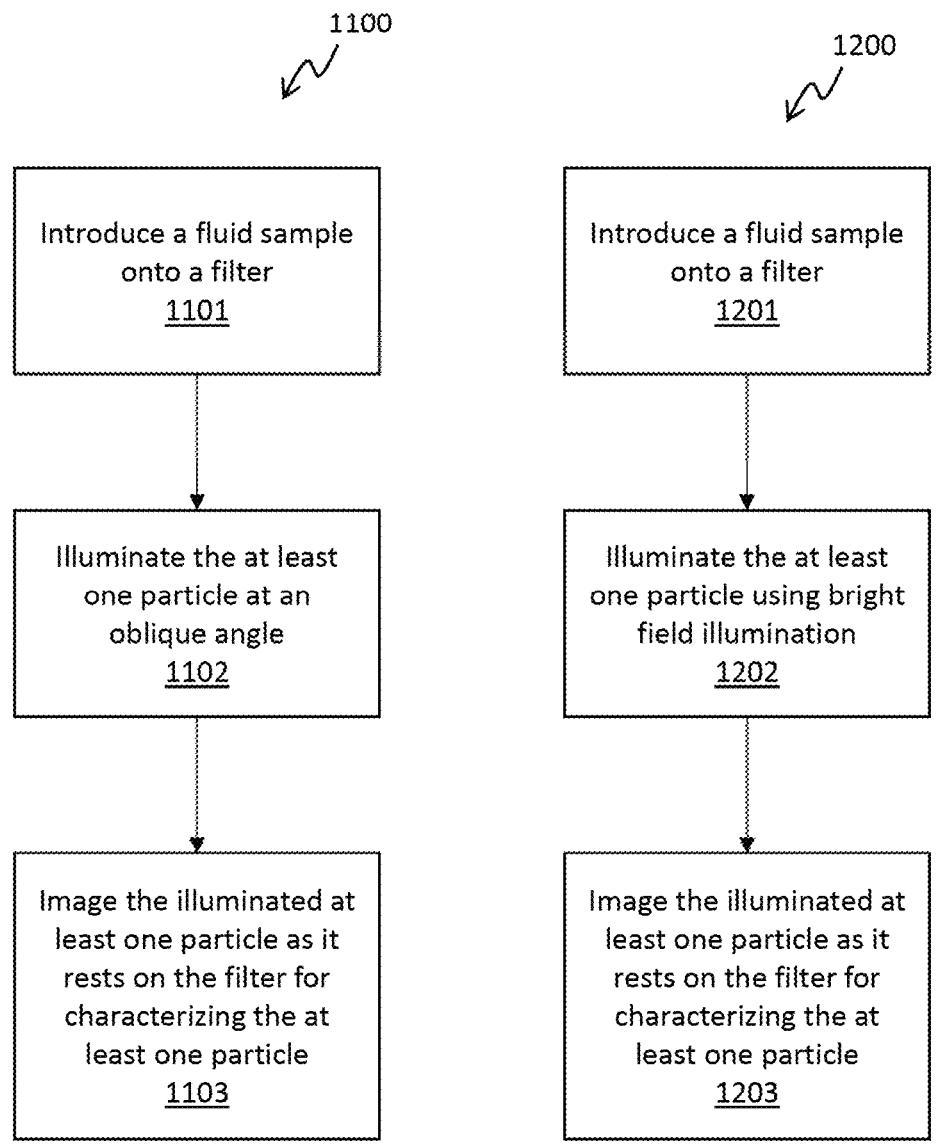
FIG. 14A is a flow chart of a method of characterizing a particle using oblique angle illumination according to one embodiment.
FIG. 14B is a flow chart of a method of characterizing a particle using bright field illumination according to one embodiment.

With reference now to FIG. 14A, in one embodiment, a method 1100 for characterizing at least one particle from a fluid sample includes the steps of introducing a fluid sample onto a filter 1101, illuminating the at least one particle at an oblique angle 1102, and imaging the illuminated at least one particle as it rests on the filter for characterizing the at least one particle 1103. In one embodiment, the method includes the steps of illuminating the at least one particle using bright field illumination. In one embodiment, the method includes the steps of generating a composite image based on the oblique angle and bright field illumination. In one embodiment, the method includes the steps of illuminating the at least one particle by radially surrounding the at least one particle with a plurality of illuminating devices and illuminating the at least one particle from an oblique angle. In one embodiment, the method includes the steps of illuminating the at least one particle in one of a plurality of wells disposed on a well plate. In one embodiment, the method includes the steps of charactering the at least one particle based on imaging prior to an after a fluid sample is introduced onto the filter. In one embodiment, the method includes the steps of individually and separately imaging each of the plurality of wells. In one embodiment, the step if imaging comprises imaging at a plurality of heights above the filter. In one embodiment, the plurality of images comprises a high dynamic range set of exposures. In one embodiment, the method includes the steps of merging the plurality of images together into a single image. In one embodiment, the plurality of images comprises replicates. In one embodiment, the method includes the steps of mathematically registering two or more images. In one embodiment, the method includes the steps of mathematically registering before and after images. In one embodiment, the method includes the steps of introducing the fluid sample into a well on a well plate. In one embodiment, the method includes the steps of illuminating the at least one particle through an optical feature of the well plate comprising at least one of a mirror, lens and prism. In one embodiment, the method includes the steps of characterizing and identifying a material type of the at least one particle using a machine learning algorithm. In one embodiment, the machine learning algorithm uses observed features including at least one of size, shape, texture, dark-field intensity and intrinsic fluorescence of particles to build models.

With reference now to FIG. 14B, in one embodiment, a method 1200 for characterizing at least one particle from a fluid sample includes the steps of introducing a fluid sample onto a filter 1201, illuminating the at least one particle using bright field illumination 1202, and imaging the illuminated at least one particle as it rests on the filter for characterizing the at least one particle 1203. In one embodiment, the method includes the steps of illuminating the at least one particle at an oblique angle or an angle coplanar with a flat plane of the filter. In one embodiment, the method includes the steps of illuminating the at least one particle by radially surrounding the at least one particle with a plurality of illuminating devices and illuminating the at least one particle from an oblique or coplanar angle. In one embodiment, the method includes the steps of illuminating the at least one particle in one of a plurality of wells disposed on a well plate, wherein each of the wells terminates in a filter.

In one embodiment, fluorescent capabilities are added to enable high throughput identification of particulates. This additional capability is either based on native fluorescence or labeled fluorescence approaches. Unlike other approaches, fluorescence is chemically specific, and enables high signal to noise measurements, making it ideal for high throughput (fast) and specific identification and differentiation of particles in a solution. In the embodiments, this fluorescent information gives specific particle ID and categorical identification (type of particle, e.g. Protein or not a protein), with particle information acquired via backgrounded membrane imaging (previously described above).

One key application that this enables is early pharmaceutical quality control of particulates. Researchers want the ability to distinguish between particles that are the drug product (e.g. DNA therapeutic aggregates, protein aggregates, viral aggregates) vs. other common particles found in the drug products (precipitated excipients like polysorbate, salt or sugar—or extrinsic matter like plastics, silicone oil, shards of delaminated glass or metal from pumps). Fluorescence enables both categorical (general category, is it a protein or not) as well as specific identification. Rapid specific and categorical identification enable upstream adoption and the ability to not use identification tools only at the point of failure, forensically.

Figure 22A:
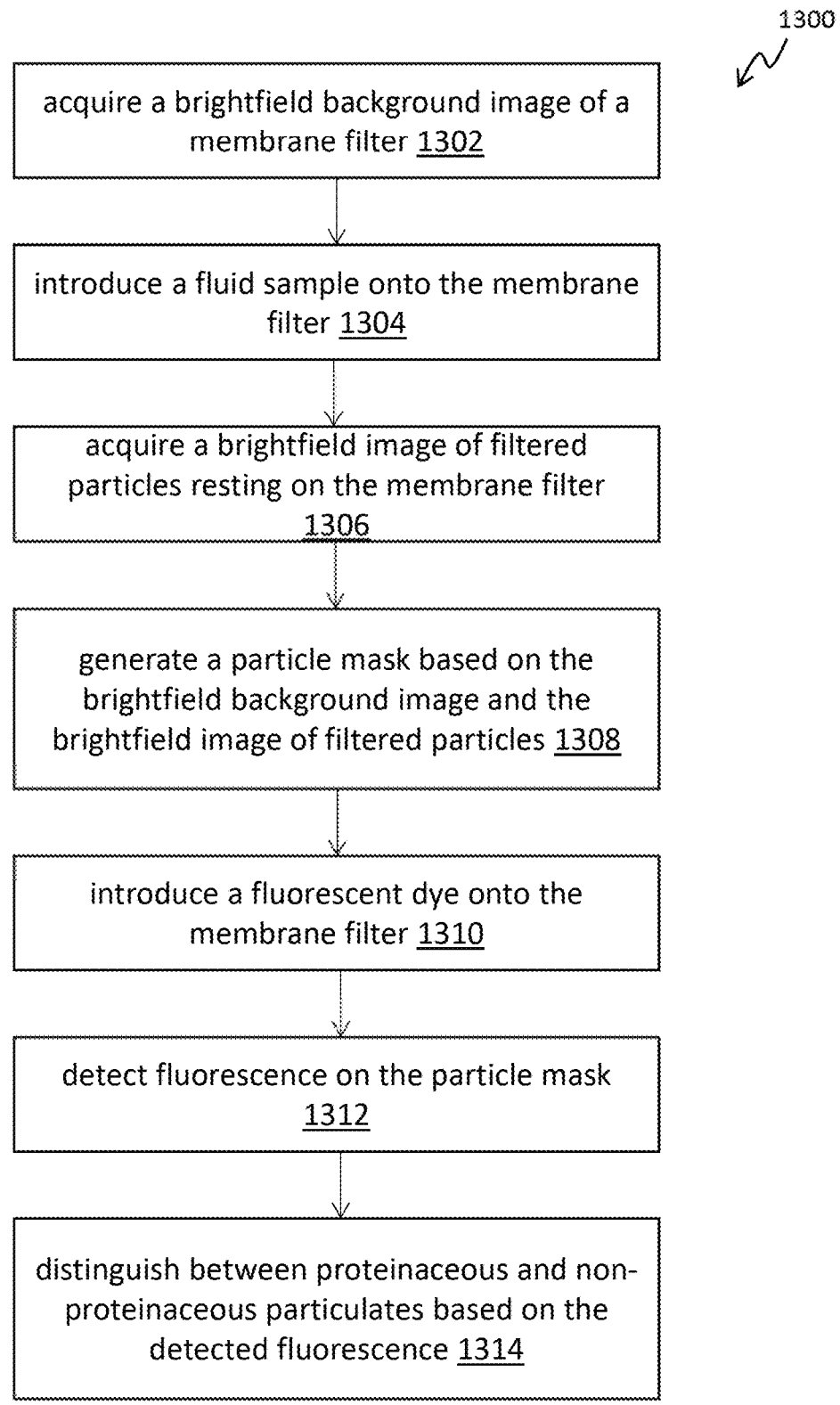
FIG. 22A is a flow chart of a method for distinguishing between proteinaceous and non-proteinaceous particulates in a fluid sample according to one embodiment.

With reference now to FIG. 22A, a method 1300 of distinguishing between proteinaceous and non-proteinaceous particulates in a fluid sample is shown according to one embodiment. The method 1300 includes the steps of acquiring a brightfield background image of a membrane filter 1302, introducing a fluid sample onto the membrane filter 1304, acquiring a brightfield image of filtered particles resting on the membrane filter 1306, generating a particle mask based on the brightfield background image and the brightfield image of filtered particles 1308, introducing a fluorescent dye onto the membrane filter 1310, detecting fluorescence on the particle mask 1312, and distinguishing between proteinaceous and non-proteinaceous particulates based on the detected fluorescence 1314.

Figure 22B:
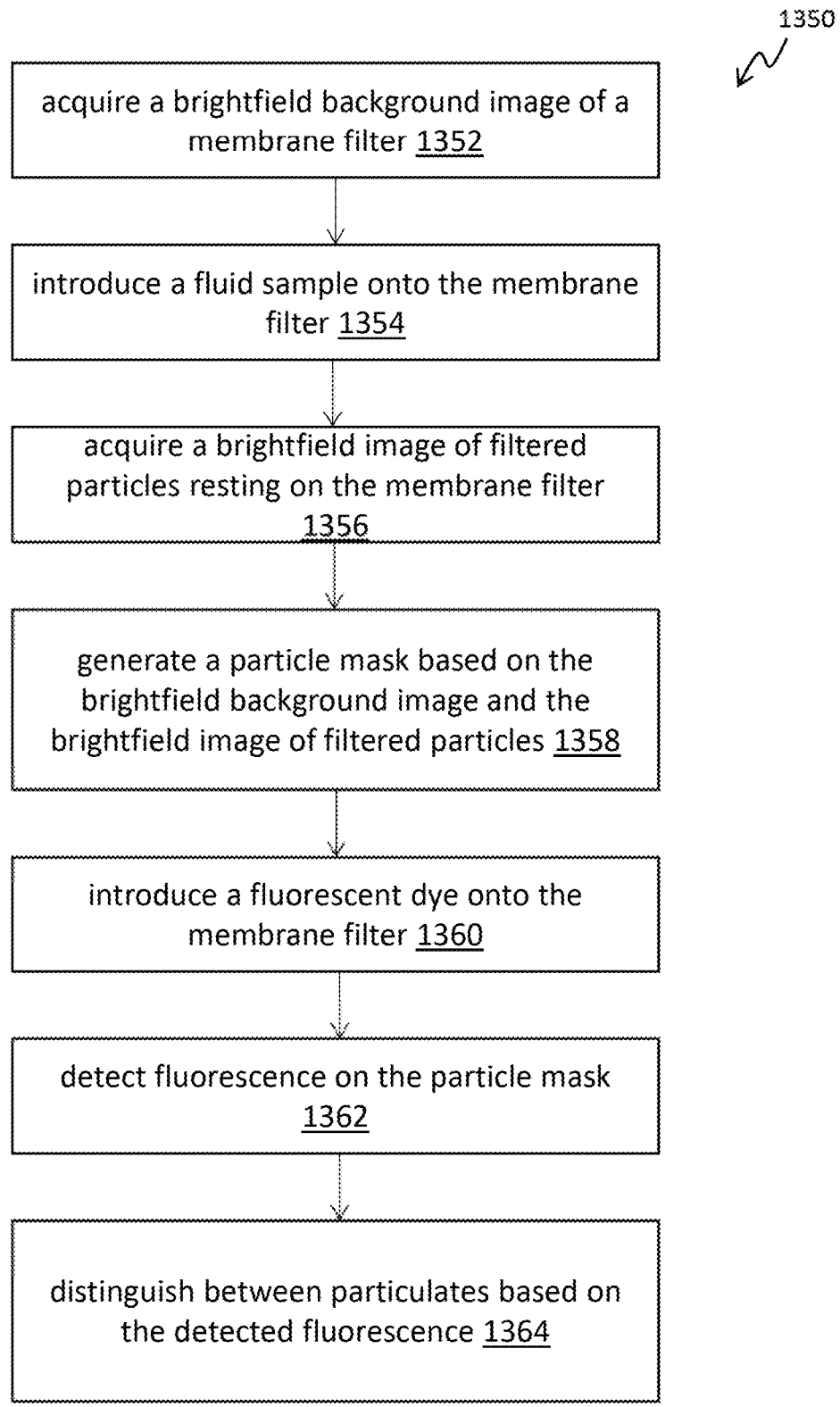
FIG. 22B is a flow chart of a method for distinguishing between particles, such as proteinaceous particles, non-proteinaceous particulates, polysorbate particles and silicone oil in a fluid sample according to one embodiment

An alternate embodiment is described in FIG. 22B, which described a method 1350 for distinguishing between particulates in a fluid sample according to one embodiment, that is not specific to distinguishing between proteinaceous and non-proteinaceous particulates. As described in more detail below, there are fluorescent assays available for polysorbate particle detection as well as silicone oil detection, thus certain embodiments would enable not just protein vs. non-protein detection, but also specific detection of important particles present in biopharmaceuticals that point to problems in the formulation (e.g. polysorbate and silicone oil). So similar to the method 1300 described in FIG. 22A, the method 1350 of FIG. 22B includes the steps of acquiring a brightfield background image of a membrane filter 1352, introducing a fluid sample onto the membrane filter 1354, acquiring a brightfield image of filtered particles resting on the membrane filter 1356, generating a particle mask based on the brightfield background image and the brightfield image of filtered particles 1358, introducing a fluorescent dye onto the membrane filter 1360, detecting fluorescence on the particle mask 1362, and distinguishing particulates based on the detected fluorescence 1364. The distinction can include protein vs. non-protein, polysorbate particle detection, and silicone oil detection (explained in further detail below).

The method for distinguishing between proteinaceous and non-proteinaceous particulates will now be described according to three techniques for tying fluorescent information to particle data via three different workflows. Different users may prefer different workflows, for example if they are more comfortable dying the product directly or dying the product once its filtered on the membrane.

Figure 23:
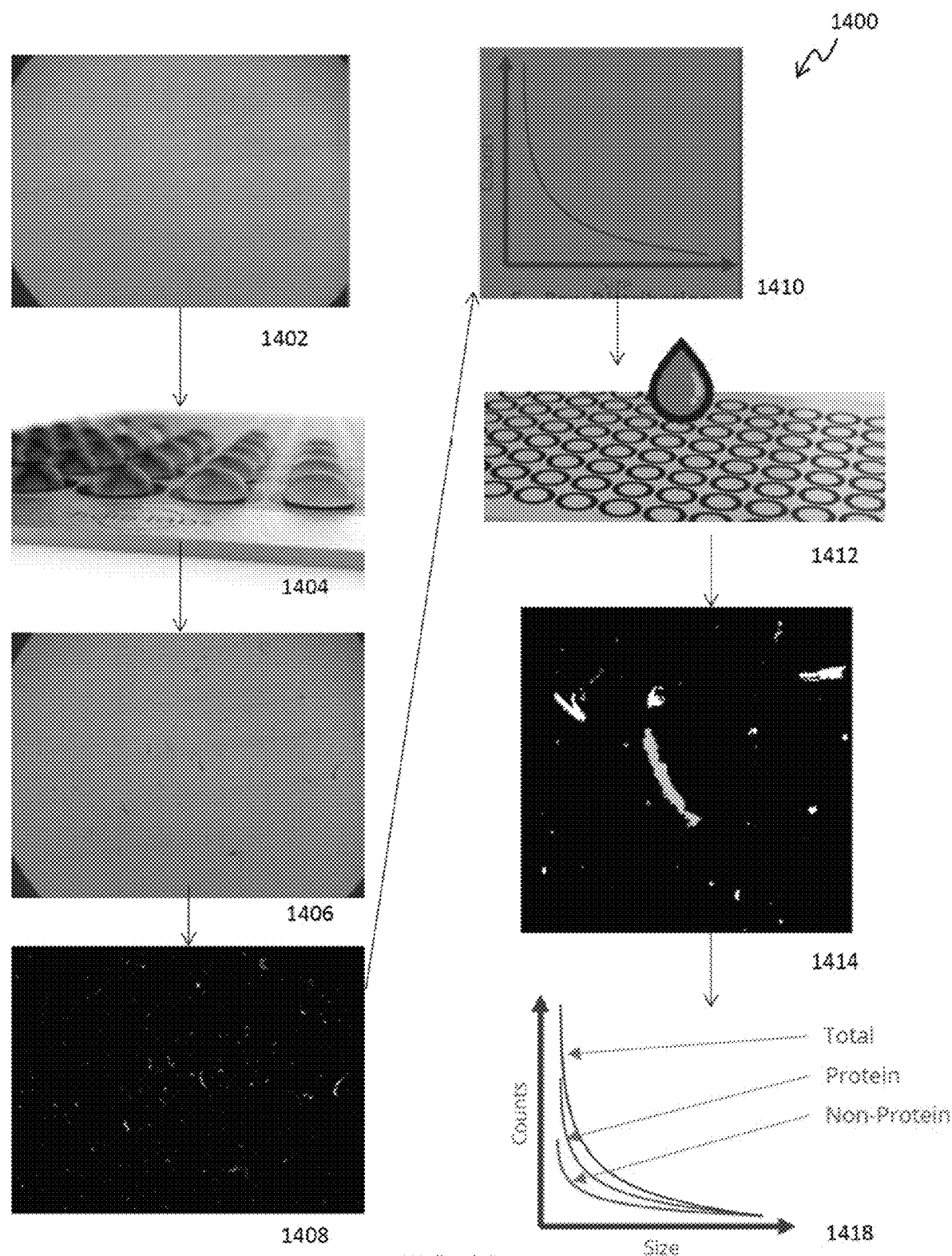
FIG. 23 is a flow chart of a workflow method for distinguishing between proteinaceous and non-proteinaceous particulates in a fluid sample according to one embodiment.

A first workflow example keeps sizing consistent by sizing in brightfield and only using fluorescence for chemical identification, not fluorescence-based sizing. With reference now to FIG. 23, according to one embodiment, a background brightfield image of membrane is acquired 1402 and the sample to be measured is introduced to the membrane 1404 and filtered through the membrane. A brightfield image of the filtrate (filtered particles) now dry and resting on the membrane is acquired 1406. The particulate and background images are aligned via registration and wherever there is a particle that wasn't present in background (before image) it is now detectable. Software thresholds are implemented to look at the difference in pixel intensities to be able to determine what is a true particle from the sample (not on the background membrane). This results in what is known as a particle mask 1408. Everywhere where there are no particles detected, the system won't accept data, and it won't look for data there, even for example if there were new particles or even dye particles that landed in this now dark region. The system only looks in the area designated as where the particles are and nowhere else. This helps avoid for example not measuring a dye particle and confusing it with a real protein particle that fluoresces. The particle mask is analyzed, generating a particle size distribution 1410. In biopharmaceuticals, there are almost always lots of small particles (<10 um) and very few big ones, as shown by the shape of the particle distribution curve (exhibiting exponential decay).

In one embodiment, a background fluorescence image in the optical channels are taken to subtract baseline fluorescent intensity. This can also help if there are pieces of dust on the membrane, which can fluoresce (and which is not desired) in the fluorescence channel of interest, which can confound the signal. It is a background fluorescent signal to ensure that any background fluorescence can be properly subtracted out Next, the fluorescent dye is added over the filtrate 1412, between 5 and 50 uL of dye of choice, to specifically stain the product (e.g. protein aggregates). Fluorescent excitation in the different fluorescent channels is performed and acquired by the system. Different wavelengths can focus at different heights, but this difference in heights can be measured once and then an offset to ensure proper focus at different wavelengths can be performed. Fluorescent registration is performed, aligning the fluorescent image to the brightfield mask image. The fluorescent signals of the given particles are aligned to its corresponding particle in the original particle mask 1414. Again, sizing is only done only in brightfield, not in fluorescence. Particle size distribution with fluorescent particles, non-fluorescent particles, and sum total (fluorescent and not fluorescent) are generated 1416. In this case, it is shown for protein aggregate detection (i.e. showing product aggregates, external and particles in process not the product, and the sum of the two).

Thus, in one embodiment, the method includes generating a total particle distribution, a protein particle distribution, and a non-protein particle distribution based on the distinguishing. In one embodiment, the method includes generating an image of protein and non-protein particles, wherein the protein and non-protein particles are different colors. In one embodiment, the method includes ignoring data outside the particle mask for the steps of detecting and distinguishing. In one embodiment, the method includes acquiring a background fluorescence and removing baseline fluorescent intensity. In one embodiment, the method includes the step of introducing a fluorescent die takes place immediately after the step of introducing a fluid sample onto the membrane filter. In one embodiment, the fluorescent dye is introduced to the fluid sample prior to the step of introducing the fluid sample onto the membrane filter. In one embodiment, the membrane filter is a track etched membrane. In one embodiment, the membrane filter is dyed with a fluorescence photo absorber. In one embodiment, the photo absorber comprises sudan black dye. In one embodiment, the membrane filter comprises a polycarbonate or polyester. In one embodiment, the membrane filter is coated with PVP. In one embodiment, the step of introducing a fluorescent dye comprises introducing between 5 and 50 uL of dye. In one embodiment, the fluid sample is bounded by a hydrophobic ring disposed on a well plate. In one embodiment, the method includes individually and separately imaging a plurality of fluid sampled bounded by a plurality of hydrophobic rings disposed on the well plate.

Figure 24:
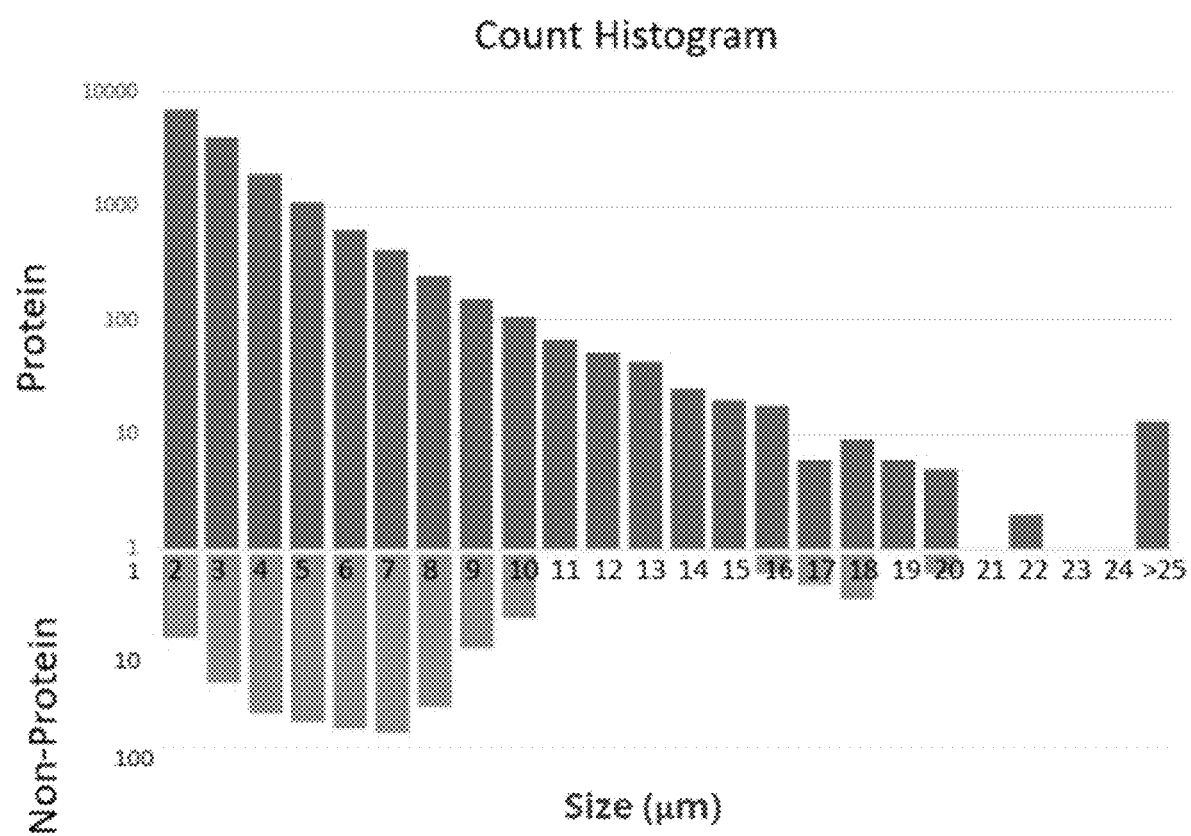
FIG. 24 is a count histogram according to one embodiment.

As shown with reference to the count histogram of FIG. 24, the method can produce data distinguishing protein and non-protein particles among different sizes. Both brightfield and labeled images can be available for view and report. Users can also compare counts and particle identification across wells. Brightfield and fluorescent images can be overlaid or viewed separately.

As mentioned above, the workflows can vary based on user preference or testing preference. For example, except the dye can be added during sample processing. The advantage is speed, as this workflow saves a plate handling and reading step. The disadvantage is confounding dye particles with real sample particles. In an alternate workflow, the solution is incubated with fluorescent dye. This again requires less plate handling and reading steps. The advantages include solution phase binding, which may yield better fluorescent labeling since its done with the particles in the solution. It's also faster, as you don't need to handle the plate three times as described above. The disadvantages are that if there are dye particles present, these may lead to false positives since dye particle could be counted as a product particles that should have been labeled with the dye. So an advantage of the workflows described in FIGS. 22 and 23 is that if a user runs the system not in fluorescent mode, the user can opt to run dye over his wells and utilize fluorescent analysis later. Otherwise, adding fluorescent dye material to the biopharmaceutical samples may sometimes impact the biopharmaceuticals themselves. Applying the dye after the sample has been filtered can be less invasive to impacting the native state.

To perform specific identification of protein aggregates, fluorescent dyes that bind specifically to domains found protein degradation are used. Several dyes know in the art will work (see e.g. Hawe et al, Pharmaceutical Research, Vol. 25, No. 7, July 2008 (#2007) DOI: 10.1007/s11095-007-9516-9) based on their mechanism of binding to protein aggregates, as well as their optical excitation and emission properties. The main protein aggregate dyes (and corresponding optical channels to make the dyes fluoresce) are BisAns and Nile Red, binding to hydrophobic pockets of misfolded proteins. The associated optical emission and excitation spectra are adapted in the system. Protein aggregate dyes and cocktails (combinations) of these dyes, are used for the specific detection of protein aggregates from other particles present in biopharmaceuticals.

There are other dyes that enable specific detection of excipients (stabilizers of the product of interest in the solution) and other particulates present in protein drug formulations. For example, there are fluorescent assays available for polysorbate particle detection as well as silicone oil. This would enable not just protein vs. non-protein identification, but also detection of important particles present in biopharmaceuticals that point to problems in the formulation, such as polysorbate and silicone oil.

Figure 47:
FIG. 47 is an image of Protein aggregates that were filtered through a membrane and labeled with Alexa 488 fluoresce with strong signal to background ratio.
Figure 48:
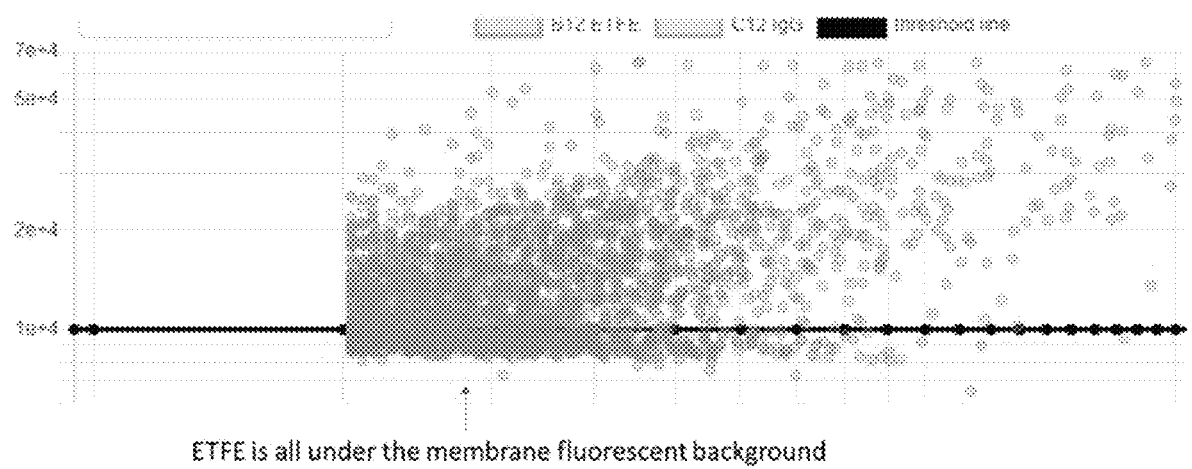
FIG. 48 is a graph showing Aggregated Human IgG and ETFE labeled with Alexa dye.

Advantageously, monomer dyes can be used in embodiments described herein while they can't normally be used in a liquid system because everything would light up. Alexa488 is one example of a monomer dye. This monomer dye works in embodiments of the system described herein (but not in tools like flow imagers) because the embodiments filter all the liquid out and just the protein aggregates (which are still of course made out of protein) remain. In a liquid system, a monomer dye would make the entire solution glow, unable to distinguish protein aggregates form the solution. With reference now to FIGS. 47 and 48, using a fluorescence supporting membrane, the monomer is filtered through the membrane, and if any is left, it generates a very weak signal (background is black) compared to protein aggregates. ETFE is the plastic standard used as a negative control.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

In certain embodiments, 3D printed flow cells are used to hold and perform experiments on the electroformed micromeshes in isolation (without microflow imaging). In other embodiments, a flow cell is designed to allow for simultaneous microflow imaging and delivery of samples through our filter chip. In certain embodiments, the design must: (1) contain a fluid channel of specific thickness such that the entire height of the microchannel lays within the depth of field of our imaging system while allowing the desired particle size range to pass through freely, (2) the assembly of the chip and flow cell should be simple and robust (e.g. free of leaks or introduction of contaminants), and (3) the flow cell thickness above the surface of the micromesh must be sufficiently thin to allow access for and imaging by a high magnification objective for spectroscopic characterization/imaging. In one embodiment, die-cut silicone tapes with 50 and 100 μm thicknesses as gaskets between the microfabricated chip and a $CaF_2$ window for IR transparency are used. Custom stainless steel holders are machined with o-rings and tube fittings to perform micro- to macrofluidic coupling, in a fashion similar to the NanoTweezer Surface product. The machined holder will also house illumination optics for microflow imaging. Alternatively, a micro-gasket can be employed instead of a silicone tape, allowing for removal of an ordinary piece of glass prior to spectroscopy. In other embodiments, the flow cell is not designed for imaging, but instead the particles will be imaged on the micromesh. In this embodiment, the flow cell does not need to be transparent. Since imaging will take place on the micromesh, the thickness of the flow cell above the micromesh as well as the flow cell cover need to be controlled. Ideally a quartz cover slip can be used with as thin a gap as possible that will allow the particles to flow through. However, a glass cover slip can be used as well. The cover slips may also be removed before spectroscopy in order to get the best imaging and spectroscopy results.

In certain embodiments, wafers will consist of 2, 3, and 5 um circular pores designs. Samples are prepared to contain approximately 2,000 particles, 5-50 microns in diameter, per mL, such that the resistance of each chip due to pore clogging changes less than 5% for each pore size. Each sample (1 mL volume) is passed through the mesh at a controlled flow rate ranging from 0.25-5 m L/min (comparable to current flow rates employed in microflow imaging). Flow rates are maintained via an active feedback loop using an in-line flow sensor and our pressure regulation module. Capture efficiencies for each pore size are quantified by performing particle counts via microscopy on each mesh, and comparing counts to the initial concentration as determined by microflow imaging. Second, the effect of particle loading on capture efficiency and flow rate is determined, and hence the capacity of each filter design. High concentration samples (10,000 particles/mL) are flowed through each chip while monitoring the volumetric flow rate at a constant applied pressure. As particles are trapped on the mesh, the flow rate is expected to decrease until the device clogs (flow rate=0) or capture efficiency drops due to particles being pushed through the pores, and flow rate stabilizes at a low value. Through this experiment it is expected to get both an estimate of the filter capacity, in terms of total number of trapped particles, as well as an understanding of the flow rate (at constant pressure) signatures as the filter capacity is reached.

Preliminary data has been acquired using a prototype apparatus consisting of an Olympus BX-51 microscope configured for bright field illumination, a spectrometer (Tornado) and a 785 nm laser (Innovative Photonics Solutions) for Raman analysis, and a CMOS camera (Basler). Incorporated into the setup is a focal plan array detector for high-throughput compositional mapping. With a Raman system, spectra is acquired at a rate of one every two seconds. For a mesh with 5000 particles trapped, it would require approximately 3 hours to acquire spectra from every particle, followed by spectral processing and identification. FTIR imaging utilizing a focal plane array detector allows simultaneous acquisition of IR absorbance spectra for each pixel of the image. In this format, extremely high volumes of spectra can be acquired in a short time. For example, utilizing a focal plane array from Bruker, a detector we have arranged to test in Phase II, high resolution spectral imaging is obtained at about 0.5 $mm^2$/min (16 scan average, 4 $cm^{-1}$ resolution, 5.5 um pixel resolution), which translates to approximately 10 minutes to acquire spectra (147,456 spectra total) for the entire filter area. We evaluate both the throughput and stated resolution of two FPA detector providers with protein aggregate samples trapped on microfabricated chips to determine the best components based on performance and cost of integration.

A custom microflow imaging system is optimized for chip design and channel dimensions. A custom board housing a high power 460 nm LED (Luminus Devices Inc.) and heat sink is fixed to the bottom of the flow assembly. Control of the LED is integrated with a CMOS microscope camera (Basler Inc.) to flash during each image acquisition at a rate of 62 fps, which as described below will be sufficient to sample each particle multiple times. Prototype software controls both the illumination intensity and the camera, allowing users to adjust acquisition time, exposure and frequency. Using a 4× objective and a camera sensor size of 22.5×16.9 mm, both the mesh and microflow imaging region of the chip will be visible within the same field of view. Data obtained with our microflow imaging module is validated by comparing with data collected on commercial microflow imaging systems using spiked samples of particle standards.

The FTIR spectroscopy platform and the flow imaging components are integrated into a stand-alone instrument. For hardware integration, an instrument casing houses a custom, horizontal optical train consisting of a microscope objective (potentially two depending on the requirements of IR imaging and microflow imaging), a splitter leading to a camera and to the FPA detector. The instrument box also houses the modulated excitation source for IR imaging, a pressure control board, and the microflow imaging unit, consisting of the flow cell and strobed blue LED illumination.

A software platform implements routine sample analysis. The existing particle tracking algorithms link particles imaged in the microflow imaging region of the chip to specific locations on our patterned micromesh. Also automated is the control of both the microflow imaging conditions, flow conditions (pressure and flow rate) and spectral acquisitions, which will serve to improve usability as well as consistency of results.

In certain embodiments, particle tracking software is used to track and measure particles during flow, as well as identification of particles trapped on the mesh. In certain embodiments, linking of microflow imaging data to the spectra obtained for each particle on the micromesh is implemented. With a typical particle count of around 5000 particles per 10 mL sample, the fluid volume in our imaging region (~0.44 µL) contains approximately 0.22 particles at any given instant. At a typical flow rate of 0.1 m L/m in, the fluid volume will be refreshed approximately 4 times per second. Imaging is implemented at a frame rate of at least a factor of 5× faster than the fluid volume refresh rate to ensure a particle is imaged several times between entering the imaging region and being captured on the mesh. The implementation of tracking will enhance our sampling rate over conventional micro-flow imaging, which intentionally incorporates gaps between sampling to ensure particles are not counted twice.

In certain embodiments, the addition of particle tracking to image processing will build largely on the NanoTweezer Surface platform, which performs spot detection, linking of spots, and reporting of particle characteristics and tracking characteristics on 80,000 frame datasets (which would correspond to ~45 minutes of microflow imaging data at 30 fps) containing 10-20 particles/frame in less than 10 minutes. In addition, a software package that utilizes graphics processing units (GPUs) can be implemented to reduce our processing time by a factor of 10.

We first attempt to track particles from entry into the channel until they are trapped on the mesh. Once a particle leaves the microflow imaging region, it may be difficult to track the particle above the patterned background of the micromesh. When a particle is trapped by a pore, however, a distinct reduction in transmitted light is observed at the pore location. If we are unable to track particles above the mesh, we can use this feature to link trapped particle locations to their microflow images. The low concentration of particles in a typical Biopharma samples suggests that on average a new particle will be observed every 1-10 frames (for concentrations ranging from 100-1000 particles/mL). We expect this rarity will facilitate linking particles observed in the microflow section to newly trapped particles on the mesh using local changes in transmitted light. As an additional risk mitigation step, we will evaluate whether there is useful correlation between observed streamline locations of flowing particles and trapped locations on the mesh, under the laminar flow conditions found in our microchannel.

In certain embodiments, imaging conditions, spectral acquisition conditions, and flow conditions are determined by the user, and manually set and executed using software packages developed in-house. Furthermore, spectral signatures/peak locations of suspected materials are manually added to our program in order to generate compositional maps. In addition to eliminating the need for intensive training, automation via software is used to improve run to run consistency. Automation of key steps in setting up and running a successful experiment is preferable. First, exposure time and illumination frequency and intensity is automatically adjusted to maximize image quality for particles introduced by the sample. As discussed earlier, flow parameters will be monitored such that the run is automatically terminated when a predetermined volume has been processed, or when a degree of particle load on the filter is achieved. When spectral acquisition is executed, the mesh will be automatically sampled over its entire area. Acquired spectra will be matched against a spectral database to identify composition.

In one embodiment, a database utilizing p fluorescence imaging is utilized. Different particles can have different scattering properties at different excitation wavelengths. A model is created or trained using machine learning. In certain embodiments, fluorescence is used in place of raman/FTIR because it is high signal. Fluorescence is not as specific as the spectral signatures achieved with raman/FTIR, but because the types of contaminants are limited (protein aggregates, metals, rubber, etc), the full power of complex spectroscopy is not necessary. In certain embodiments, 3 channels of fluorescence and a good model for each particle type is sufficient for particle characterization and identification.

One method to obtain rapid particle composition information in the size range that is most important for certain embodiments of the device is through spectroscopy. Of the various spectroscopic methods available, Mass Spectrometry is typically used more upstream during drug design and suffers from very complex sample prep. Optical spectroscopy, like FTIR is more commonly used to ensure that the bonds of interest are present. FTIR is fairly high throughput compared for example to Raman. Raman spectroscopy while potentially more chemically sensitive suffers from several orders of magnitude lower signal and throughput. Furthermore, neither FTIR nor Raman are used in routine biopharm analysis, and only in forensic analysis (once things have gone wrong) due to their low throughput. Routinely identifying protein aggregates is key with this research tool. With the protein aggregate information, researchers can attest whether they should relook at their formulation or whether other particles may be present. In order to achieve this measurement on a routine and not low throughput basis, multichannel fluorescence is utilized and prioritized over other technologies like FTIR or Raman. Fluorescence can accomplish the "crude spectroscopy" with the throughput needed to meet the routine requirement. In one embodiment, multi-channel fluorescence is utilized, since particles will exhibit different fluorescent properties at different excitation wavelengths. For example, using R,G,B, each channel may exhibit unique light scattering characteristics of the particle. In one embodiment, the fluorescence imaging uses intrinsic multi-channel based fluorescence. In one embodiment, the fluorescence imaging uses labeled multichannel based fluorescence.

Fluorescent imaging is a sensitive and non-invasive method for quantitatively evaluating protein autofluorescence (Ghisaidoobe and Chung, Int. J. Mol. Sci., 2014, 15, 22518). Protein and protein aggregates have an intrinsic fluorescence in the deep-UV wavelength range (excitation ~280 nm, emission 303 nm and 350 nm) due to the presence of constituent aromatic amino acids. In addition, proteins that have aggregated together deliver additional fluorescent energies in the larger UV-blue wavelengths (excitation ~340 nm, emission 425, 445, 470, and 500 nm) (Chan, Kaminski, Schierle, Kumita et al, Analyst, 2013, 138, 2156) & (Shukla, Mukherjee, Sharma et al, Archives of Biochemistry and Biophysics 2004, 428, 144). It is speculated that this aggregate fluorescence stems from the presence of higher-order aggregate structure or resonant bond features. Additionally, it is thought that degree of aggregation as well as more specific aggregate structure or type (for example random vs. fibril) can be weaned by evaluation of these aggregate-specific wavelengths. Concomitantly, additional particulate material types that are inherent to the biopharma manufacturing stream and processing equipment, may end up aggregating along with protein or constitute sample impurity. These materials, potentially including polymers, glasses, and metals, can be evaluated rapidly and routinely using fluorescent spectroscopy.

In addition to non-invasive evaluation of autofluorescence using optical spectroscopy, a system utilizing a chip with a geometric grid, such as a hex-shaped grid as described herein, will have an optional ability allowing users to actively label particulate material using a fluorescent probe or dye. The system can be simply adapted to effectively flow a fluorescent dye or antibody solution over captured material on the hex-shaped grid, followed by a rinse of non-bound material. The use of protein staining can allow for enhanced and very specific protein aggregate signal or other material types. For example, Thioflavin-T has been shown to associate rapidly with multimeric β-sheet containing specific amyloid fibrils (Groenning, Olsen, van de Weert et al 07'). With this added capacity, users can take advantage of alternative specific and powerful fluorescent chemical/antibody conjugation methods that have a long history of validation and value in industrial applications, to optionally follow up on their optical spectroscopy results with deeper more specific evaluations of captured particulate material, should the need arise. As described herein, combining bright field with side illumination yields excellent differentiation between particles of different materials.

Figure 15A:
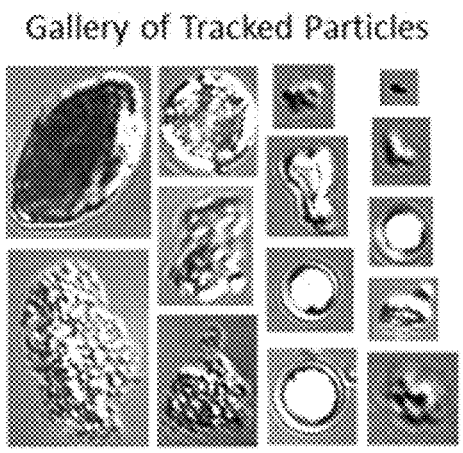
FIG. 15A is a gallery of tracked particles according to one embodiment.
Figure 15C:
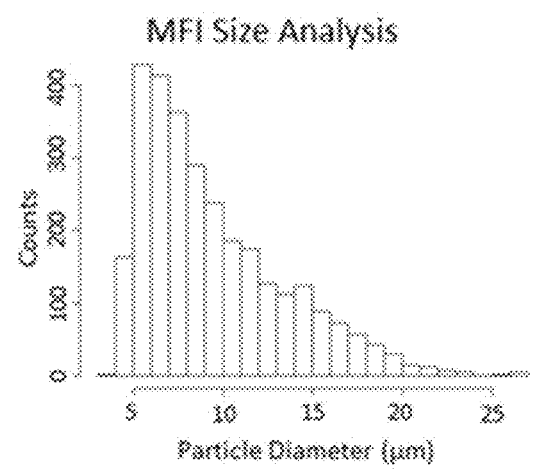
FIG. 15C is a histogram of particle size according to one embodiment.
Figure 15B:
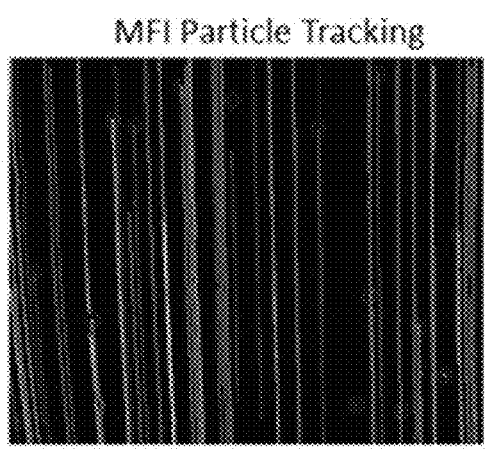
FIG. 15B is a MFI particle tracking graph according to one embodiment.

In certain embodiments, there are three stages to the techniques of the embodiments disclosed herein: microflow imaging (MFI), filtration and spectroscopic identification. Regarding MFI, high quality particle imaging in a flow cell using a MFI setup has been demonstrated (see FIGS. 15A-15C). A simulated biopharma sample was prepared by a heat-treatment method of generating protein aggregates followed by spiking with additional polymeric microparticles (PMMA and PCL). The sample was then run on an MFI system. A gallery of particles (FIG. 15A), post-processed particle tracking (FIG. 15B) and a histogram of particle sizes (FIG. 15C) is shown.

Figure 16A:
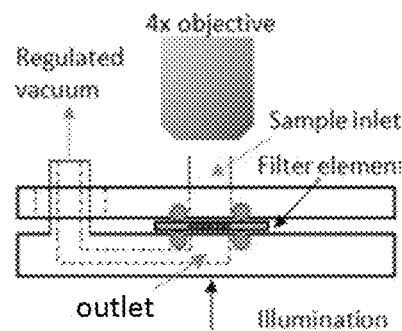
FIG. 16A is a diagram of a system where samples were added to a well and pulled through the mesh using vacuum pressure regulated by a pressure controller according to one embodiment.
Figure 16B:
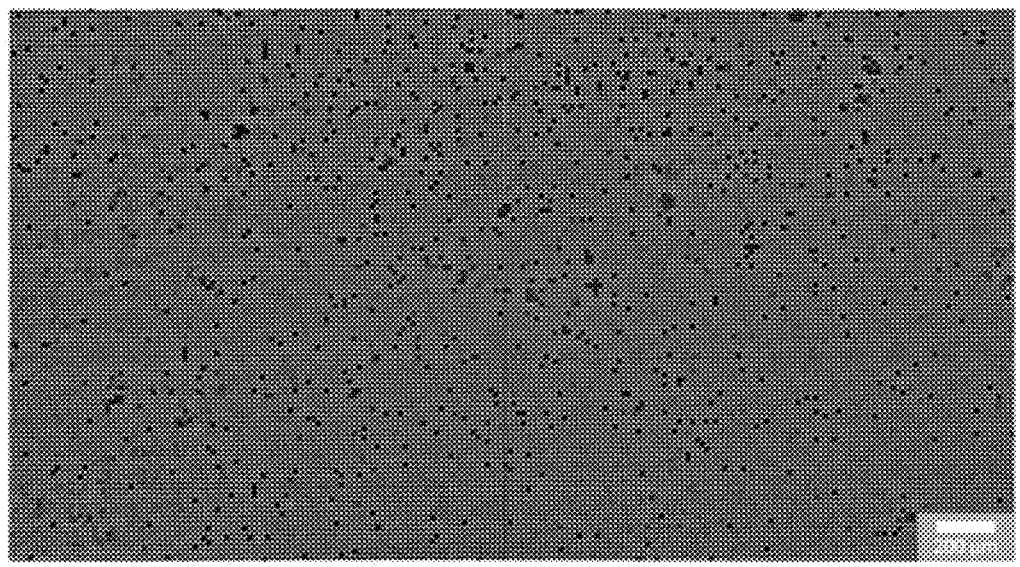
FIG. 16B is an image of a mesh following separation of a mixture of aggregated lysozyme (2-50 um), stainless steel beads (10-20 um), and latex beads (15 um) according to one embodiment.
Figure 17A:
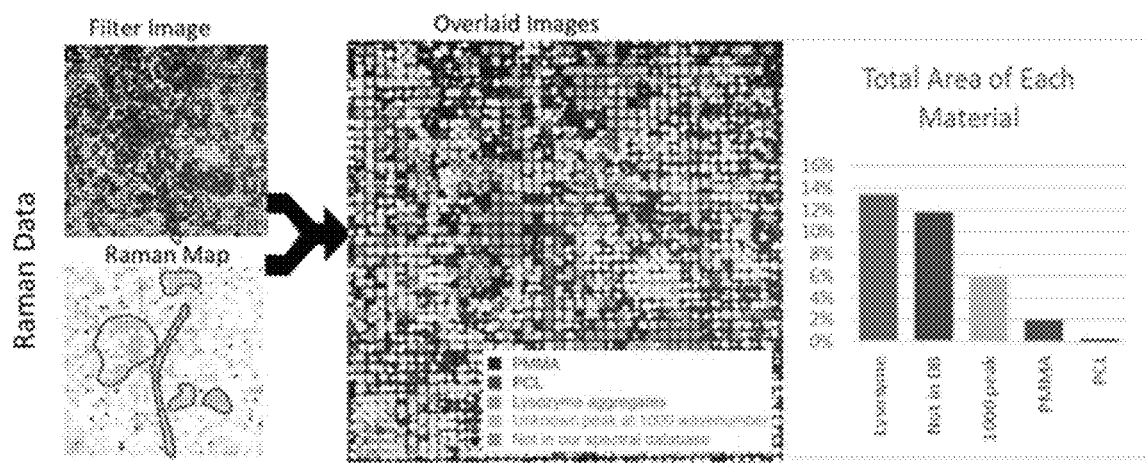
FIG. 17A shows Raman data and outlines that were added to show topographical similarities according to one embodiment.
Figure 17B:
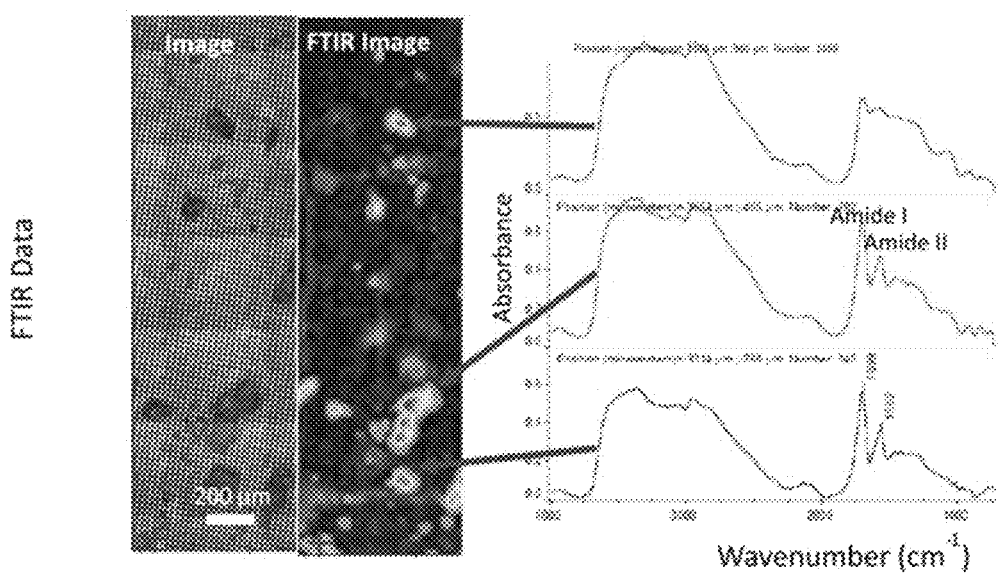
FIG. 17B shows Rapid FTIR imaging data of a sample with a heat map of the Amid I peak at 1700 wavenumber which identifies proteinaceous material according to one embodiment.

With reference now to FIGS. 16A and 16B, a method to capture a simulated protein therapeutic sample consisting of a mixture of protein aggregates and particles in a high protein content solution on a microfabricated grid was developed, and trapping subvisible particles with electroformed meshes is demonstrated. Electroformed meshes were die cut into 20 mm² circles and loaded into a custom built flow cell. Samples were added to a well and pulled through the mesh using vacuum pressure regulated by a pressure controller as illustrated in the diagram of FIG. 16A. Following separations, samples were then imaged under a 4× objective. The image of FIG. 16B shows a mesh following separation of a mixture of aggregated lysozyme (2-50 um), stainless steel beads (10-20 um), and latex beads (15 um). Regarding identification, following the filtration step, the captured particles were scanned using a Raman microscope with robotic stage (see FIG. 17A) and with an FTIR microscope (see FIG. 17B). Microscope images and spectroscopy scans of particles caught on a microfabricated gold mesh with 17 micron pores are shown. A mixture of protein aggregates and polymeric particles were collected with the filters and scanned. Raman data Red outlines were added to show topographical similarities—they do not outline individual particles which are much smaller) (see FIG. 17A). Additional unknown contaminants were identified and shown on the legend. Rapid FTIR imaging of a sample with a heat map of the Amid I peak at 1700 wavenumber which identifies proteinaceous material (see FIG. 17B).

MFI is a quantitative particle imaging technology that has proliferated in the protein therapeutics space (and others) for routine measurements (~10 per day) of protein therapeutic samples. Whereas traditional MFI systems only take one image of a particle, embodiment of the invention uses a higher frame rate in order to track particles to their landing site on the grid. We have implemented an MFI setup in order to obtain high fidelity particle images. In FIG. 12, we demonstrate our ability to capture images of particles in a flow cell, carry out particle tracking and analyze the particles to provide an estimated diameter. Pharmaceutical scientists often look at these particle galleries (which are displayed on their MFI systems) and wonder what these particles are that contaminate their otherwise pristine formulations.

In order to acquire certain preliminary data, we utilize the NanoTweezer platform (launched via a NSF SBIR). The NanoTweezer system also uses a flow cell, particle imaging and particle tracking. Live particle tracking is implemented via GPU processing, which will also vastly improve the processing time for MFI. Lastly, since MFI requires careful flow rate control, the same pneumatically controlled pumping system is utilized that is used on NanoTwezer. This uses an inline flow sensor as part of a PID feedback loop to obtain accurate flow rate (within 5% of requested flow rate) with good stability (<1% c.v.)

This proof-of-concept data shows the ability to design microfabricated structures and use them to capture and subsequently identify relevant materials in a protein therapeutic setting. Several different electroformed micropore grids were used with pore sizes ranging from 11 μm to 25 μm and using both nickel and gold as the material. The best results when combined with Raman spectroscopy was gold, which has excellent properties for use with Raman spectroscopy—low background, high reflectance and sometimes even enhancement via surface enhanced Raman spectroscopy (not used here). The same simulated protein therapeutic sample as described in the previous section was used and captured particulates on the pores. Due to the exceedingly high open area of these filters, an entire mL of sample containing vastly more particles than a real sample was filtered within seconds. Only about 100 millibars of vacuum pressure were needed. FIG. 13 shows the results with a 17 μm pore gold mesh.

Accordingly, imaging, trapping and chemical identification of protein aggregates mixed with standard particle samples on prototype mesh devices has been demonstrated using electroformed meshes integrated into flow cells, a custom-built Raman microscope, and prototype software to drive each component. In certain embodiments, instead of using electro-formed meshes, a microfabricated meshes built on solid supports was used, enabling scalable integration into a flow cell. In certain embodiments, software and hardware is integrated into a single analysis instrument. In certain embodiments, methods are implemented in software for automated mapping of particles imaged during flow to locations on the mesh. The operation and data analysis steps performed by the device are automated.

For certain embodiments utilizing a well plate, image acquisition was achieved using high dynamic range imaging. HDRI is one photographic technique that creates a composite image created from capturing images from low to high exposures (in our case we take 4 to 10 images to generate a single composite HDR image). This allows one to capture a wide range of particle sizes without losing data due to overexposure. The camera that captures the images is a wide field camera in order to be able to take one or a few HDR pictures per well. If multiple sets of images are required to capture the entirety of the membrane, they can be stitched together.

Figure 18A:
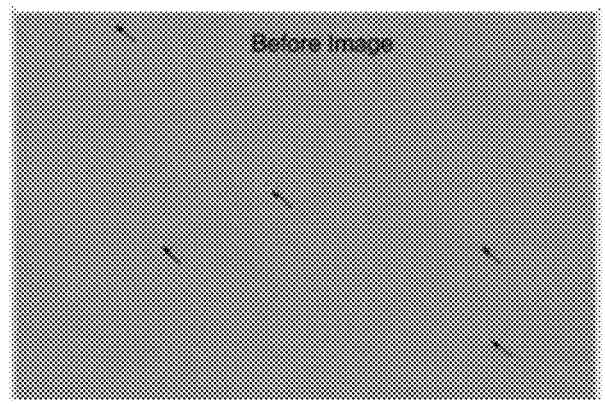
FIG. 18A shows a "before" image where and 5 particles were identified in this section of the before image according to one embodiment.
Figure 18B:
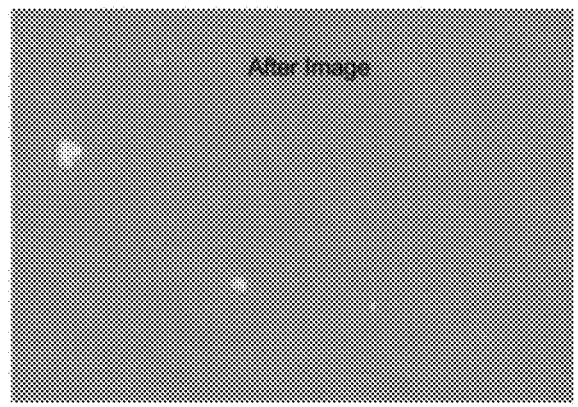
FIG. 18B shows an "after" image identifying a good "after" threshold as described in detail below where the "after" image shown identified 16 particles according to one embodiment.
Figure 18C:
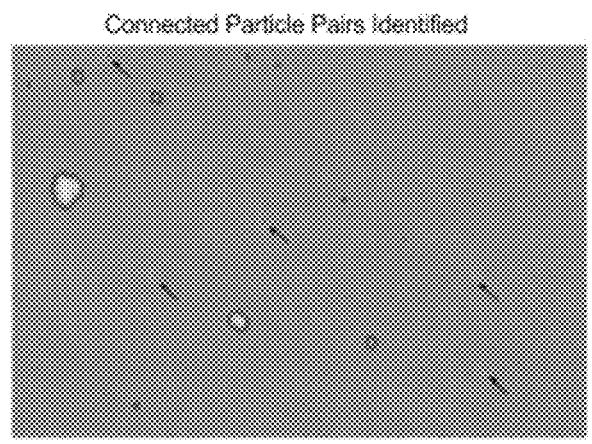
FIG. 18C shows the 5 particles from the "before" image connected to the "after" image, netting 11 new particles that will be reported in this section of the membrane.

As explained above, the membranes we are using for filter material were not perfectly devoid of background features; they have a texture, there may be some contamination in the form of particles, or even scratches in the material itself. In order to accurately count the number of particles added to the membrane surface it is necessary to account for this background. In one embodiment, we do this by taking a "before" image, and an "after" sample image, then compare the two using software algorithms. One method is as follows: Step 1: Image registration. The before and after images are registered so that features shared by the two images are aligned in x, y and rotation as well as introducing a scaling factor to one of the images and allowing for some deformation of the image so that features in the before and after image are at the same x and y position. Step 2: Remove light ring. The images are rectangular views of a circular object. The extra areas of the image outside of the circular membrane are removed. Step 3: SNR Transformation. This levels the images to account for uneven lighting on the image. There are many ways to do this. Including rolling ball method, high pass filters, Fast fourier transforms, etc. Images are equalized by normalizing intensities to the local median value. This is accomplished by taking the higher intensity image and dividing the intensity of each pixel by the factor F, where F=median of a large neighborhood around the pixel. This is done to both the "before" and "after" images Step 4: Background subtract. In order to identify particles with respect to the membrane texture the transformed images are divided be each other pixel-wise. Thus we obtain two ratio images "before"/"after" and "after"/"before", the second is used to detect particles that got trapped after the "before" image was taken Step 5: Threshold the "before" image. We use a thresholding technique to identify particles. We do this by thresholding an image such that all pixels that are brighter than the threshold bright pixels turn white (value 1) and all pixels dimmer than the threshold turn black (value 0). Several threshold values can be used, but we typically use some multiple of the average background intensity. Currently we use 2 times the background intensity. After this some additional processing can be done to close edges and fill gaps. A "blob" of connected white pixels is considered a particle. See FIG. 18A "Before Image". Step 6. The mask is applied to the image so that the locations of particles can be measured to provide brightness, morphological and positional data about each particle. These details are recorded in a table. Step 7: In the "after"/"before" image we can pick a threshold higher than 1 to detect the added particles. To pick the optimal threshold the following steps are performed according to certain embodiments. Method 1: We pick an "after"/"before" image threshold by the following method. We make several guesses at a threshold value. For each guess, we apply the threshold to the image, identify particles and compile a list of particles found using this threshold. Then we compare the after particles to the before particles. For each "before" particle we find the closest "after" particle and assign the connected pair a "benefit" value. The lower the distance of the particles' centroids, the more similar the areas of the particles, the more similar the brightness, the more similar the morphological features are, the higher the benefit. Not all of these attributes need to be used though. For the guessed "after" image threshold, a total value for connected particle "benefit" is calculated by summing up each connected particle pair. Next, we attempt to maximize the benefit by picking the best "after" threshold. This can be done by iteratively making guesses and changing the threshold after each guess in the direction that appears to be correct. This is a kind of feedback loop. Alternatively, a series of predetermined thresholds can be calculated and then a curve fitting or estimation method to can be used pick the threshold with the maximum "benefit". Ideally, every particle found in the before image should correspond to a particle in the after image. However, some particles may have shifted or disappeared. See FIGS. 18A-18C. The before image (FIG. 18A) was thresholded and 5 particles were identified in this section of the before image. After identifying a good "after" threshold as described in step 7 above, the after image (FIG. 18B) identified 16 particles. The 5 particles from the before image were connected to the after image and are shown with arrows in FIG. 18C. There will therefore be 11 new particles reported in this section of the membrane. Method 2: For each particle found in the before image, we look at the same region in the after image and determine what threshold would produce the highest "benefit". After doing this for each particle we pick a threshold, or even multiple theresholds that give the best result. Step 8: Attempt to find particles that have shifted. Some particles that were in the before image but not the after image can attempt to be located by looking for particles in the after image that have the same morphological and brightness characteristics. Step 9: After the connected particles have been identified, the remainder of the identified particles in the after image can be reported.

Figure 19A:
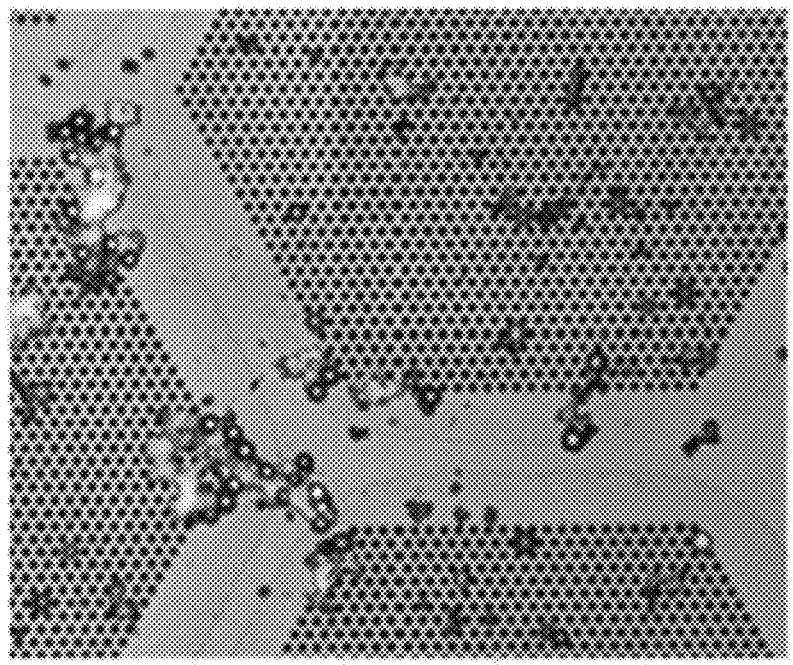
FIG. 19A depicts particles on a hex filter showing differentiation between two types of materials via fluorescence characterization according to one embodiment.
Figure 19B:
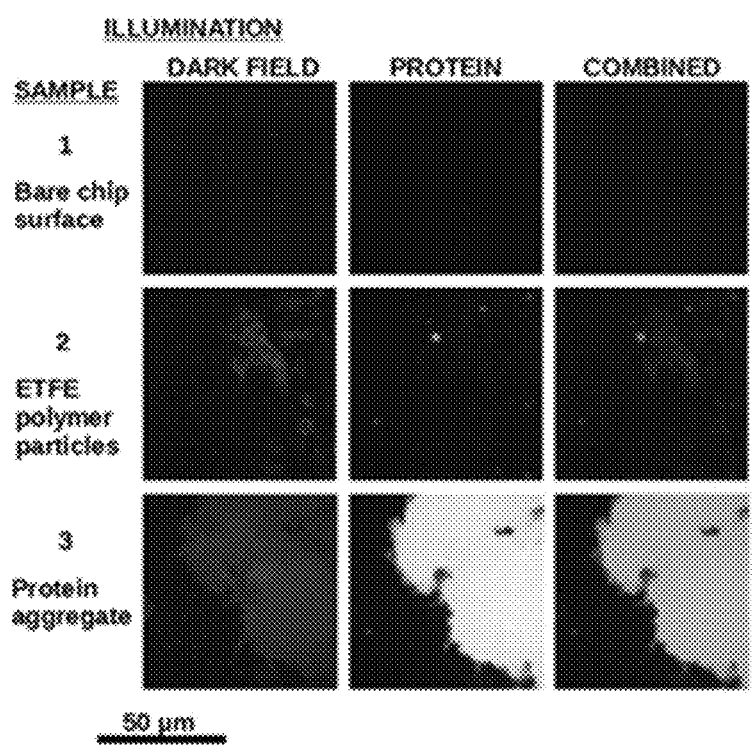
FIG. 19B depicts the hex filter's ability to distinguish between ETFE polymeric standards that mimic protein aggregates with actual protein aggregates.

In one aspect, different particles can be distinguished based on differences in intrinsic fluorescence properties. Fluorescent imaging is a reliable and rapid method for quantitatively evaluating protein auto-fluorescence, since they fluorescence in the deep-UV wavelength range (excitation ~280 nm, emission 303 nm and 350 nm) due to the presence of constituent aromatic amino acids. To test fluorescence characterization, we prepared a mock biopharmaceutical sample consisting of protein aggregates (bovine granulocyte colony stimulating factor) and a polydisperse mixture of polystyrene particles. In addition to capturing a 'dark-field' image used for counting, fluorescence typing images were acquired as well using a protein intrinsic fluorescence channel. The results, shown in FIGS. 19A and 19B show easy differentiation between the two types of materials. Different imaging modes shown in the top of the plot can be combined and processed to "clip out" individual particles and plot their characteristics. In general, particles with the least amount of protein signal (the polymer microspheres) match the morphology of the spiked non-protein particles. Rounder particles (polystyrene) were also the ones that exhibited the least fluorescence in the protein channel. In addition, protein aggregates fluoresce in the larger UV-blue wavelengths (excitation ~340 nm, emission 425, 445, 470, and 500 nm), with this aggregate fluorescence stems from the presence of higher-order aggregate structure or resonant bond features, and may even reveal information of the aggregate structure (e.g. random vs. fibril) and to distinguish between dissolvable (dangerous) vs. non-dissolvable aggregates. The system can also distinguish between ETFE polymeric standards that mimic protein aggregates with actual protein aggregates, as shown in FIG. 19B.

In one embodiment, the imaging device is configured to image the filter both before and after the at least one particle is captured on the filter. In one embodiment, the before and after images are processed together using algorithms that processes them to find differences. In one embodiment, the imaging device is configured to take a plurality of images at a plurality of heights above the filter. In one embodiment, the plurality of images consists of a high dynamic range set of exposures. In one embodiment, the plurality of images are merged together into a single image. In one embodiment, the plurality of images comprises replicates. In one embodiment, the plurality of images at different heights are merged together into a single image. In one embodiment, two or more images are mathematically registered. In one embodiment, the before and after images are mathematically registered. In one embodiment, a median filter is used to process the image.

Figure 20A:
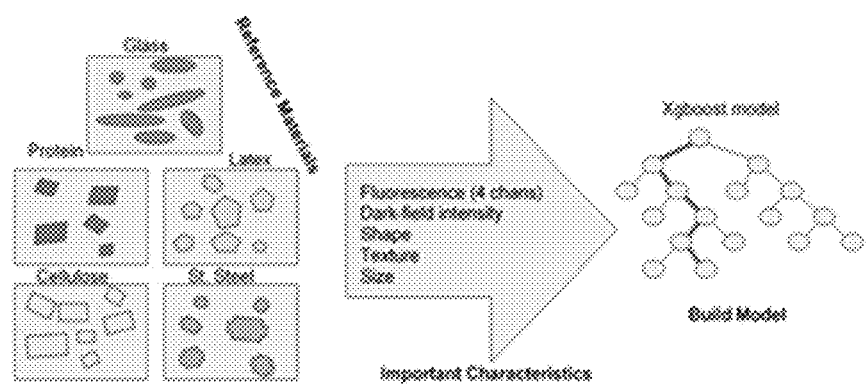
FIG. 20A shows a schematic for building a machine learning model according to one embodiment.
Figure 20B:
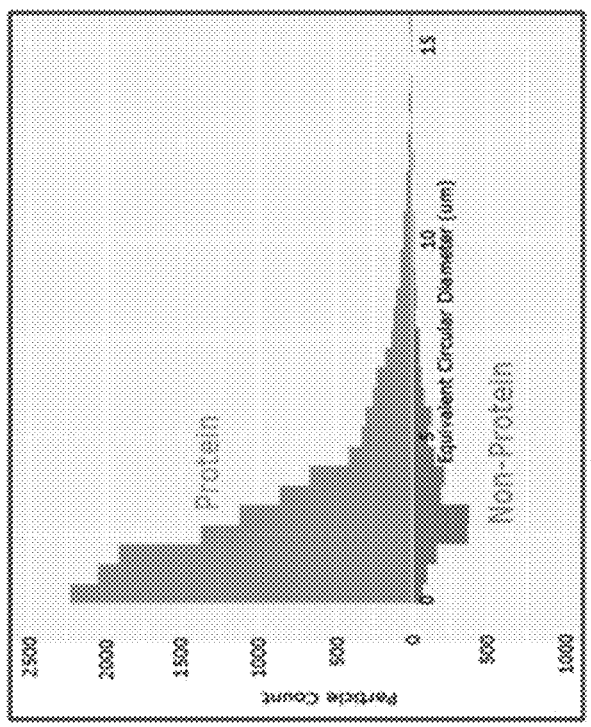
FIG. 20B shows an example output plot of protein vs non-protein identification according to one embodiment.

Machine learning algorithms were used to distinguish between different particle types. Different features were used, including size, shape and intrinsic fluorescence, to build the models. To test feasibility of using machine learning to classify particles, we collected a data set containing ~40,000 particle images. The training set consisted of protein aggregates, glass particles, cellulose particles, stainless steel particles, ETFE standards from NIST, and latex beads. 50% of the dataset was set aside to be used as a testing set for final evaluation of the predictive model. The remaining 50% was used to train a machine learning algorithm, xgboost, short for extreme gradient boosting. For this model, only the intensity signal-to-noise ratios for a darkfield illumination channel and each fluorescence channel were used as features. The building of the model is shown schematically in FIG. 20A. In short, images collected of known particles are analyzed and the extracted parameters are used to construct a series of decision trees, which are then used to classify particles of unknown type. First, an xgboost model was trained with the training data to perform predictions on the simple case of proteinaceous (protein aggregates) vs non-proteinaceous (all other particle types) typing. The model consisted of 100 decision trees, and yielded an accuracy on the testing set of 95.5%, sensitivity of 97.9%, and specificity of 77.4%. In this case, 16,238 non-protein particles were correctly identified as being non-protein, and 342 particles were mistakenly classified as proteins. 1727 protein aggregates were correctly identified as proteinaceous particles, and 504 were incorrectly classified as non-proteinaceous. An example output plot of protein vs non-protein identification is shown in FIG. 20B, collected on a mixed sample containing protein aggregates and latex beads. For multi-class classification, the same xgboost algorithm was trained to identify individual particle types, instead of simple proteinaceous or non-proteinaceous determination. The same training data was used (SNR for each channel), and an xgboost model consisting of 100 decision trees yielded a typing accuracy of 88.6%, with specificities ranging from 89.7-99.7%, and sensitivities ranging from 69.2-95.1%. The confusion matrix of labeled versus predictive cases is shown in FIG. 19B, where the diagonal represents correctly identified cases.

Figure 21A:
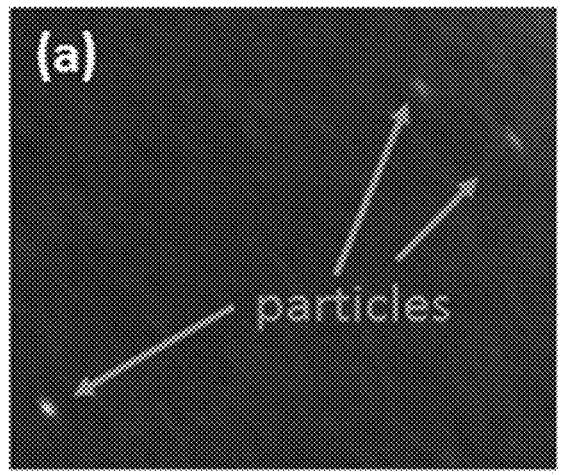
FIG. 21A is an out of focus image of particles and FIG. 21B is a corrected image of particles after a focus fusion technique is applied.
Figure 21B:
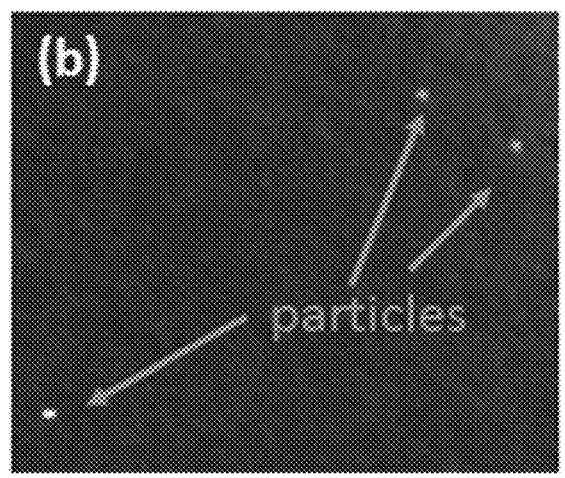

With reference now to FIGS. 21A and 21B, the membrane where particles are captured and imaged were usually never perfectly in focus throughout the whole image (FIG. 21A) for one image. There may be local membrane deformations, spherical aberration at the image edges, the presence of large particles which are partially out of focus, and mechanical misalignment or flatness. We employ a technique known as focus fusion to combat these issues. The technique is not novel, but, when used in conjunction with all of the other techniques, is an essential part of what makes the overall imaging work. Focus fusion works by taking many images at different heights above the substrate and merging them into a single "focus fused" image (FIG. 21B). This dramatically improves the feature detail across the whole image, enabling the system to accurately remove background texture, acquire physical parameters including counts, size and provides higher fidelity regarding intensity measurements, and ensures that particles that are out of focus do not appear large and dim. This technique is used in combination with other imaging techniques such as HDR imaging mentioned earlier and taking multiple averages of the same image to improve image quality and reduce noise.

With reference now to FIGS. 25-39, experimental examples related to novel aspects of the filter membranes and related data are explained in more detail. Key for fluorescence work on particles is membranes that support fluorescent work. Certain embodiments include low background fluorescence membranes or commercially available ones. The membranes need to support image analysis (optically smooth). Track etched membranes have their pores defined via synchrotrons ablation, to have very uniform shape (pores are etched hollow cylinders, not like a complex glass fiber porous matrix). This enables well defined pores and also optically smooth surfaces, important for particle characterization. Unlike for example fibrous membranes, where the background of the fibers makes it matte, textured, and complicated to distinguish between the particles in the sample from the membrane itself.

In one embodiment, membranes that support fluorescence are dyed with a photo absorber, limiting the background fluorescence of the membrane. This is very important since polymer membranes can have dramatically high intrinsic fluorescence, obfuscating any signal coming from a thin protein aggregate, even if this protein aggregate was properly dyed.

Figure 25:
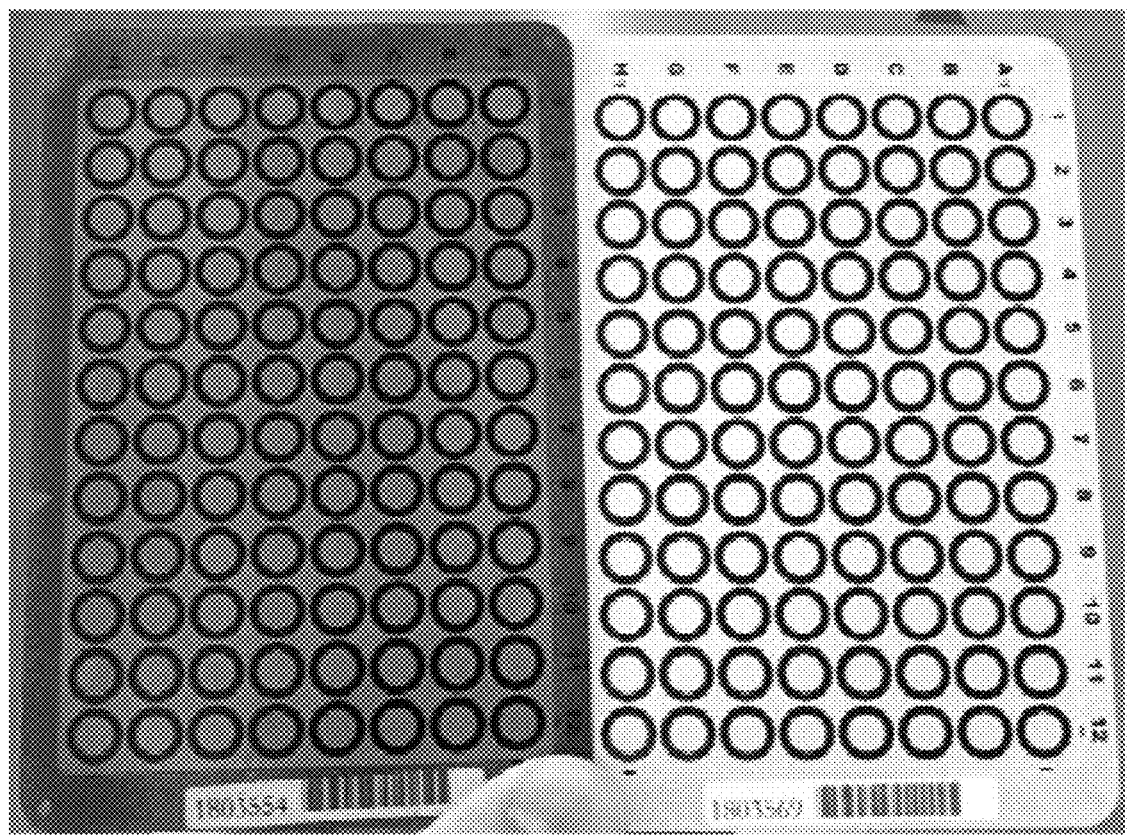
FIG. 25 is an image of a white membranes and a membrane incubated in a Sudan black ethanol solution according to one embodiment.
Figure 26:
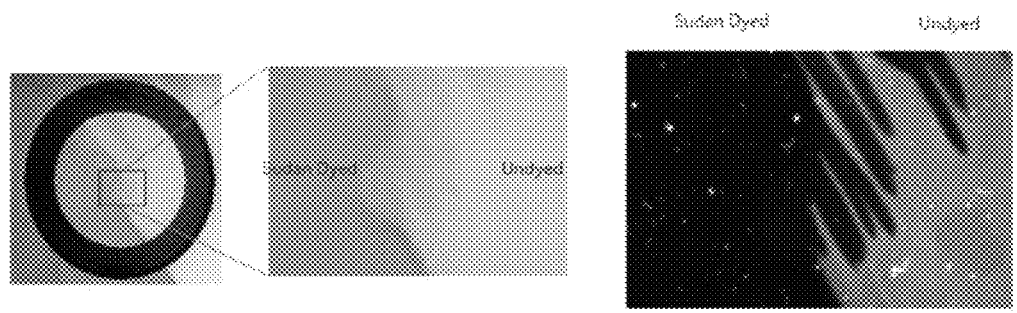
FIG. 26 shows images of the black dye helping to block background fluorescence according to one embodiment.
Figure 27:
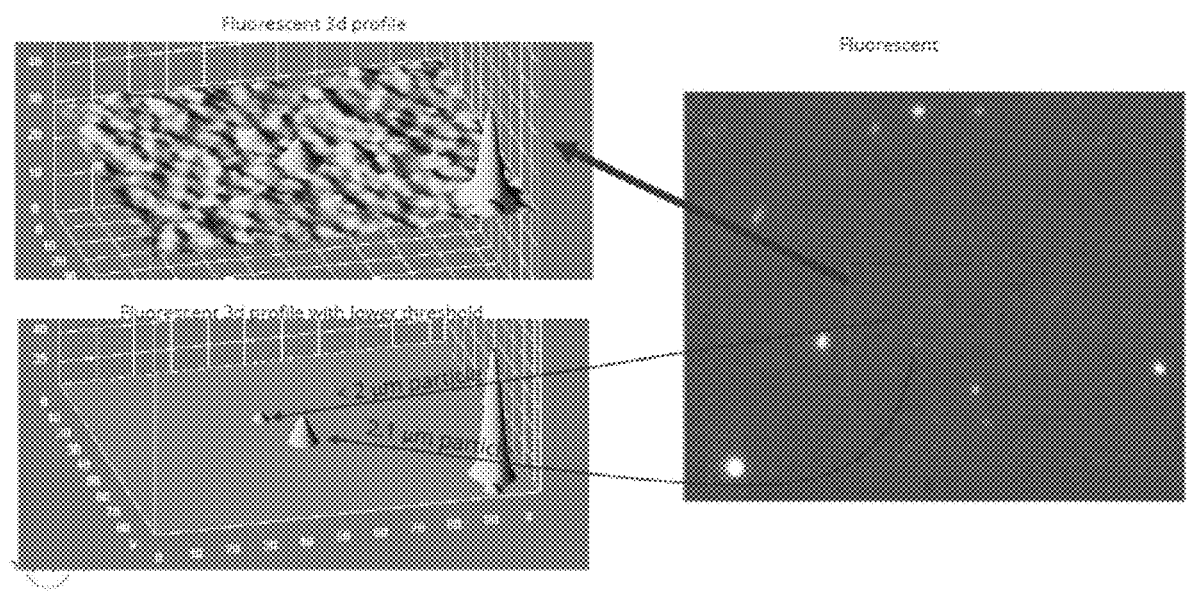
FIG. 27 shows data of a high signal to background ratio (the background fluorescence of the membrane) for particles (2 um) according to one embodiment.
Figure 28:
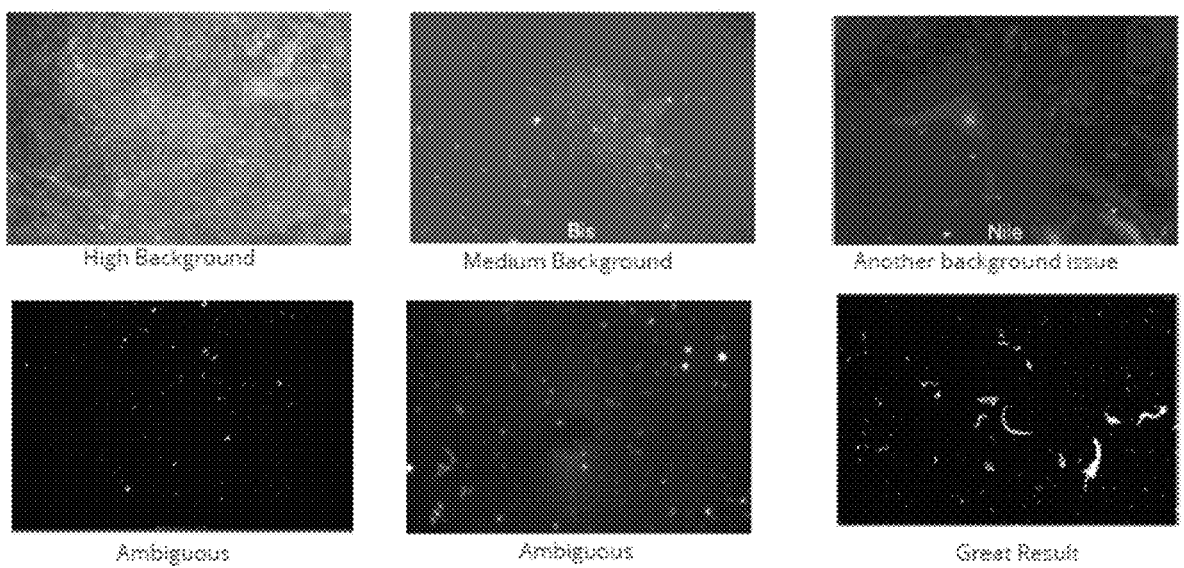
FIG. 28 shows illustrates the difference in using a low fluorescence membrane vs. not using a low fluorescence membrane according to one embodiment.
Figure 29:
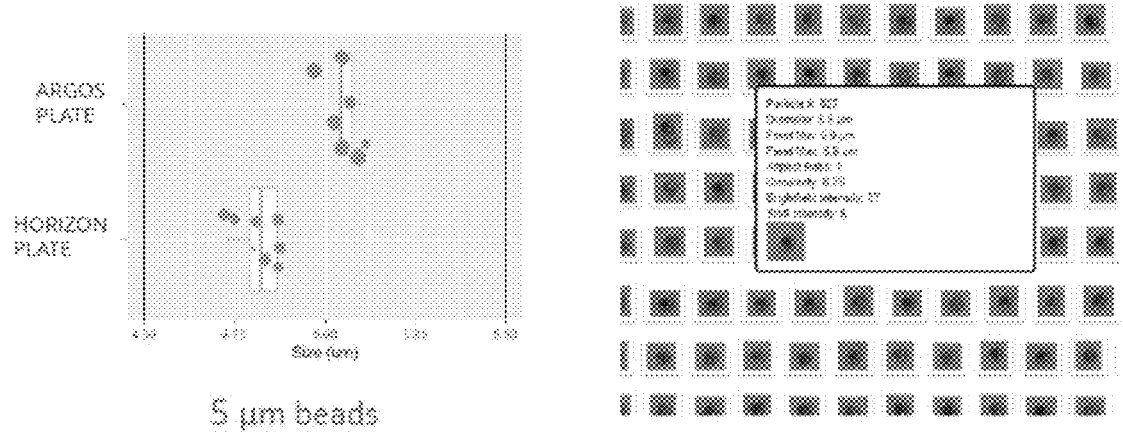
FIGS. 29-32 illustrate standard particle analysis (sizing and counting), which works well on black track etched membranes according to one embodiment.
Figure 30:
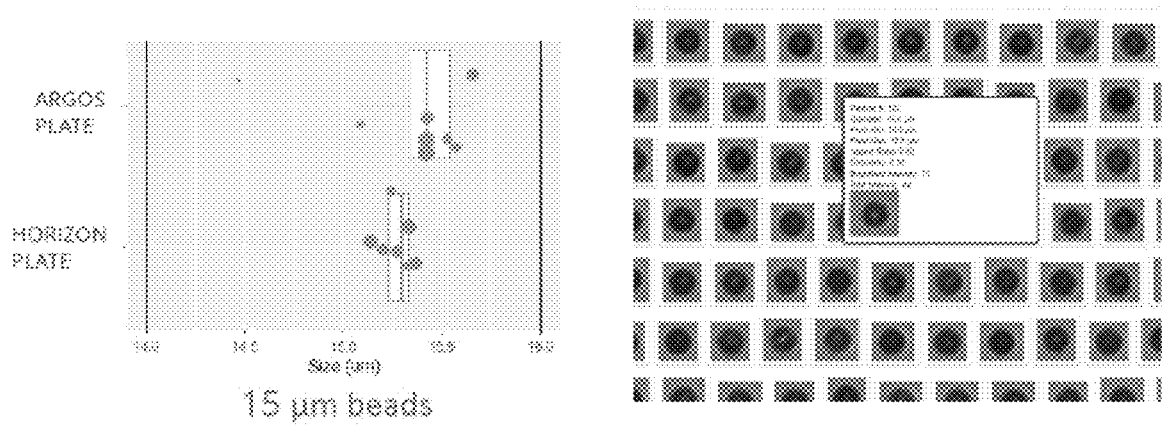
Figure 31:
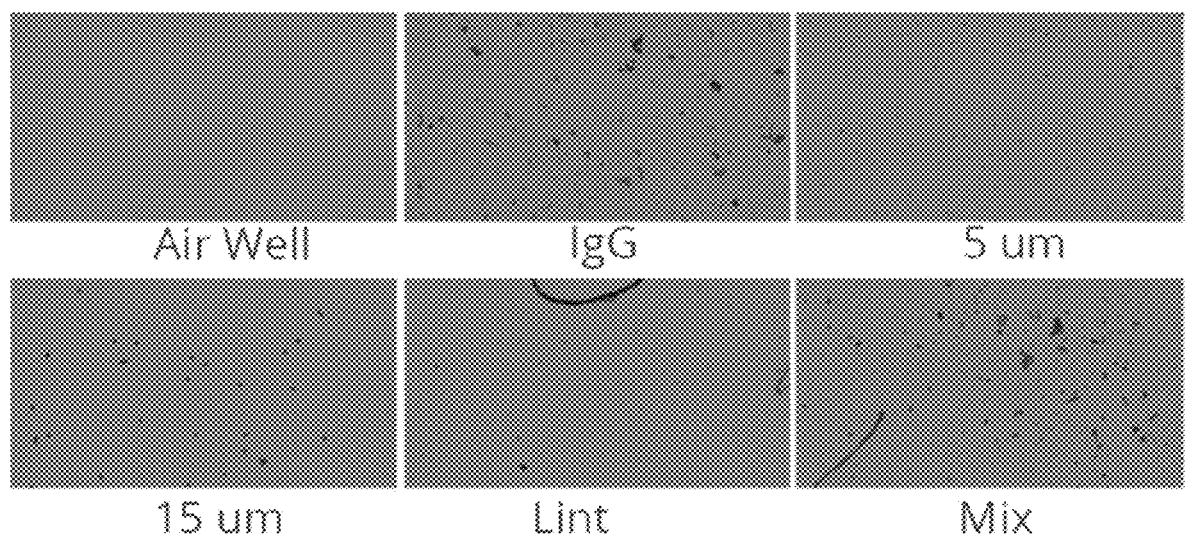
Figure 32:
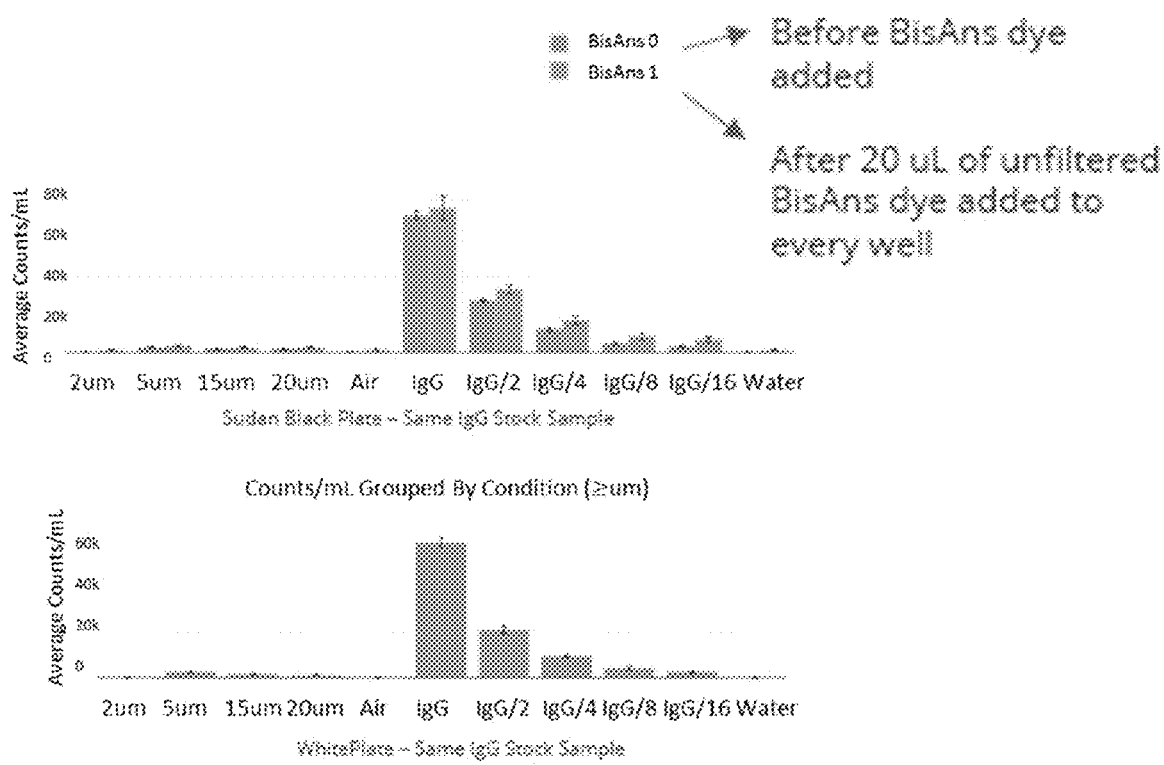

In one embodiment, Sudan Black dye is used to work as the photo absorber. Sudan black power was formulated at 50% w/v with Ethanol. For this, the original white polycarbonate and polyester membranes are incubated in this Sudan black ethanol solution, and it dyes the membranes. The contrast between the two is shown in FIG. 25. As shown in FIG. 26, the black dye helps block background fluorescence. The images show a well that was half-dyed. The SNR improvement is shown (far right image) on the side with the Sudan Dye. FIG. 27 shows a high signal to background ratio (the background fluorescence of the membrane) even for the smallest particles (2 um). FIG. 28 illustrates the difference in using a low fluorescence membrane vs. not using a low fluorescence membrane. When the background fluorescent signal is too high, you can't obtain a good reliable signal from the proteins, so the specially prepared membranes should be utilized. FIGS. 29-32 illustrate standard particle analysis (sizing and counting), which works well on black track etched membranes. Sizing and imaging of 5 um beads (FIG. 29) vs. 15 um beads (FIG. 30) on black membranes is shown. FIG. 31 shows brightfield difference images (difference between after and before image on a white plate) in black plates for several samples. Black plates give the same results as standard white plates, which is beneficial (FIG. 32).

Figure 33:
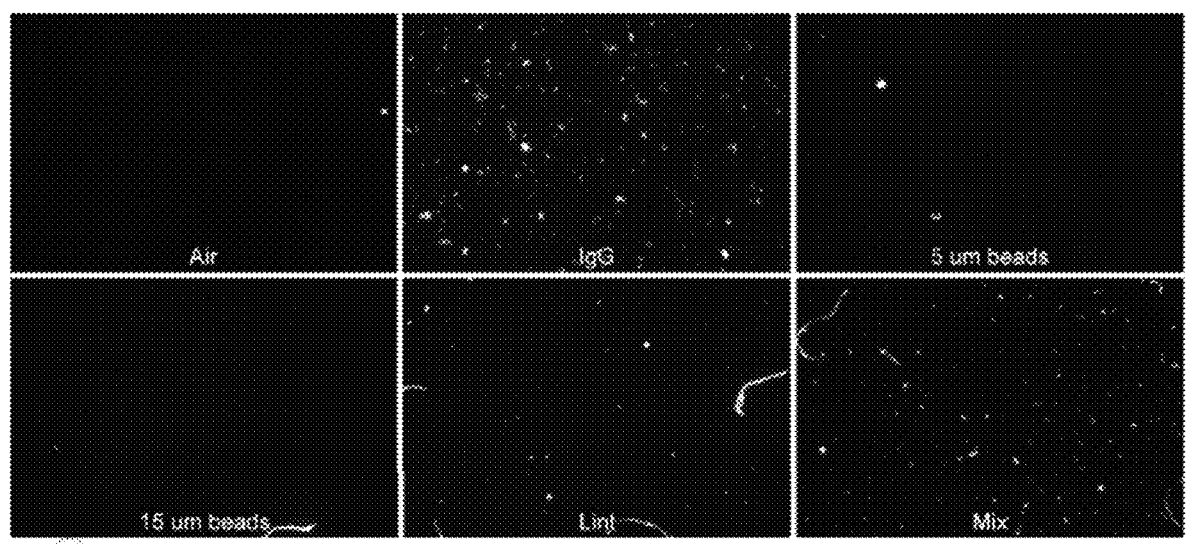
FIG. 33 shows fluorescence images of particles dyed with Bis Ans dye, on a Sudan Black plate according to one embodiment.

With reference now to FIG. 33, fluorescence images of particles dyed with Bis Ans dye, on a Sudan Black plate are shown. The images show how IgG aggregates fluoresce when dyed with bis Ans, but the rest of the membrane remains black. Plastic beads without fluorescence do not fluoresce under bis Ans dye. However, some non-protein particles like Lint can glow in this channel. It is important to conduct a prior background fluorescence to background out any lint (dust, skin cells), that may be present in the ambient air.

Figure 34:
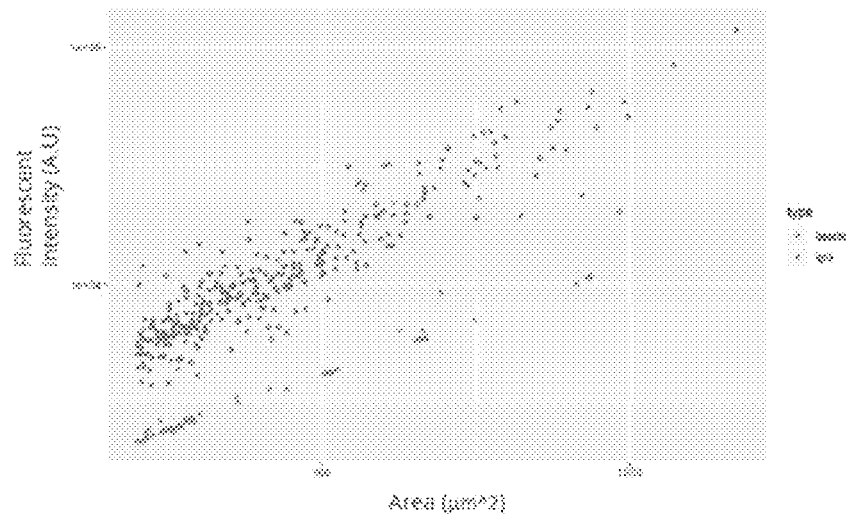
FIGS. 34-36 show separation of proteinaceous and non-proteinaceous particles according to one embodiment.
Figure 35:
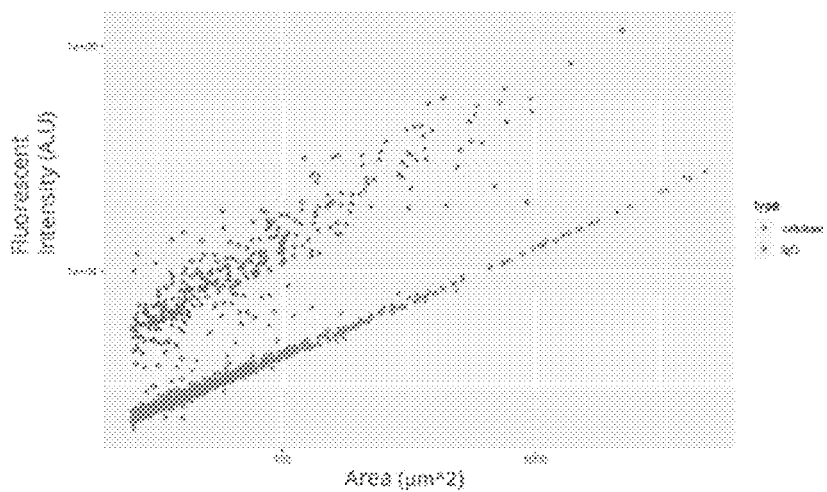
Figure 36:
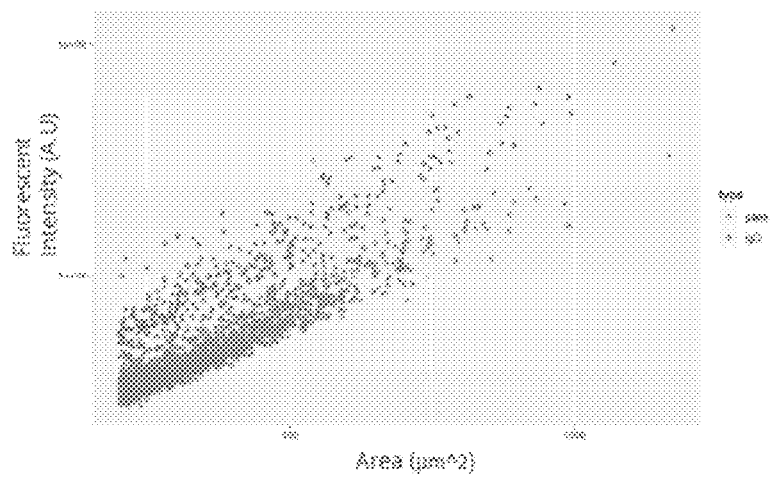

With reference now to FIGS. 34-36, >90% Separation of proteinaceous and non-proteinaceous particles is demonstrated via this approach. In these examples, we differentiate with >90% accuracy between the drug product (igg) vs. glass, beads and cellulose. Note that the drug product is a protein, but when it degrades due to lack of stability it can aggregate.

Figure 37:
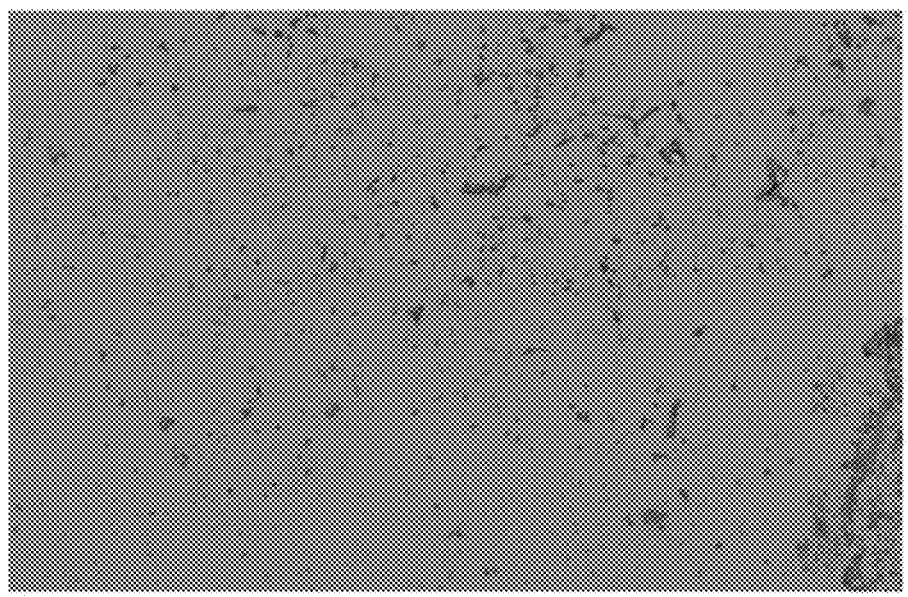
FIGS. 37 and 38 illustrate particle mixtures according to one embodiment.
Figure 38:
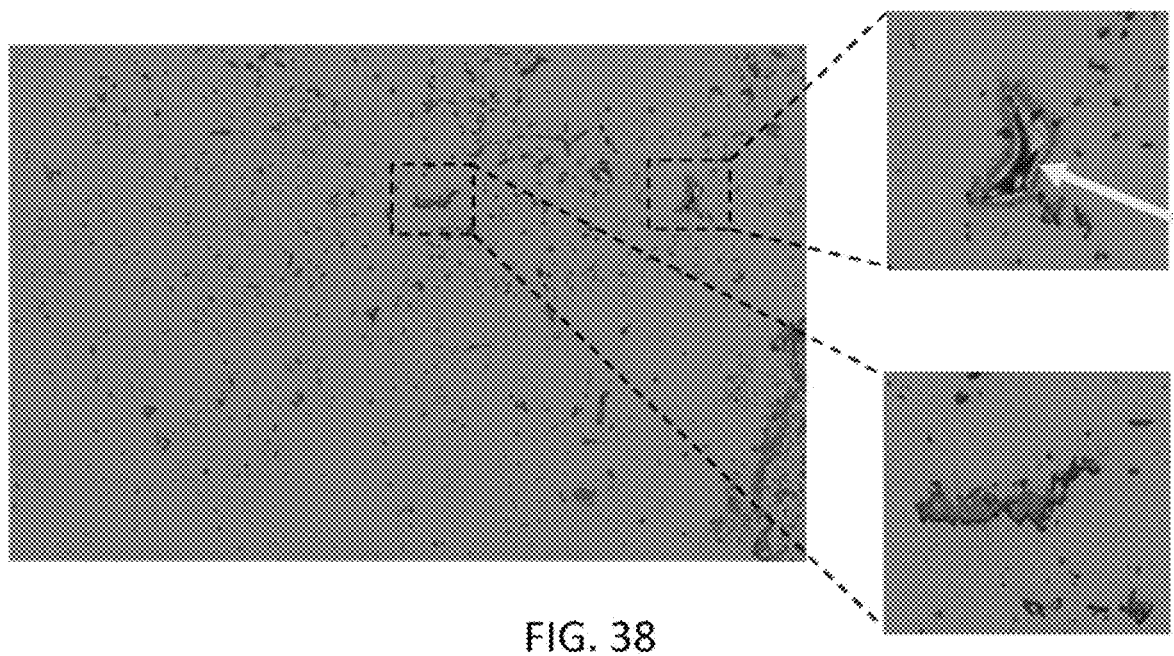

With reference now to FIGS. 37 and 38, we can also look at particle mixtures. These are plastic particles. We can see how protein (fluoresces) can bind to portions of the plastic particles. This is important since not only is it important to differentiate between protein aggregates and non, but there are mixes.

Figure 39:
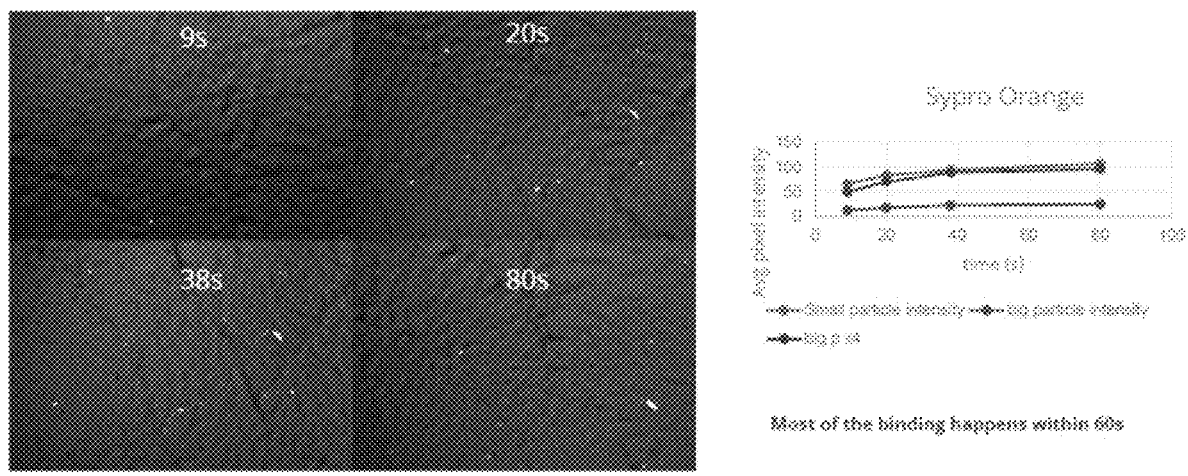
FIG. 39 illustrates the speed of dye binding according to one embodiment.

With reference now to FIG. 39, it is important to note that most of the dye binds within 60 seconds. A regular membrane can't be used if it does not support fluorescence work, since the dye binds very quickly to both the protein and the membrane. Membranes according to the embodiments described herein are effective.

Figure 40:
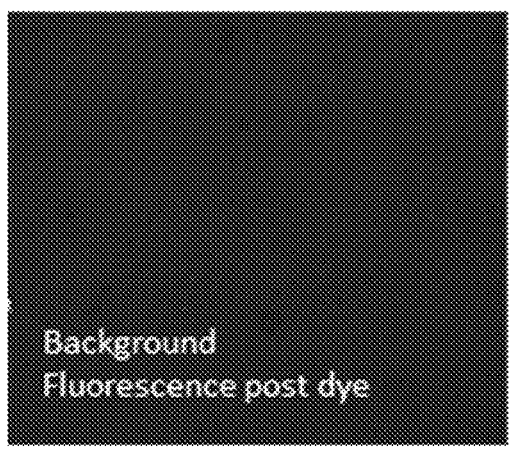
FIG. 40 shows comparative images illustrating the effect of fluorescent backgrounds before and after dye are shown according to one embodiment.

With reference now to FIG. 40, comparative images showing the effect of fluorescent backgrounds before and after dye are shown. The images show sample background intensities for 16-bit images: Min=0, Max=65,434, 5 second exposure, and 10× gain. The image on the left is It4IP 400 nm polycarbonate black plate while the image on the right shows a white plate. White plates (or non-black plates) do not support fluorescence.

Figure 41:
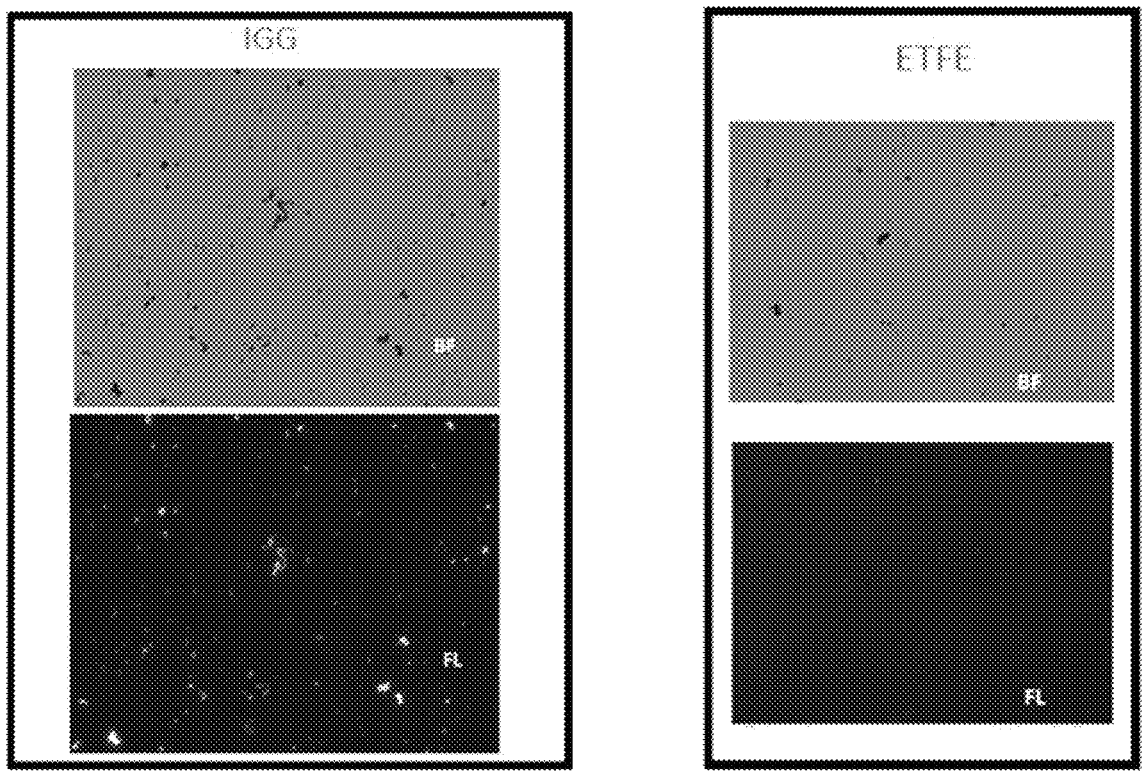
FIG. 41 shows an IGG and ETFE image according to one embodiment.

With reference now to FIG. 41, an IGG and ETFE image are shown.

Figure 42:
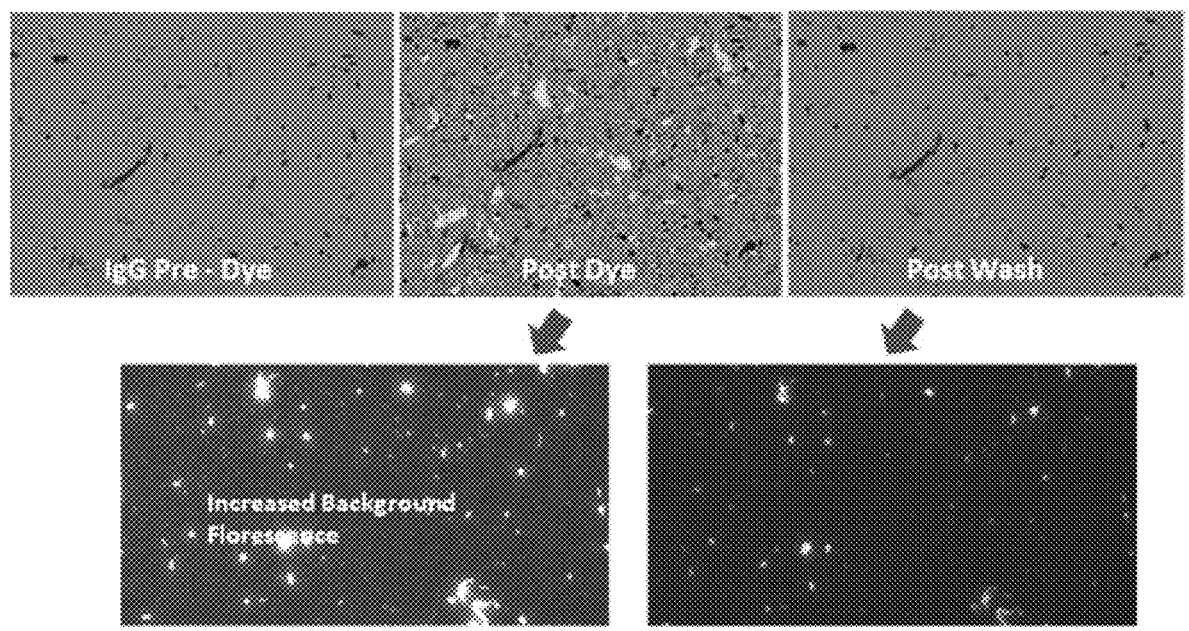
FIG. 42 shows images from a method of rinsing with water after adding dye according to one embodiment.

With reference now to FIG. 42, images from a method of rinsing with water after adding dye is shown. This method can be used to reduce dye crystal false positives. The rinse step can be used after adding dye since it can crystalize on the membrane.

Figure 43:
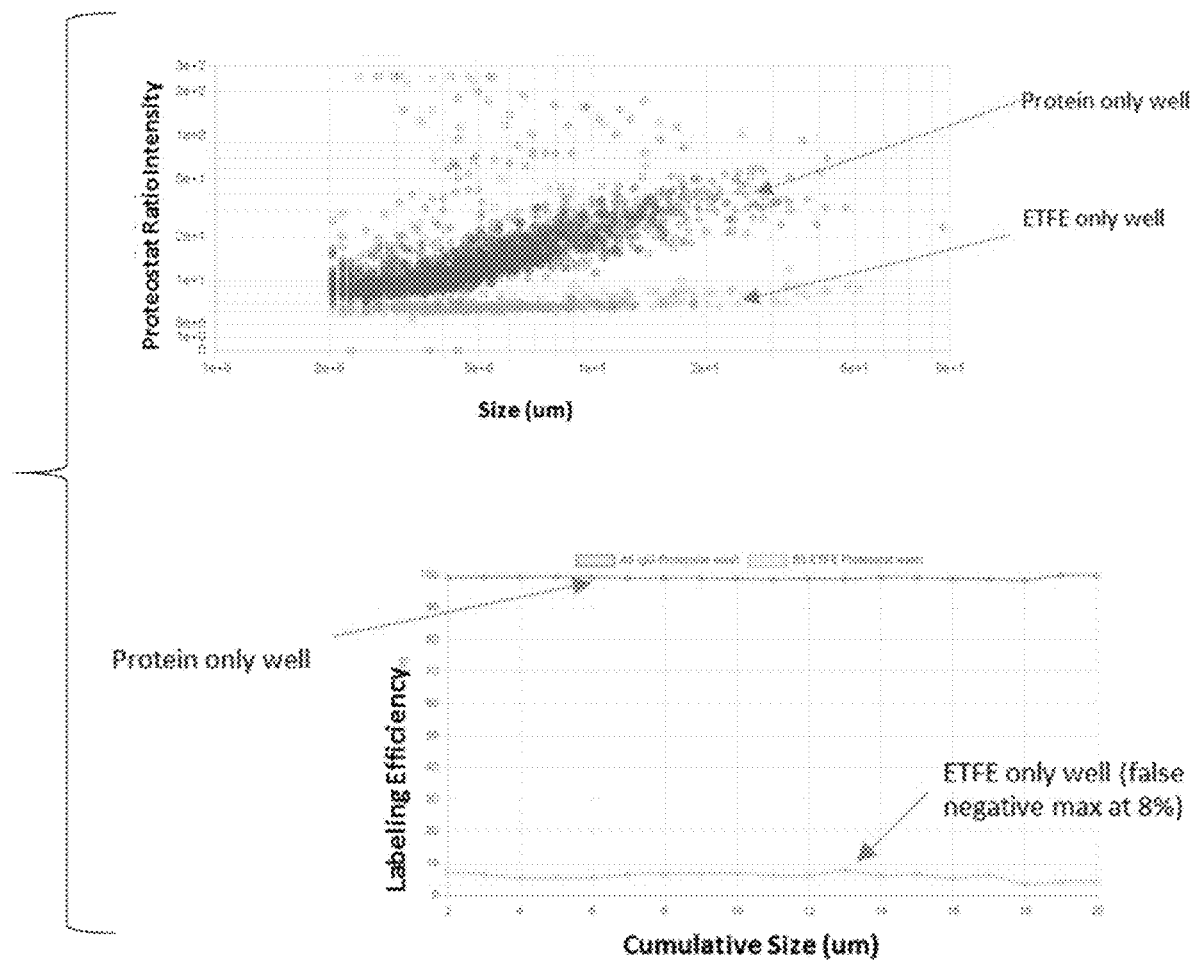
FIG. 43 shows data demonstrating >90% protein vs. non-protein results according to one embodiment.

With reference now to FIG. 43, data demonstrating >90% protein vs. non-protein results is shown. The ratio of background to after fluorescent intensities on a per particle basis reduces noise in data fluorescence data. Very high Protein vs. non protein (ETFE) signals can be obtained by analyzing the data as ratios of fluorescence.

With reference now to FIG. 44, a data separation table is shown. Analysis of data separation: 10% percentile of IgG is your weakest glowing proteins, 90% ETFE are your highest glowing non proteins. The things that are supposed to fluoresce can be separated from those that don't with ratios >3×. Some of the ratios decrease as more ETFE false positives increase.

Figure 45:
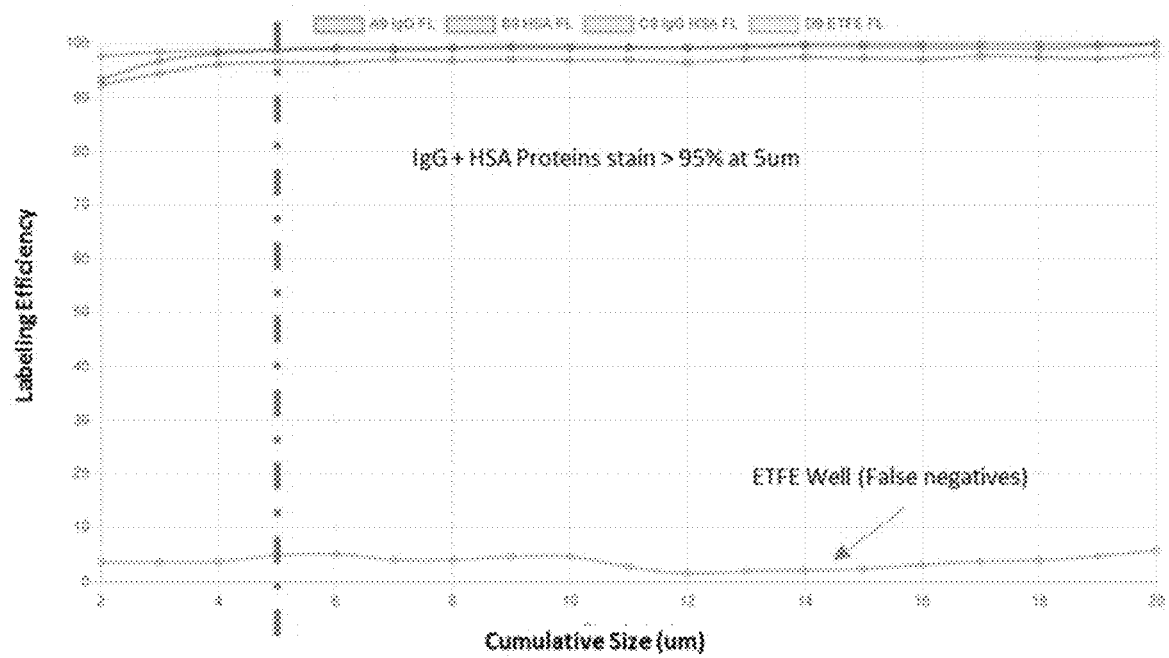
FIG. 45 is a graph demonstrating that certain stains can stain different proteins efficiently according to one embodiment.

With reference now to FIG. 45, a graph is shown to demonstrate that a stain such as Proteostat can stain different proteins efficiently. Proteostat can stain many different proteins like IgG and HAS.

Figure 46:
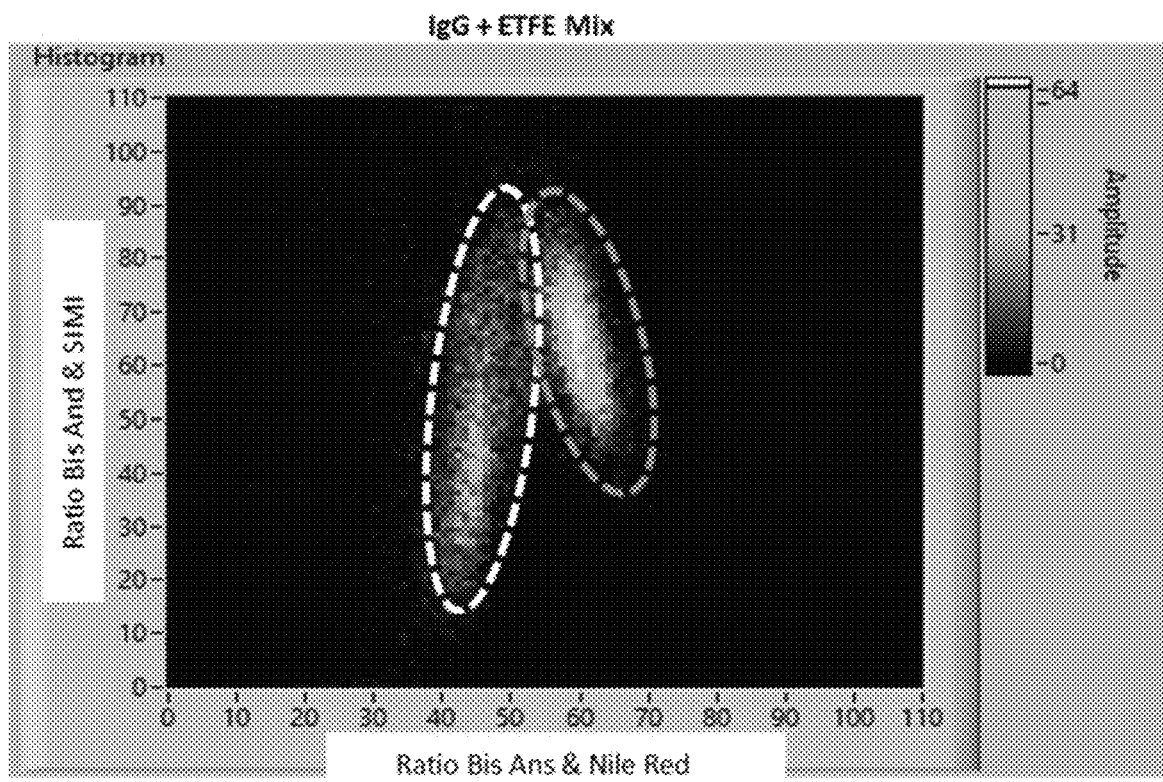
FIG. 46 is a graph showing multiple fluorescent channels according to one embodiment.

With reference now to FIG. 46, as shown in the graph, multiple fluorescent channels (SIMI is darkfield—not fluorescence) separation of the data more to get more insight. Presenting the data in ratios of fluorescence instead of FL vs size also gets rid of size effects on the data. This is how many flow cytometers present their multichannel data.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method of distinguishing between proteinaceous and non-proteinaceous particulates in a fluid sample comprising:
   acquiring a brightfield background image of a membrane filter while the membrane filter is free of a fluid sample;
   introducing a fluid sample onto the membrane filter;
   acquiring a brightfield image of filtered particles resting on the membrane filter;
   generating a particle mask based on the brightfield background image and the brightfield image of filtered particles;
   introducing a fluorescent dye onto the membrane filter;
   detecting fluorescence on the particle mask; and
   distinguishing between proteinaceous and non-proteinaceous particulates based on the detected fluorescence.

2. The method of claim 1 further comprising:
   generating a total particle distribution, a protein particle distribution, and a non-protein particle distribution based on the distinguishing.

3. The method of claim 1 further comprising:
   generating an image of protein and non-protein particles, wherein the protein and non-protein particles are different colors.

4. The method of claim 1 further comprising:
   ignoring data outside the particle mask for the steps of detecting and distinguishing.

5. The method of claim 1 further comprising:
   acquiring a background fluorescence and removing baseline fluorescent intensity.

6. The method of claim 1, wherein the step of introducing a fluorescent die takes place immediately after the step of introducing a fluid sample onto the membrane filter.

7. The method of claim 1, wherein the fluorescent dye is introduced to the fluid sample prior to the step of introducing the fluid sample onto the membrane filter.

8. The method of claim 1, wherein the membrane filter is a track etched membrane.

9. The method of claim 1, wherein the membrane filter is dyed with a fluorescence photo absorber.

10. The method of claim 9, wherein the photo absorber comprises sudan black dye.

11. The method of claim 1, wherein the membrane filter comprises a polycarbonate or polyester.

12. The method of claim 1, wherein the membrane filter is coated with PVP.

13. The method of claim 1, wherein the step of introducing a fluorescent dye comprises introducing between 5 and 50 uL of dye.

14. The method of claim 1, wherein the fluid sample is bounded by a hydrophobic ring disposed on a well plate.

15. The method of claim 1 further comprising:
   individually and separately imaging a plurality of filtrate samples bounded by a plurality of hydrophobic rings disposed on the well plate.

16. A method of distinguishing between particulates in a fluid sample comprising:
   acquiring a brightfield background image of a membrane filter while the membrane filter is free of a fluid sample;
   introducing a fluid sample onto the membrane filter;
   acquiring a brightfield image of filtered particles resting on the membrane filter;

generating a particle mask based on the brightfield background image and the brightfield image of filtered particles;
introducing a fluorescent dye onto the membrane filter;
detecting fluorescence on the particle mask; and
distinguishing between particulates based on the detected fluorescence.

17. The method of claim 16, wherein the fluorescent dye is selected for detecting protein particles.

18. The method of claim 7, wherein the fluorescent dye is a protein aggregate dye.

19. The method of claim 17, wherein the fluorescent dye is a monomer dye.

20. The method of claim 16, wherein the fluorescent dye is selected for detecting polysorbate particles.

21. The method of claim 16, wherein the fluorescent dye is selected for detecting silicone oil.

22. The method of claim 16, wherein the fluorescent dye is selected for detecting protein monomers.

23. The method of claim 16 further comprising:
ignoring data outside the particle mask for the steps of detecting and distinguishing.

24. The method of claim 16 further comprising:
acquiring a background fluorescence and removing baseline fluorescent intensity.

25. The method of claim 16, wherein the membrane filter is dyed with a fluorescence photo absorber.

26. The method of claim 25, wherein the photo absorber comprises sudan black dye.

* * * * *